United States Patent
Connelly et al.

(10) Patent No.: US 6,649,375 B2
(45) Date of Patent: *Nov. 18, 2003

(54) ADENOVIRAL VECTORS FOR ENHANCED GENE EXPRESSION

(75) Inventors: Sheila Connelly, Gaithersburg, MD (US); Michael Kaleko, Rockville, MD (US); Theodore Smith, Germantown, MD (US)

(73) Assignee: Genetic Theraphy, Inc., Gaithersburg, MD (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/150,811

(22) Filed: Sep. 10, 1998

(65) Prior Publication Data

US 2002/0064812 A1 May 30, 2002

Related U.S. Application Data

(63) Continuation of application No. 08/484,891, filed on Jun. 7, 1995, now Pat. No. 5,935,935, which is a continuation-in-part of application No. 08/218,335, filed on Mar. 25, 1994, now abandoned, which is a continuation-in-part of application No. 08/074,920, filed on Jun. 10, 1993, now abandoned.

(51) Int. Cl.[7] .............. C12P 21/02; C12N 15/861; C12N 15/63; C07H 21/04

(52) U.S. Cl. .............. 435/69.51; 435/320.1; 435/69.1; 435/69.4; 435/69.5; 435/69.52; 435/69.6; 435/455; 435/456; 435/325; 435/91.4; 435/91.41; 536/23.1; 536/23.2; 536/23.4; 536/23.5; 536/24.1; 536/24.5

(58) Field of Search .............. 435/320.1, 69.1, 435/440, 455, 456, 235.1, 325, 91.4, 91.41; 536/23.1, 29.1, 23.2, 23.4, 23.5, 24.1, 24.5; 530/350

(56) References Cited

U.S. PATENT DOCUMENTS

| | | | |
|---|---|---|---|
| 4,716,117 A | 12/1987 | Kuo et al. | |
| 4,757,006 A | 7/1988 | Toole, Jr. et al. | |
| 4,868,112 A | 9/1989 | Toole, Jr. et al. | |
| 4,994,371 A | 2/1991 | Davie et al. | |
| 5,004,803 A | 4/1991 | Kaufman et al. | |
| 5,004,804 A | 4/1991 | Kuo et al. | |
| 5,032,511 A | 7/1991 | Takahashi et al. | |
| 5,045,455 A | 9/1991 | Kuo et al. | |
| 5,116,739 A | 5/1992 | Teranishi et al. | |
| 5,149,637 A | 9/1992 | Scandella et al. | |
| 5,670,488 A | 9/1997 | Gregory et al. | |
| 5,681,746 A | 10/1997 | Bodner et al. | |
| 5,935,935 A | * 8/1999 | Connelly et al. | 514/44 |
| 6,399,587 B1 | 6/2002 | Mehtali et al. | 514/44 |

FOREIGN PATENT DOCUMENTS

| | | |
|---|---|---|
| EP | 107278 | 11/1989 |
| FR | 2707664 | 1/1995 |
| WO | WO 93/03769 | 3/1993 |
| WO | WO 94/12649 | 6/1994 |
| WO | WO 94/28152 | 12/1994 |
| WO | WO 95/02697 | 1/1995 |
| WO | WO 96/14061 | 5/1996 |
| WO | WO 96/22378 | 7/1996 |
| ZA | 94/5012 | 7/1994 |
| ZA | 95/8128 | 9/1995 |
| ZA | 96/0454 | 1/1996 |

OTHER PUBLICATIONS

Friedman et al. Mol. and Cellular Biol. Vol 6(11): pp. 3791–3797, Nov. 1986.*
Levy et al. Proc. Nat'l. Acad. Sci. U.S.A. vol. 83: pp. 8929–8933, Dec. 1986.*
Thompson et al. Gene. vol. 96: pp. 257–262, 1990.*
Babiss et al. Mol. and Celluar Biol. vol. 6(11): pp. 3798–3806, Nov. 1986.*
Thompson et al. Biotechnology of Plasma Proteins, Lenfant et al. (eds.), pp. 59–62, Basel, Karger, 1991.*
Kaufman et al. Nature. vol. 342, pp. 207–208, Nov. 1989.*
Hoeben et al. J. Biol. Chem. vol. 265: pp. 7318–7328, 1991.*
Sorci–Thomas et al. J. Biol. Chem. vol. 266(27): pp. 10845–10850, 1991.*
Armentano, et al., PNAS, 87:6141–6145 (Aug. 1990).
Barinaga, M., Science, 266:1326 (1994).
Berkner, K., BioTechniques, 6(7):616–629 (1988).
Brinster, et al., PNAS, 85:836–840 (Feb. 1988).
Browler, G., British Medical Bulletin, 51(1):91–105 (1995).
Chan, et al., Nucl. Acids Res., 21(5):1205–1211 (Mar. 11, 1993).
Choi, et al., Mol. Cell Biol., 11(6):3070–3074 (Jun. 1991).
Choo, et al., Nucleic Acids Research, 15(3):871–884 (1987).
Connelly, et al., Blood, 87(11):4671–4677 (Jun. 1, 1996).
Connelly, et al., Human Gene Therapy, 6:185–193 (Feb. 1995).
Crystal, R., Science, 270:404–410 (1995).
Dai, et al., PNAS, 89:10892–10895 (Nov. 1992).
DiPersio, et al., Mol. Cell. Biol., 11(9):4405–4414 (Sep. 1991).
Engelhardt, et al., Human Gene Therapy, 4:759–769 (1993).
Gerrard, et al., Nature Genetics, 3:180–183 (Feb. 1993).

(List continued on next page.)

*Primary Examiner*—David Guzo
(74) *Attorney, Agent, or Firm*—Douglas A. Golightly; J. Timothy Meigs

(57) ABSTRACT

An adenoviral vector including at least one DNA sequence encoding a clotting factor, such as, for example, Factor VIII, or Factor IX. Such vectors may be administered to a host in an amount effective to treat hemophilia in the host. The vectors infect hepatocytes very efficiently, whereby the hepatocytes express the DNA sequence encoding the clotting factor.

106 Claims, 58 Drawing Sheets

OTHER PUBLICATIONS

Gunzburg, et al., Molecular Medicine Today, Elsevier Science, Ltd., 411–417 (1995).
Hoeben, et al., Human Gene Therapy, 4:179–186 (1993).
Hsueh, et al., Human Gene Therapy, 3:543–552 (1992).
Israel, et al., Blood, 75(5):1074–1080 (1990).
Jaffe, et al., Nature Genetics, 1:372–378 (Aug. 1992).
Jallat, et al., EMBO J, 9(10):3295–3301 (1990).
Jolly, D., Cancer Gene Therapy, 1(1):51–64 (1994).
Kaplan, et al., Gene Therapy, 3:117–127 (1996).
Kay, et al., PNAS, 91:2353–2357 (Mar. 1994).
Kay, et al., Science, 262:117–119 (Oct. 1, 1993).
Kopfler, et al., Clinical Research, 41(2):221A (Apr. 1993).
Li, et al., Human Gene Therapy, 4:403–409 (1993).
Lozier, et al., JAMA, 271(1):47–51 (Jan. 5, 1994).
Lu, et al., Science in China, 36(11):1342–1351 (Nov. 1993).
Lynch, et al., Human Gene Therapy, 4:259–272 (1993).
Marshall, E., Science, 269:1050–1055 (1995).
Mlller, et al., Blood, 76(2):271–278 (Jul. 15, 1990).
Miyanohara, et al., The New Biologist, 4(3):238–246 (Mar. 1992).
Orkin, et al., Report and Recommendations of the Panel to Assess the NIH Investment in Research on Gene Therapy (Dec. 1995).
Palmer, et al., Blood, 73(2):438–445 (Feb. 1989).
Scaria, et al., Gene Therapy, 4:611–617 (1997).
Scharfmann, et al., PNAS, 88:4626–4630 (Jun. 1991).
Smith, et al., Nature Genetics, 5:397–402 (1993).
Stratford–Perricaudet, et al., Bone Marrow Transplantation, 9(1):151–152 (Jan. 1992).
Stratford–Perricaudet, et al., Human Gene Therapy, 1:241–256 (1990).
Van der Vliet, et al., J. Virol., 15(2):348–354 (Feb. 1975).
Wilson, J.. Am Med. Assoc.. 269(7):837–838 (Feb. 17, 1993).
Yang, et al., Journal of Virology, 69(4):2004–2015 (Apr. 1995).
Yang, et al., Journal of Virology, 70(10):7209–7212 (Oct. 1996).
Zabner, et al., Cell, 75:207–216 (Oct. 1993).
Zhou, et al., Science in China, 36(9):33–41 (Sep. 1993).

* cited by examiner

FIG. 6

| | | | | | |
|---|---|---|---|---|---|
| 661 | AATCATTTAA | TGACTTCACT | CGGGTTGTTG | GTGGAGAAGA | TGCCAAACCA | GGTCAATTCC |
| 721 | CTTGGCAGGT | TGTTTTGAAT | GGTAAAGTTG | ATGCATTCTG | TGGAGGCTCT | ATCGTTAATG |
| 781 | AAAATGGAT | TGTAACTGCT | GCCCACTGTG | TGAAACTGG | TGTTAAAATT | ACAGTTGTCG |
| 841 | CAGGTGAACA | TAATATTGAG | GAGACAGAAC | ATACAGAGCA | AAAGCGAAAT | GTGATTCGAA |
| 901 | TTATTCCTCA | CCACAACTAC | AATGCAGCTA | TTAATAAGTA | CAACCATGAC | ATTGCCCTTC |
| 961 | TGGAACTGGA | CGAACCCTTA | GTGCTAAACA | GCTACGTTAC | ACCTATTTGC | ATTGCTGACA |
| 1021 | AGGAATACAC | GAACATCTTC | CTCAAATTTG | GATCTGGCTA | TGTAAGTGGC | TGGGGAAGAG |
| 1081 | TCTTCCACAA | AGGGAGATCA | GCTTTAGTTC | TTCAGTACCT | TAGAGTTCCA | CTTGTTGACC |
| 1141 | GAGCCACATG | TCTTCGATCT | ACAAAGTTCA | CCATCTATAA | CAACATGTTC | TGTGCTGGCT |
| 1201 | TCCATGAAGG | AGGTAGAGAT | TCATGTCAAG | GAGATAGTGG | GGGACCCCAT | GTTACTGAAG |
| 1261 | TGGAAGGGAC | CAGTTTCTTA | ACTGGAATTA | TTAGCTGGGG | TGAAGAGTGT | GCAATGAAAG |
| 1321 | GCAAATATGG | AATATATACC | AAGGTATCCC | GGTATGTCAA | CTGGATTAAG | GAAAAAACAA |
| 1381 | AGCTCACTTA | ATGAAAGATG | GATTTCCAAG | GTTAATTCAT | TGGAATTGAA | AATTAACAGG |
| 1441 | GCCTCTCACT | AACTAATCAC | TTTCCCATCT | TTTGTTAGAT | TTGAATATAT | ACATTCTATG |
| 1501 | ATCATTGCTT | TTTCTCTTTA | CAGGGGAGAA | TTTCATATTT | TACCTGAG | |

FIG. 12

```
   1 ATGCAAATAG AGCTCTCCAC CTGCTTCTTT CTGTGCCTTT TGCGATTCTG CTTTAGTGCC
  61 ACCAGAAGAT ACTACCTGGG TGCAGTGGAA CTGTCAGGAA CTGTCATGGG ACTATATGCA AAGTGATCTC
 121 GGTGAGCTGC CTGTGGACGC AAGATTTCCT CCTAGAGTGC CAAAATCTTT TCCATTGAAC
 181 ACCTCAGTCG TGTACAAAAA GACTCTGTTT GTAGAATTCA CGGTTCACCT TTTCAACATC
 241 GCTAAGCCAA GGCCACCCTG GATGGGTCTG CTAGGTCCTA CCATCCAGGC TGAGGTTTAT
 301 GATACAGTGG TCATTACACT TAAGAACATG GCTTCCCATC CTGTCAGTCT TCATGCTGTC
 361 GGTGTATCCT ACTGGAAAGC TTCTGAGGGA GCTGAATATG ATGATCAGAC CAGTCAAAGG
 421 GAGAAAGAAG ATGATAAAGT CTTCCCTGGT GAAGCCATA CATATGTCTG GCAGGTCCTG
 481 AAAGAGAATG GTCCAATGCC CTCTGACCCA CTGTGCCTTA GGAAGCCCTA CTGTGCCTTA
 541 GTGGACCTGG TAAAAGACTT GAATTCAGGC CTCATTGGAG CCCTACTCAT ATGTAGAGAA
 601 GGGAGTCTGG CCAAGGAAAA GACACAGACC TTGCACAAAT TTATACTACT TTTTGCTGTA
 661 TTTGATGAAG GGAAAAAGTTG GCACTCAGAA ACAAAGAACT CCTTGATGCA GGATAGGGAT
 721 GCTGCATCTG CTCGGGCCTG GCCTAAAAATG CACACAGTCA ATGGTTATGT AAACAGTCT
 781 CTGCCAGGTC TGATTGGATG CCACAGGAAA TCAGTCTATT GGCATGTGAT TGGAATGGGC
 841 ACCACTCCTG AAGTGCACTC AATATTCCTC GAAGGTCACA CATTTCTTGT GAGGAACCAT
 901 CGCCAGGCGT CCTTGAAAT CTCGCCAATA ACTTTCCTTA CTGCTCAAAC ACTCTTGATG
 961 GACCTTGGAC AGTTTCTACT GTTTTGTCAT ATCTCTTCCC ACCAACATGA TGGCATGGAA
1021 GCTTATGTCA AAGTAGACAG CTGTCCAGAG GAACCCCAAC TACGAATGAA AAATAATGAA
1081 GAAGCGGAAG ACTATGATGA TGATCTTACT GATCTCGAAA TGGATGTGGT CAGGTTTGAT
1141 GATGACAACT CTCCTTCCTT TATCCAAATT CGCTCAGTTG CCAAGAAGCA TCCTAAAACT
1201 TGGTGACATT ACATTGCTGC TGAAGAGGAG GACTGGGACT ATGCTCCCCTT AGTCCTCGCC
1261 CCCGATGACA GAAGTTATAA AAGTCAATAT TTGAACAATG GCCCTCAGCG GATGGGTAGG
1321 AAGTACAAAA AAGTCCGATT TATGGCATAC ACAGATGAAA CCTTTAAGAC TCGTGAAGCT
1381 ATTCAGCATG AATCAGGAAT CTTGGGACCT TTACTTTATG GGAAGTTGG AGACACACTG
1441 TTGATTATAT TTAAGAATCA AGCAAGCAGA CCATATAACA TCTACCCTCA CGGAATCACT
1501 GATGTCCGTC CTTTGTATTC AAGGAGATTA CCAAAAGGTG TAAAACATT GAAGGATTT
```

RESTRICTION DIGESTION ANALYSIS OF Av1ALH81 DNA

FACTOR VIII ADENOVIRUS VECTORS

DNA and RNA Analyses

High Vector Dose

DNA and RNA Analyses

Low Vector Dose

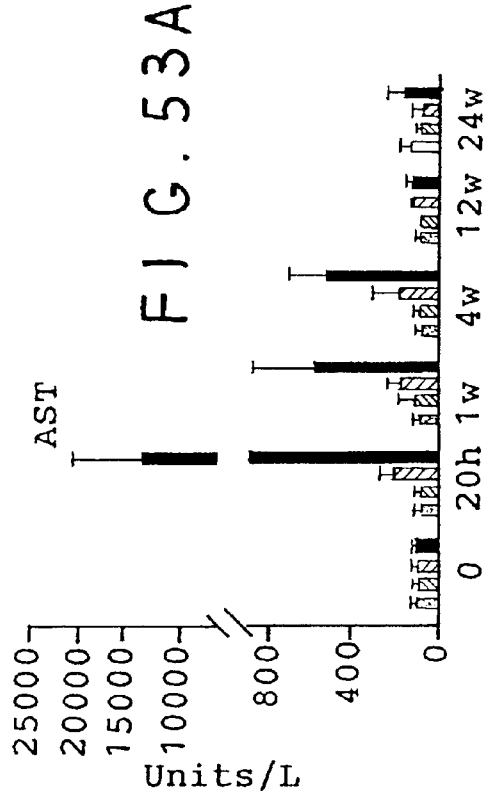
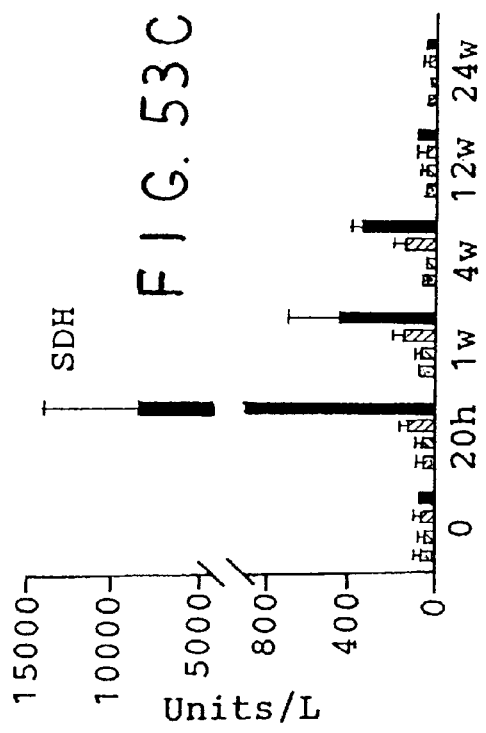
FIG. 53A  FIG. 53B  FIG. 53C  FIG. 53D

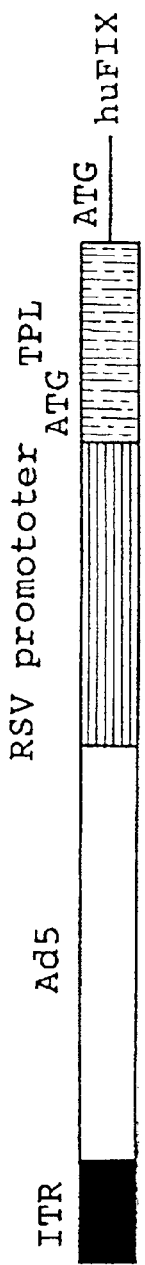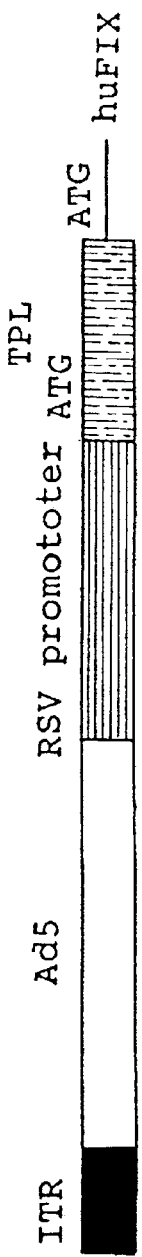
FIG. 60

FIG. 61
Comparison of Av1H9FR, Av1H9F1, and Av1H9F2 in Mice
$1 \times 10^8$
|  | FR | F1 | F2 |
|---|---|---|---|
| Ave. ng/ml | 1430 | 898 | 11423 |
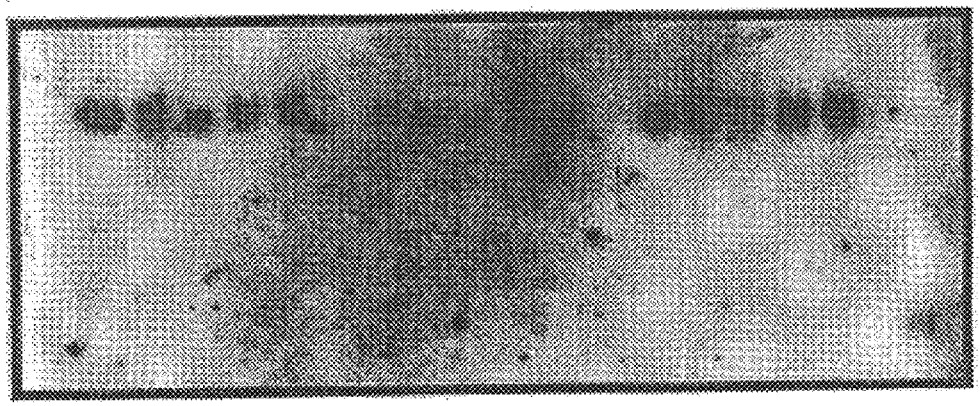
$5 \times 10^7$
|  | FR | F1 | F2 |
|---|---|---|---|
| Ave. ng/ml | 123 | 130 | 1808 |
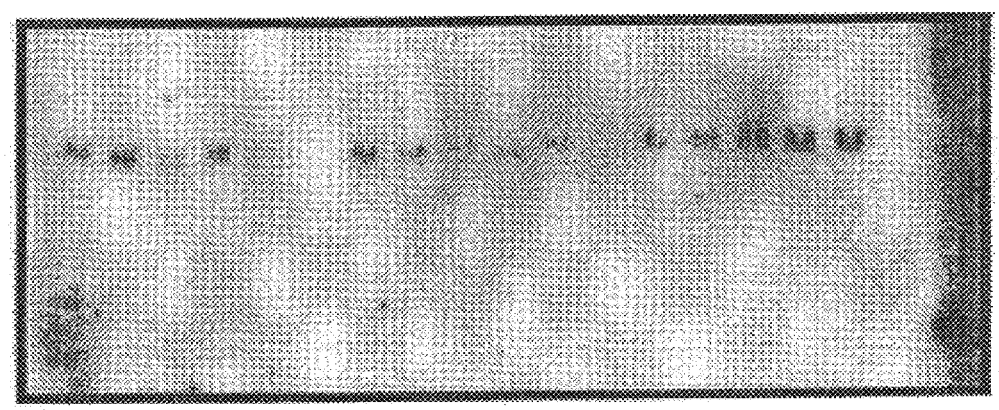

ADENOVIRAL VECTORS FOR ENHANCED GENE EXPRESSION

This is a continuation of U.S. application Ser. No. 08/484,891, filed Jun. 7, 1995, now U.S. Pat. No. 5,935,935, which is a continuation-in-part of U.S. application Ser. No. 08/218,335, filed Mar. 25, 1994, now abandoned, which is a continuation-in-part of U.S. application Ser. No. 08/074,920, filed Jun. 10, 1993, now abandoned.

FIELD OF THE INVENTION

This invention relates to adenoviral vectors. More particularly, this invention relates to adenoviral vectors which may be employed in the treatment of hemophilia.

BACKGROUND OF THE INVENTION

Hemophilias A and B are X-linked, recessive bleeding disorders caused by deficiencies of clotting Factors VIII and IX, respectively. In the United States there are approximately 17,000 patients with hemophilia A and 2,800 with hemophilia B. The clinical presentations for both hemophilias are characterized by episodes of spontaneous and prolonged bleeding. Patients frequently suffer joint bleeds which lead to a disabling arthropathy. Current treatment is directed at stopping the bleeding episodes with intravenous infusions of plasma-derived clotting factors or, for hemophilia A, recombinant Factor VIII. However, therapy is limited by the availability of clotting factors, their short half-lives in vivo, and the high cost of treatment, which can approach 100,000 dollars per year.

Gene therapy offers the promise of a new method of treating hemophilia. Several groups of researchers have conducted research with retroviral vectors containing RNA encoding Factor VIII and Factor IX. Prior to Applicants' invention, virtually every attempt to produce therapeutic levels of these factors in vivo with such vectors, however, has been unsuccessful. The cDNA and the RNA for Factor VIII has been particularly difficult to work with.

Hoeben et al., *J. Biol. Chem,* Vol. 265, pgs 7318–7323 (1990) and Israel et al. *Blood,* Vol. 75, No. 5, pgs. 1074–1080 (Mar. 1, 1990) describe the infection of mouse fibroblasts in vitro with retroviral vectors including DNA (RNA) encoding B-domain deleted human Factor VIII. Although such infected cells were found to express functional human Factor VIII in vitro, the protein was expressed at low levels.

Recently, Hoeben et al., *Human Gene Therapy,* Vol. 4, pgs 179–186 (1993) infected fibroblasts with retroviral vectors including DNA encoding human Factor VIII. These cells then were implanted into immune-deficient mice. Although cells recovered from the implants up to 2 months post-implantation still had the capacity to secrete Factor VIII when regrown in tissue culture, human Factor VIII was not detected in plasma samples of the recipient mice.

Lynch et al., *Human Gene Therapy,* Vol. 4, pgs. 259–272 (1993), describes the transfection of PE501 packaging cells with the plasmid forms of retroviral vectors including human Factor VIII cDNA. The virus was harvested, and used to infect PA317 amphotropic retrovirus packaging cells. The infected cells, however, produced human Factor VIII and virus titer in an amount which was about two orders of magnitude lower than those from similar retroviral vectors containing other cDNAs. Lynch et al. also observed a 100-fold lower accumulation of vector RNAs containing the human Factor VIII sequences in comparison to vectors containing other cDNA sequences.

Lynch et al. also reported the following difficulties in working with Factor VIII. High titer human Factor VIII-containing retroviral vector stocks are difficult to generate, and retroviral vectors containing Factor VIII cDNA sequences tend to rearrange and/or delete portions of the Factor VIII cDNA sequences. In addition, Factor VIII mRNA is inherently unstable. Also, the B-domain deleted Factor-VIII coding region contains a 1.2 kb RNA accumulation inhibitory signal.

Thus, there have been significant problems in working with retroviral approaches to gene therapy with Factor VIII and that only limited expression has been achieved prior to Applicants' invention.

Researchers also have experienced significant difficulties in attempting to achieve therapeutic levels of Factor IX expression with retroviral vectors prior to Applicants' invention.

Palmer et al., *Blood,* Vol. 73, No. 2, pgs. 438–445 (February 1989) discloses the transduction of human skin fibroblasts with retroviral vectors including DNA (RNA) encoding human Factor IX. Such transformed fibroblasts then were given to rats and to nude mice. Although such fibroblasts were found to transiently express human Factor IX in the animal blood in amounts up to 190 ng/ml, this amount is not generally considered to be at a therapeutic level.

Scharfmann et al., *Proc. Nat. Acad. Sci.,* Vol. 88, pgs. 4626–4630 (June 1991) discloses the transduction of mouse fibroblast implants with a retroviral vector including a B-galactosidase gene under the control of the dihydrofolate reductase (DHFR) promoter. Such fibroblasts then were grafted into mice, and expression of the β-galactosidase gene for up to sixty days was obtained. Scharfmann et al. also disclose fibroblasts transduced with canine Factor IX, but they only obtained short-term and non-therapeutic levels of expression.

Dai et al., *Proc. Nat. Acad. Sci.,* Vol. 89, pgs. 10892–10895 (November 1992) discloses the transfection of mouse primary myoblasts with retroviral vectors including canine Factor IX DNA under the control of a mouse muscle creatine kinase enhancer and a human cytomegalovirus promoter. The transfected myoblasts then were injected into the hind legs of mice. Expression of canine Factor IX over a period of 6 months was obtained; however, the steady-state levels of Factor IX secreted into the plasma (10 ng/ml for $10^7$ injected cells) are not sufficient to be of therapeutic value.

Gerrard et al., *Nature Genetics,* Vol. 3, pgs. 180–183 (February 1993), discloses the transfection of primary human keratinocytes with a retroviral vector including a human Factor IX gene under the control of the retroviral LTR. The transformed keratinocytes then were transplanted into nude mice, and human Factor IX was detected in the bloodstream for about 1 week. The amounts of Factor IX, however, were about 2.5 ng/ml, or about 1% of a therapeutic dose.

Kay et al., *Science,* Vol. 262, pgs. 117–119 (Oct. 1, 1993) discloses the direct infusion of retroviral vectors including Factor IX DNA into the portal vasculature of dogs following partial hepatectomy. The animals expressed low levels of canine Factor IX for more than 5 months. Although such expression of Factor IX resulted in reductions of whole blood clotting and partial thromboplastin times of the treated animals, the authors stated that increased levels of Factor IX must first be achieved before the technique could be applied to humans.

Zhou et al., *Science in China,* Vol. 36, No. 9, pgs. 33–41 (September 1993) discloses the transfection of rabbit skin fibroblasts with retroviral vectors including DNA encoding human Factor IX. The fibroblasts then were implanted into rabbits as autografts or allografts. Expression of the human Factor IX was maintained in the rabbits for over 10 months. Factor IX levels in the rabbit plasma of up to 480 ng/ml were claimed to have been achieved; however, the assay used to measure Factor IX employed an anti-rabbit antibody that had the potential of generating false positive results.

Lu et al., *Science in China,* Vol. 36, No. 11, pgs. 1341–1351 (November 1993) and Hsueh et al., *Human Gene Therapy,* Vol. 3, pgs. 543–552 (1992) discloses a human gene therapy trial in which human skin fibroblasts were taken from two hemophiliac patients, and transfected with retroviral vectors including DNA encoding human Factor IX. The cells then were pooled and embedded in a collagen mixture, and the cells then were injected into the patients. In one patient, the concentration of human Factor IX increased from 71 ng/ml to 220 ng/ml, with a maximum level of 245 ng/ml. The clotting activity of this patient increased from 2.9% to 6.3% of normal. In the other patient, the plasma level of Factor IX increased from 130 ng/ml to 250 ng/ml, and was maintained at a level of 220 ng/ml for 5½ months; however, the clotting activity has not increased. Lack of pretreatment Factor IX data on these patients makes it difficult to interpret the small increases in Factor IX seen in treatment.

The conclusion to be drawn from scientific literature at the time of Applicants' invention, on the attempts to use retroviruses in gene therapy for hemophilia A and hemophilia B is that, in spite of a very concerted effort and numerous attempts, by and large the field has failed to produce retroviral vectors that can be used to achieve therapeutic levels of expression of human Factor VIII or human Factor IX in vivo. Working with Factor VIII has been especially difficult, and the results have been unsatisfactory. The experimental strategies described above are laborious and clinically invasive.

Adenoviral vectors offer another approach to gene therapy. Adenovirus genomes are linear, double-stranded DNA molecules of approximately 36 kilobase pairs. Each extremity of the viral genome has a short sequence known as the inverted terminal repeat (or ITR), which is necessary for viral replication. The well-characterized molecular genetics of adenovirus render it an advantageous vector for gene transfer. Portions of the viral genome can be substituted with DNA of foreign origin. In addition, recombinant adenoviruses are structurally stable and no rearranged viruses are observed after extensive amplification.

Recombinant adenoviruses have been used as efficient vectors for gene transfer into a number of cell types. There are several reports of hepatocyte transduction: Jaffe et al., *Nature Genetics,* Vol. 1, pgs. 372–378 (1992) (alpha-1-antitrypsin); Li et al., *Human Gene Therapy,* Vol. 4, pgs. 403–409 (1993) (beta-galactosidase); Stratford-Perricaudet et al., *Human Gene Therapy,* Vol. 1, pgs. 241–256 (1990) (ornithine transcarbamylase); Smith, et al., *Nature Genetics,* Vol. 5, pgs. 397–402 (1993) (Factor IX); and *J. Am. Med. Assoc.,* Vol. 269, No. 7, pg. 838 (Feb. 17, 1993) (marker protein).

Because Factor VIII is synthesized largely in hepatocytes (Kelly et al. *Br. J. Haemat.,* Vol. 56, pgs. 535–543 (1984); Wion et al., *Nature,* Vol. 317, pgs. 726–729 (1985); Zelechovska et al. *Nature,* Vol. 317, pgs. 729–732 (1985)), transduction of hepatocytes with a Factor VIII—containing recombinant adenovirus, resulting in the expression of Factor VIII protein in vivo, may be an effective gene therapy-based treatment for hemophilia A.

The inventors have discovered how to produce high titer, stable, adenoviral vectors that produce therapeutic levels of clotting factors when administered to an animal host. These vectors mediate gene transfer in vivo and will enable treatment protocols to be much less laborious and invasive than those previously described.

BRIEF DESCRIPTION OF THE DRAWINGS

The invention will now be described with respect to the drawings, wherein:

FIG. 6 is the human Factor IX cDNA sequence necleotides 661–1548 of SEQ ID NO:6;

FIG. 12 is the sequence of B-domain deleted human Factor VIII cDNA nucleotides 1–1560 of SEQ ID NO:7;

FIGS. 53A, 53B, 53C and 53D are graphs of the amounts of aspartate aminotransferase, alanine aminotransferase, sorbitol dehydrogenase, and alkaline phosphatase, respectively, which are present in plasma samples of mice which received $4 \times 10^9$ pfu or $5 \times 10^8$ pfu of Av1ALAPH81, or were uninjected;

FIG. 60 is a schematic of adenoviral vectors Av1H9FR, Av1H9F1, and Av1H9F2; and

FIG. 61 is a Southern blot analysis of DNA from the livers of mice which were given $5 \times 10^7$ pfu or $1 \times 10^8$ pfu of Av1H9FR, Av1H9F1, or Av1H9F2, with average values of plasma human Factor IX from each cohort of mice.

DETAILED DESCRIPTION OF THE INVENTION

Figure 1:
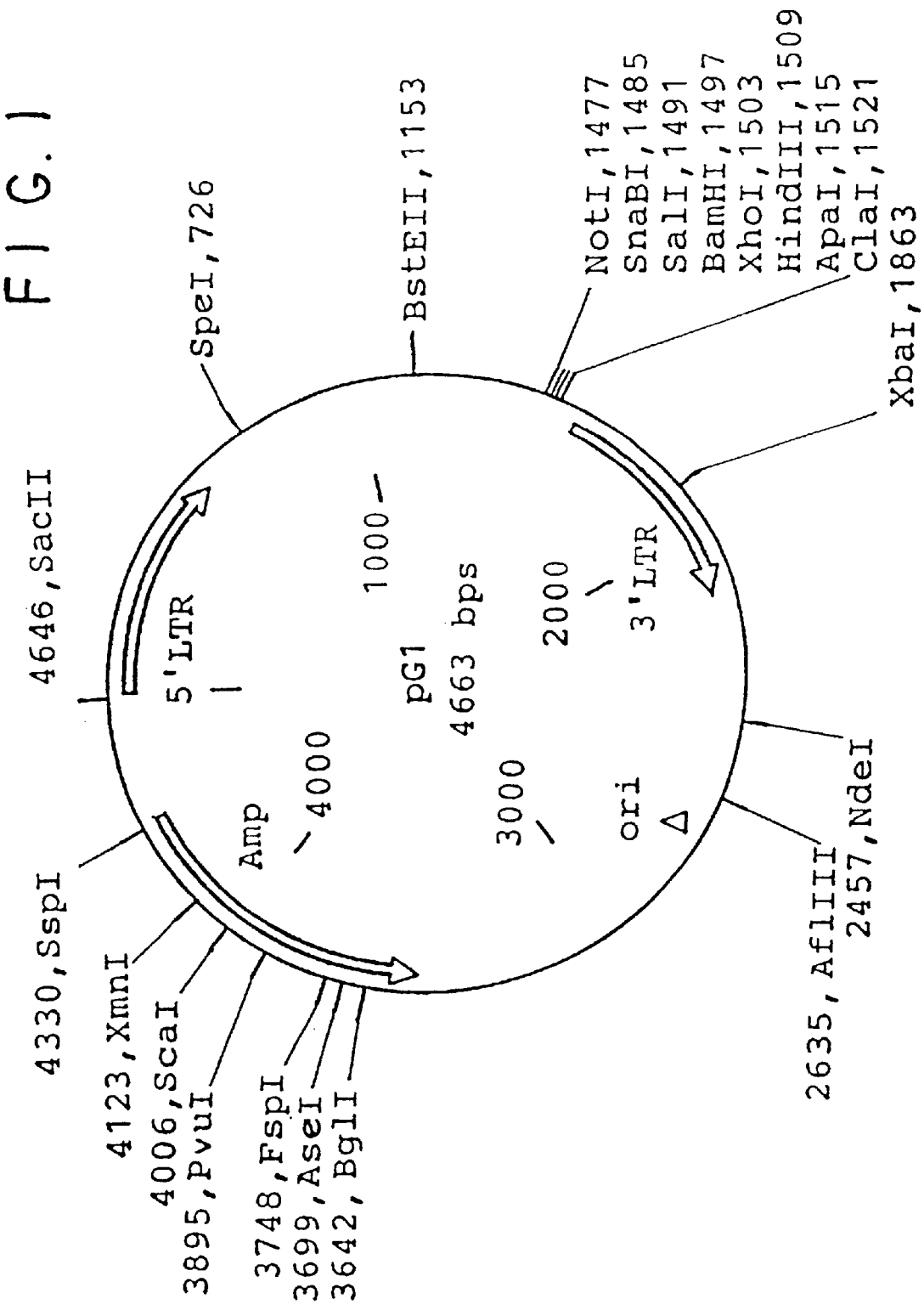
FIG. 1 is a map of plasmid pG1.

In accordance with an aspect of the present invention, there is provided an adenoviral vector including at least one DNA sequence encoding a clotting factor.

The term "DNA sequence encoding a clotting factor" as used herein means DNA which encodes a full-length clotting factor or a fragment, derivative, or analogue of a clotting factor, i.e., such DNA may be a full-length gene encoding a full-length clotting factor, or a truncated gene, or a mutated gene encoding a fragment or derivative or analogue of such clotting factor which has clotting factor activity. The term "DNA sequence" refers generally to a polydeoxyribonucleotide molecule and more specifically to a linear series of deoxyribonucleotides connected one to the other by phosphodiester bonds between the 3' and 5' carbons of the adjacent pentoses.

In one embodiment, the DNA sequence encodes Factor VIII or a fragment, derivative, or analogue thereof having Factor VIII clotting activity. In another embodiment, the DNA sequence encodes Factor IX or a fragment, derivative, or analogue thereof having Factor IX clotting activity.

The DNA sequence encoding human Factor IX is shown and described in U.S. Pat. No. 4,994,371 issued Feb. 19, 1991 to Davie et al. and European Patent No. EP 0 107 278

B1 (publication of grant Nov. 15, 1989) to National Research Development Corporation. DNA sequences encoding Factor VIII and fragments or derivatives thereof are shown and described in U.S. Pat. No. 4,757,006 issued Jul. 12, 1988 to Toole, Jr. et al.; U.S. No. 4,868,112 issued Sep. 19, 1989 to Toole, Jr.; U.S. No. 5,045,455 issued Sep. 3, 1991 to Kuo et al; U.S. No. 5,004,804 issued Apr. 2, 1991 to Kuo et al.; U.S. No. 5,112,950 issued May 12, 1992 to Meulien et al.; and U.S. No. 5,149,637 issued Sep. 22, 1992 to Scandella et al.

The inventors have found that, by infecting host cells in vivo with adenoviral vectors including at least one DNA sequence encoding a clotting factor, one is able to achieve expression, in vivo, of the clotting factor, or fragment or derivative or analogue of such clotting factor having clotting factor activity, at effective therapeutic levels. In general, such effective therapeutic levels are about 5% or greater of the normal level of the clotting factor (*N. Engl. J. Med.,* Vol. 328, No. 7, pgs. 453–459 (Feb. 18, 1993); *Blood,* Vol. 74, No. 1, pgs. 207–212 (July 1989)). Such levels are, in general, for Factor VIII, about 10 ng/ml or greater, and for Factor IX are about 250 ng/ml or greater.

The DNA sequence encoding a clotting factor is under the control of a suitable promoter. Suitable promoters which may be employed include, but are not limited to, adenoviral promoters, such as the adenoviral major late promoter; or heterologous promoters, such as the cytomegalovirus (CMV) promoter; the respiratory syncytial virus promoter; the Rous Sarcoma Virus (RSV) promoter; the albumin promoter; inducible promoters, such as the Mouse Mammary Tumor Virus (MMTV) promoter; the metallothionein promoter; heat shock promoters; the α-1-antitrypsin promoter; the hepatitis B surface antigen promoter; the transferrin promoter; the apolipoprotein A-1 promoter; the Factor VIII promoter; and the Factor IX promoter. It is to be understood, however, that the scope of the present invention is not to be limited to specific promoters.

In one embodiment, when the DNA sequence encodes Factor VIII or a fragment, derivative, or analogue thereof, the promoter controlling the DNA sequence is preferably a tissue-specific promoter, such as, for example, the mouse albumin promoter, which is active in liver cells. Although the scope of this embodiment is not intended to be limited to any theoretical reasoning, the inventors believe that, by employing a tissue-specific promoter, possible Factor VIII toxicity to the producer cells is avoided.

When one employs a mouse albumin promoter, which is active in liver cells, the adenoviral vectors are preferably grown in cells other than liver cells. When the generated adenoviral vectors are to be administered to a host, such vectors are administered to a host by means known to those skilled in the art, whereby the vectors will travel to and infect liver cells. The infected liver cells then will express Factor VIII in therapeutic amounts. Factor VIII is not toxic to liver cells and thus will continue to be expressed at therapeutic levels.

In yet another embodiment, when the DNA sequence encodes Factor IX or a fragment, derivative, or analogue thereof, the promoter controlling the DNA sequence is preferably a strong promoter that is not tissue-specific, such as, for example, the Rous Sarcoma Virus promoter. Because it is believed that Factor IX is not toxic to most cells, the adenoviral vectors may be grown in any cell type, and may be administered to a patient in an effective therapeutic amount, whereby the adenoviral vectors will travel to and infect cells such as liver cells, for example, whereby the Factor IX will be expressed in therapeutic amounts.

Several reports have revealed that, in transgenic mice, enhanced expression of cDNA's can be obtained by the incorporation of 5' and 3' untranslated regions as well as introns (Choo et al. *Nucl. Acids Res.,* Vol. 15, pgs. 881–884 (1987); Brinster et al. *PNAS,* Vol. 85, pgs 836–840 (1988); Jallat et al. *EMBO J.,* Vol. 9, No. 10, pgs. 3295–3301 (1990); and Choi et al. *Mol. Cell. Biol.,* Vol. 11, pgs. 3070–3074 (1991)). The inclusion of genomic elements does not always result in improved expression. Furthermore, the effectiveness of genomic elements in improving expression of exogenous genes incorporated into an adenoviral vector backbone has not been demonstrated previously.

In one embodiment, the DNA sequence encoding a clotting factor also may include introns and other genomic elements to enhance expression. The term "genomic element," as used herein, means a sequence of nucleotides in a naturally occurring gene that is not normally incorporated into the cDNA, and which is not part of the adenoviral genome. Such genomic elements which may be included in the vector include, but are not limited to, introns, the 5' untranslated region, and the 3' untranslated region of the gene encoding the clotting factor, or portions of such 5' and 3' untranslated regions and introns. Examples of introns which may be employed include, but are not limited to, any of the seven introns of the Factor IX gene, or portions thereof (*EMBO J.,* Vol. 9, No. 10, pgs. 3295–3301 (1990)); or any of the twenty-five introns of the Factor VIII gene (Gitschier, *Nature,* 312:326–330 (1984)), or portions thereof; or the first exon and intron of the apolipoprotein A-1 gene.

When the DNA sequence encodes Factor IX or a fragment, derivative, or analogue thereof, the vector may, in one embodiment, further include the full 3' untranslated region of the Factor IX DNA sequence. In another embodiment, the vector may further include the full 5' untranslated region and a centrally truncated first intron. In yet another embodiment, the vector may further include the full 3' untranslated region, the full 5' untranslated region, and a centrally truncated first intron. Most preferably, the vector contains all of these elements. In a further embodiment, the vector may further include the full 7th intron of the Factor IX gene.

When such elements are included in the vector, improved levels of expression of Factor IX are obtained. Although the scope of the present invention is not intended to be limited to any theoretical reasoning, such improved expression may be due to (i) the incorporation of enhancers in the genomic sequences; (ii) stabilization of the mRNA; (iii) improved processing and transport of the mRNA to the cytoplasm; and/or (iv) improved polyadenylation.

In another embodiment, the first exon and first intron of the apolipoprotein A-1 gene may be employed, if desired, with the apolipoprotein A-1 gene promoter. (*PNAS,* Vol. 80, pgs. 6147–6151 (October 1983); *J. Biol. Chem.,* Vol. 266, No. 27, pgs. 18045–18050 (September 1991)). The above-mentioned introns and/or exons also may be used in combination with the 5' untranslated region and/or the 3' untranslated region of the gene encoding the clotting factor.

In yet another embodiment, the above-mentioned introns and/or exons and/or promoter of the apolipoprotein A-1 gene may be used in combination with the apolipoprotein A-1 5' untranslated region and/or the apolipoprotein A-1 3' untranslated region and poly A signal. In one embodiment, the above-mentioned introns and/or exons and/or promoter of the apolipoprotein A-1 gene are used in combination with the apolipoprotein A-1 3' untranslated region and poly A signal.

In a further embodiment, when the DNA sequence encodes Factor VIII or a fragment, derivative, or analogue thereof, the above-mentioned introns and/or exons, and/or promoter of the apolipoprotein A-1 gene may be used in combination with the 5' untranslated region and/or 3' untranslated region and poly A signal of the human Factor IX gene. In one embodiment, the above-mentioned introns and/or exons and/or promoter of the apolipoprotein A-1 gene are used in combination with the 3' untranslated region and poly A signal of the human Factor IX gene.

In one preferred embodiment, the apolipoprotein A-1 promoter may be employed, alone or in combination with the first exon and/or first intron of the apolipoprotein A-1 gene, in combination with the Factor VIII gene.

The adenoviral vector which is employed may, in one embodiment, be an adenoviral vector which includes essentially the complete adenoviral genome (Shenk et al., *Curr. Top. Microbiol. Immunol.*, 111(3): 1–39 (1984). Alternatively, the adenoviral vector may be a modified adenoviral vector in which at least a portion of the adenoviral genome has been deleted.

In the preferred embodiment, the adenoviral vector comprises an adenoviral 5' ITR; an adenoviral 3' ITR; an adenoviral encapsidation signal; at least one DNA sequence encoding a clotting factor; and a promoter controlling the at least one DNA sequence encoding a clotting factor. The vector is free of at least the majority of adenoviral E1 and E3 DNA sequences, but is not free of all of the E2 and E4 DNA sequences, and DNA sequences encoding adenoviral proteins promoted by the adenoviral major late promoter.

In one embodiment, the vector also is free of at least a portion of at least one DNA sequence selected from the group consisting of the E2 and E4 DNA sequences.

In another embodiment, the vector is free of at least the majority of the adenoviral E1 and E3 DNA sequences, and is free of a portion of the other of the E2 and E4 DNA sequences.

In still another embodiment, the gene in the E2a region that encodes the 72 kilodalton binding protein is mutated to produce a temperature sensitive protein that is active at 32° C., the temperature at which the viral particles are produced. This temperature sensitive mutant is described in Ensinger et al., *J. Virology,* 10:328–339 (1972), Van der Vliet et al., *J. Virology,* 15:348–354 (1975), and Friefeld et al., *Virology,* 124:380–389 (1983).

Such a vector, in a preferred embodiment, is constructed first by constructing, according to standard techniques, a shuttle plasmid which contains, beginning at the 5' end, the "critical left end elements," which include an adenoviral 5' ITR, an adenoviral encapsidation signal, and an E1a enhancer sequence; a promoter (which may be an adenoviral promoter or a foreign promoter); a multiple cloning site (which may be as hereinabove described); a poly A signal; and a DNA segment which corresponds to a segment of the adenoviral genome. The vector also may contain a tripartite leader sequence. The DNA segment corresponding to the adenoviral genome serves as a substrate for homologous recombination with a modified or mutated adenovirus, and such sequence may encompass, for example, a segment of the adenovirus 5 genome no longer than from base 3329 to base 6246 of the genome. The plasmid may also include a selectable marker and an origin of replication. The origin of replication may be a bacterial origin of replication. Representative examples of such shuttle plasmids include pAVS6, shown in FIG. 5. A desired DNA sequence encoding a clotting factor may then be inserted into the multiple cloning site to produce a plasmid vector.

This construct is then used to produce an adenoviral vector. Homologous recombination is effected with a modified or mutated adenovirus in which at least the majority of the E1 and E3 adenoviral DNA sequences have been deleted. Such homologous recombination may be effected through co-transfection of the plasmid vector and the modified adenovirus into a helper cell line, such as 293 cells, by $CaPO_4$ precipitation. Upon such homologous recombination, a recombinant adenoviral vector is formed that includes DNA sequences derived from the shuttle plasmid between the Not I site and the homologous recombination fragment, and DNA derived from the E1 and E3 deleted adenovirus between the homologous recombination fragment and the 3' ITR.

In one embodiment, the homologous recombination fragment overlaps with nucleotides 3329 to 6246 of the adenovirus 5 (ATCC VR-5) genome.

Through such homologous recombination, a vector is formed which includes an adenoviral 5' ITR, an adenoviral encapsidation signal; an E1a enhancer sequence; a promoter; at least one DNA sequence encoding a clotting factor; a poly A signal; adenoviral DNA free of at least the majority of the E1 and E3 adenoviral DNA sequences; and an adenoviral 3' ITR. The vector also may include a tripartite leader sequence. In one embodiment, the tripartite leader sequence is deleted from the adenoviral vector, or the tripartite leader sequence contains one or more mutations such that a polypeptide encoded by such tripartite leader sequence is not expressed. Applicants have found that, by deleting or mutating the tripartite leader sequence of the adenoviral vector, one may obtain improved expression of the clotting factor. The vector may then be transfected into a helper cell line, such as the 293 helper cell line (ATCC No. CRL1573), which will include the E1a and E1b DNA sequences, which are necessary for viral replication, and to generate infectious adenoviral particles. Transfection may take place by electroporation, calcium phosphate precipitation, microinjection, or through proteoliposomes.

The cloning vector hereinabove described may include a multiple cloning site to facilitate the insertion of the at least one DNA sequence encoding a clotting factor into the cloning vector. In general, the multiple cloning site includes "rare" restriction enzyme sites; i.e., sites which are found in eukaryotic genes at a frequency of from about one in every 10,000 to about one in every 100,000 base pairs. An appropriate vector in accordance with the present invention is thus formed by cutting the cloning vector by standard techniques at appropriate restriction sites in the multiple cloning site, and then ligating the DNA sequence encoding a clotting factor into the cloning vector.

The infectious viral particles (i.e., the adenoviral vector) are transduced into eukaryotic cells, such as hepatocytes, whereby the at least one DNA sequence encoding a clotting factor is expressed by the eukaryotic cells in a host.

The vector, consisting of infectious, but replication-defective, viral particles, which contain at least one DNA sequence encoding a clotting factor, is administered in an amount effective to treat hemophilia in a host. In one embodiment, the vector particles may be administered in an amount of from 1 plaque forming unit (pfu) to about $10^{14}$ plaque forming units, preferably from about $1 \times 10^6$ plaque forming units to about $1 \times 10^{13}$ plaque forming units and more preferably from about $1 \times 10^8$ plaque forming units per kg to about $2 \times 10^{10}$ plaque forming units per kg, and most preferably from about $1 \times 10^8$ pfu/kg to about $1 \times 10^{10}$ pfu/kg. The host may be a human or non-human animal host. The preferred non-human animal host is a mammal, most preferably a dog or a non-human primate.

Preferably, the infectious vector particles are administered systemically, such as, for example, by intravenous administration (such as, for example, via peripheral vein injection) or administered via the portal vein, to the bile duct, intramuscularly, intraperitoneally, or intranasally.

The vector particles may be administered in combination with a pharmaceutically acceptable carrier suitable for administration to a patient. The carrier may be a liquid carrier (for example, a saline solution), or a solid carrier, such as, for example, mirocarrier beads.

As hereinabove stated, the inventors have found that the incorporation of genomic elements into the adenoviral vector provides for enhanced expression of the DNA sequence encoding a clotting factor. Thus, in accordance with another aspect of the present invention, there is provided an adenoviral vector including at least one DNA sequence encoding a heterologous protein, and at least one genomic element affecting the expression of such DNA sequence. The term "genomic element" is used as previously defined. Such genomic elements include, but are not limited to, introns, the 5' untranslated region, and the 3' untranslated region, and portions of said introns and 3' and 5' untranslated regions. The adenoviral vector may be as hereinabove described.

The DNA sequence encoding a heterologous protein may be a DNA sequence which encodes at least one therapeutic agent. The term "therapeutic" is used in a generic sense and includes treating agents, prophylactic agents, and replacement agents.

DNA sequences encoding therapeutic agents which may be placed into the adenoviral vector include, but are not limited to, DNA encoding Factor VIII and Factor IX as hereinabove described; DNA encoding cytokines; DNA sequences encoding tumor necrosis factor (TNF) genes, such as TNF-α; genes encoding interferons such as Interferon-α, Interferon-β, and Interferon-γ; genes encoding interleukins such as IL-1, IL-1β, and Interleukins 2 through 14; genes encoding GM-CSF; genes encoding adenosine deaminase, or ADA; genes which encode cellular growth factors, such as lymphokines, which are growth factors for lymphocytes; genes encoding soluble CD4; T-cell receptors; the LDL receptor, ApoE, ApoC, ApoAI and other genes involved in cholesterol transport and metabolism; the alpha-1 antitrypsin (α1AT) gene, the ornithine transcarbamylase (OTC) gene, the CFTR gene, the insulin gene, viral thymidine kinase genes, such as the Herpes Simplex Virus thymidine kinase gene, the cytomegalovirus virus thymidine kinase gene, and the varicella-zoster virus thymidine kinase gene; Fc receptors for antigen-binding domains of antibodies, and antisense sequences which inihibit viral replication, such as antisense sequences which inhibit replication of hepatitis B or hepatitis non-A non-B virus.

Promoters which control the DNA sequence may be selected from those hereinabove described.

In one embodiment, the genomic element and the DNA sequence encoding a heterologous protein are part of the same endogenous gene. For example, the adenoviral vector may include DNA encoding Factor IX and a Factor IX genomic element(s). In another embodiment, the DNA sequence encoding a heterologous protein and the genomic element are taken from different endogenous genes. For example, the adenoviral vector may include DNA encoding Factor VIII and Factor IX genomic elements.

In yet another embodiment, an adenoviral vector may be constructed wherein the adenoviral vector includes DNA encoding a heterologous protein and at least one genomic element(s) from the same endogenous gene. The DNA encoding a heterologous protein may be modified such that at least one exon normally present in the DNA encoding the heterologous protein is removed and replaced with one or more exons present in another gene.

Although the scope of this aspect of the present invention is not to be limited to any theoretical reasoning, Applicants believe that, by the inclusion of at least one genomic element in an adenoviral vector including at least one DNA sequence encoding a heterologous protein, one is able to approximate endogenous transcription, RNA processing, and translation of the DNA sequence encoding a heterologous protein, thereby providing for increased expression of the heterologous protein.

The invention will now be described with respect to the following examples; however, the scope of the present invention is not to be limited thereby.

EXAMPLE 1

Construction of an Adenoviral Vector Including a Factor IX Gene

Figure 2:
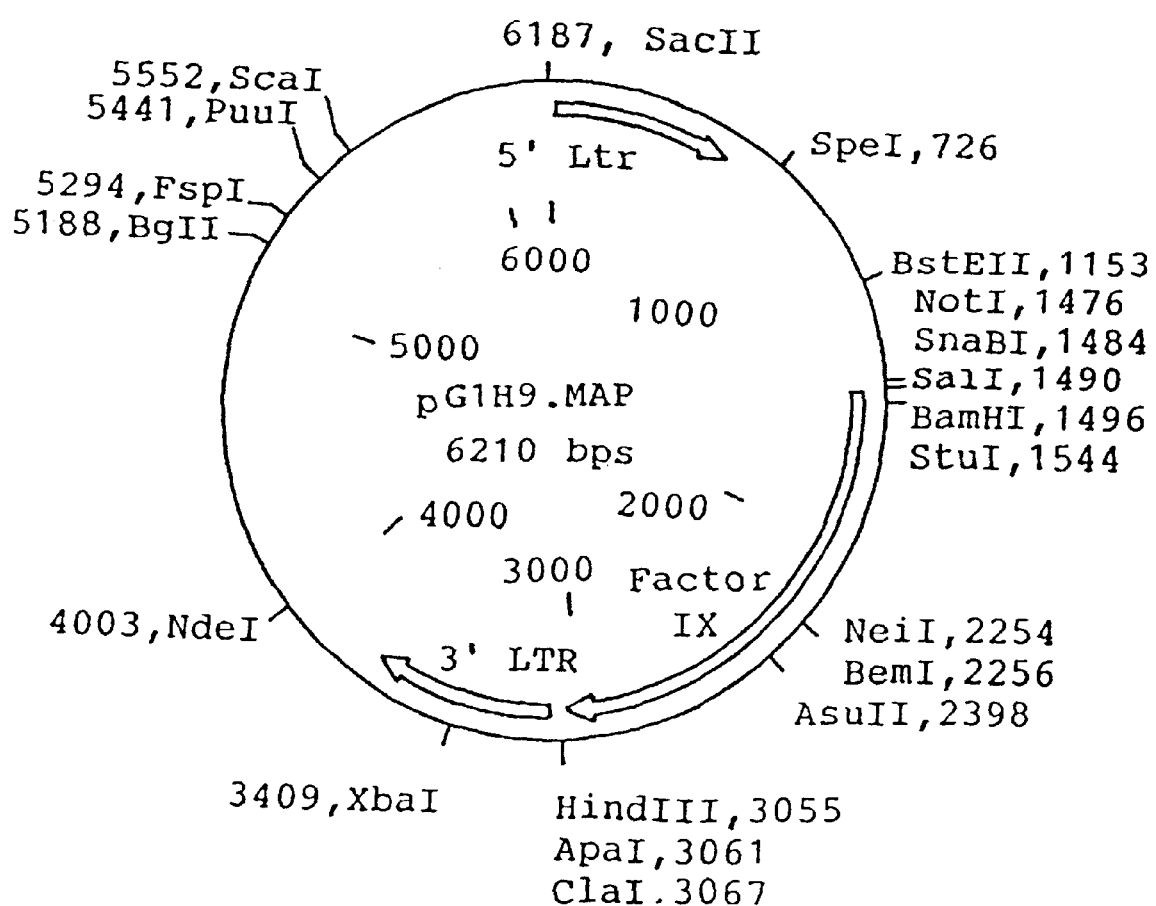
FIG. 2 is a map of plasmid pG1H9.

A. Construction of pG1H9 pG1 (FIG. 1), which is a retroviral plasmid vector including a 5' LTR derived from Moloney Sarcoma Virus, a multiple cloning site, and a 3' LTR from Moloney Murine Leukemia Virus, and is described in PCT Application No. WO91/10728, published Jul. 25, 1991, was cut with BamHI and HindIII. pLIXSN (Palmer et al, *Blood*, Vol. 73, No. 2, pgs. 438–445 (February 1989)), which contains a Factor IX gene, an SV40 promoter, and a neo$^R$gene, was also cut with BamHI and HindIII. The resulting BamHI-HindIII fragment, which contains the Factor IX gene, was then ligated to the BamHI-HindIII digested pG1 to form pG1H9. (FIG. 2). The Factor IX gene could also have been obtained according to the procedures disclosed in U.S. Pat. No. 4,994,371.

Figure 3:
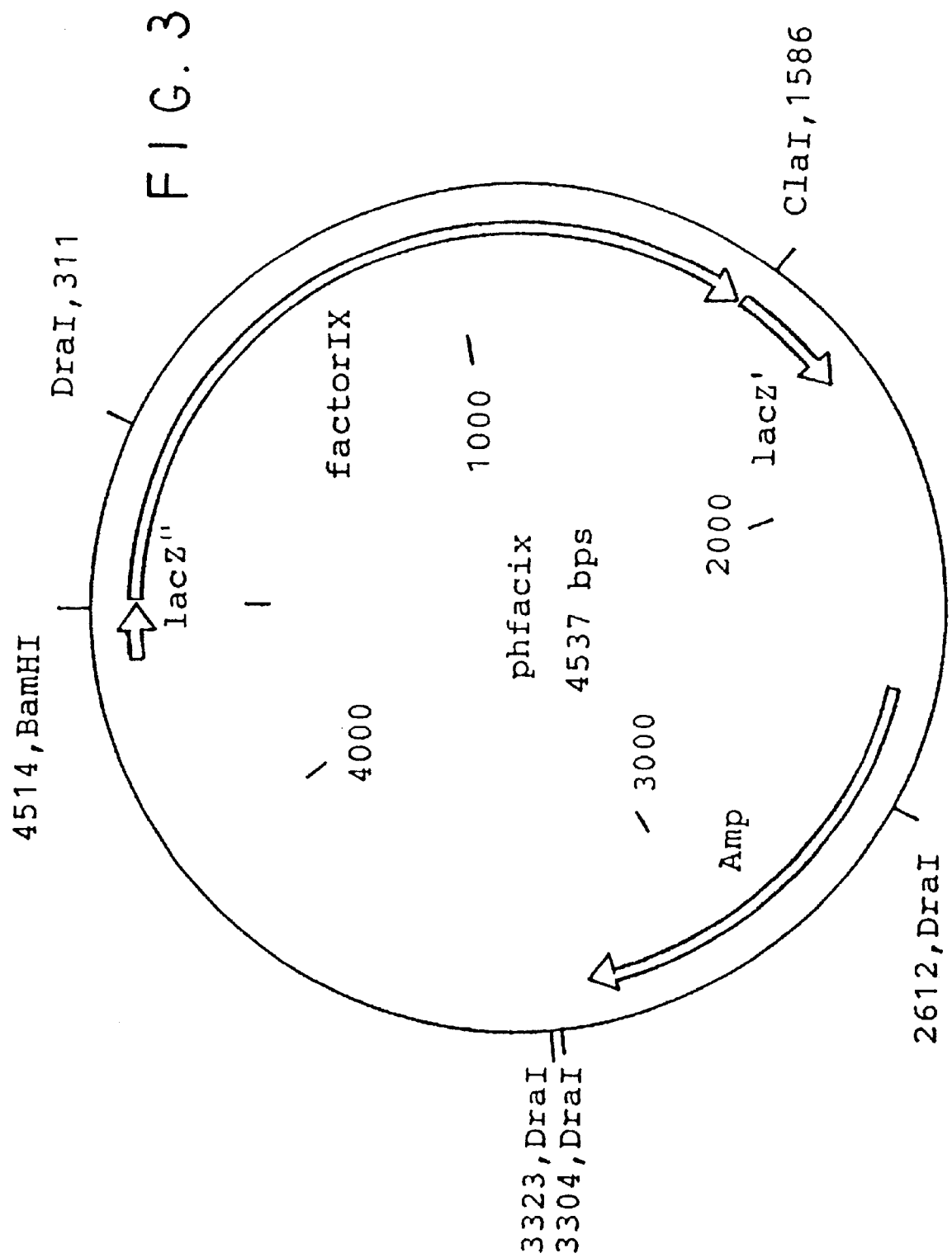
FIG. 3 is a map of plasmid phfacIX.
Figure 4:
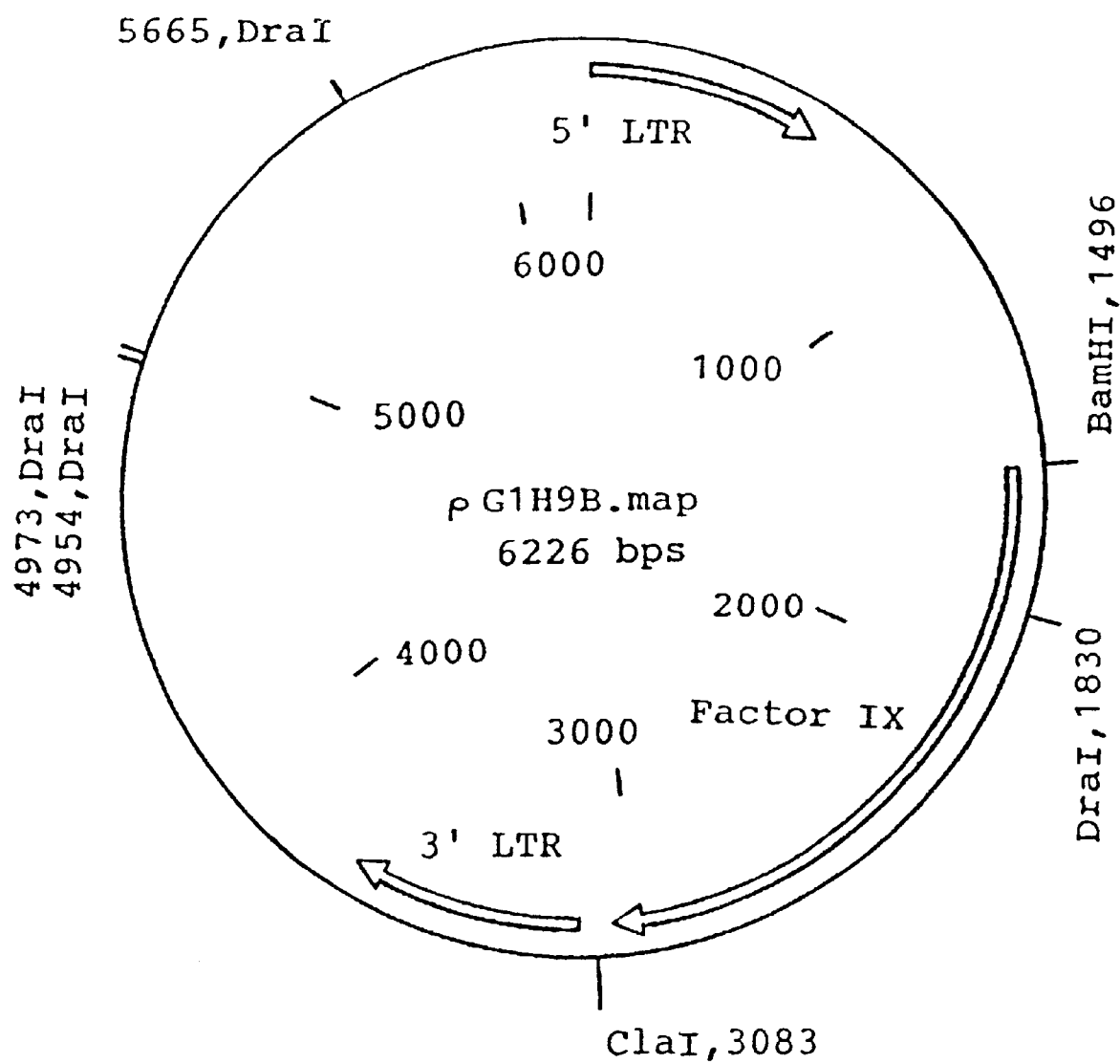
FIG. 4 is a map of plasmid pG1H9B.

B. Construction of pG1H9B pG1H9B (FIG. 4) was constructed so that the 5' portion of the human Factor IX cDNA starting at the first ATG is identical to the natural 5' human Factor IX sequence. Such is not the case for pG1H9 because of an inversion in the DNA sequence.

pG1H9B was constructed as follows. First, a cDNA clone of human Factor IX was generated by PCR amplification of human liver cDNA followed by subcloning into the plasmid pBluescript SK-(Stratagene, La Jolla, Calif.). The resulting plasmid was designated phfacIX (FIG. 3). The 5' end of the Factor IX sequence in this plasmid was then used to replace the 5' end of the Factor IX sequence in G1H9. phfacIX then was cut with BamHI and DraI, and the 334 bp fragment corresponding to the 5' end of the Factor IX cDNA was isolated. pG1H9 was cut with DraI and ClaI and the 1253 bp fragment encoding the 3' end of the Factor IX cDNA was isolated. The two isolated DNA fragments encoding Factor IX cDNA were ligated into the pG1H9 backbone which had been cut with BamHI and ClaI to generate pG1H9B (FIG. 4).

C. Construction of pAVS6

Figure 5:
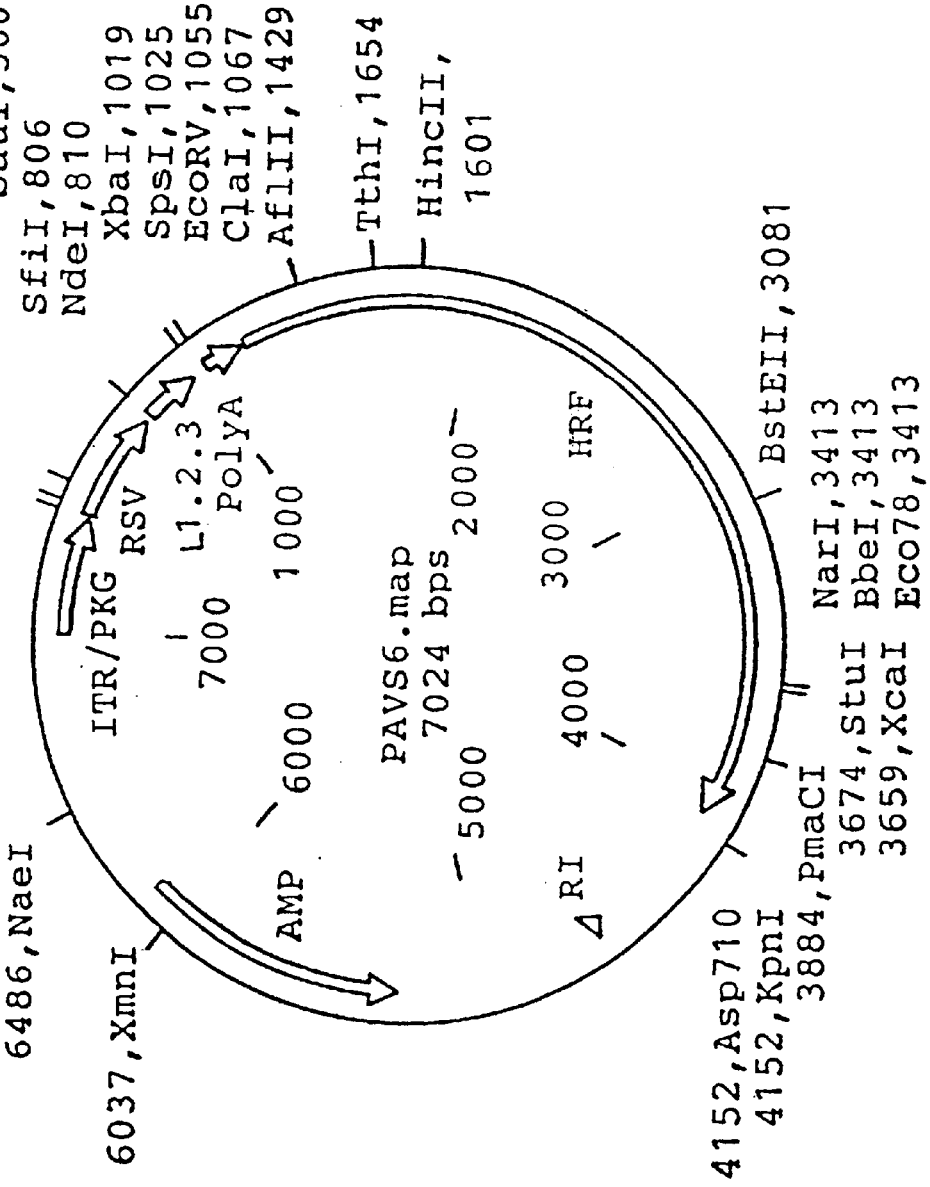
FIG. 5 is a map of pAvS6.

The adenoviral construction shuttle plasmid pAvS6 (FIG. 5, and also described in PCT Application Nos. WO94/23582, published Oct. 27, 1994, and WO95/09654, published Apr. 13, 1995), was constructed in several steps using standard cloning techniques including polymerase chain reaction based cloning techniques. First, the 2913 bp BglII, HindIII fragment was removed from Ad-dl327 and inserted as a blunt fragment into the XhoI site of pBluescript II KS-(Stratagene, La Jolla, Calif.).

Ad-dl327 is identical to adenovirus 5 except that an XbaI fragment including bases 28591 to 30474 (or map units 78.5 to 84.7) of the Adenovirus 5 genome, and which is located in the E3 region, has been deleted. The E3 deletion in Ad-dl327 is similar to the E3 deletion in Ad-dl324, which is described in Thimmapaya et al., *Cell*, Vol. 31, pg. 543 (1983). The complete Adenovirus 5 genome is registered as Genbank accession #M73260, incorporated herein by reference, and the virus is available from the American Type Culture Collection, Rockville, Md. U.S.A. under accession number VR-5.

Ad-dl327 was constructed by routine methods from Adenovirus 5 (Ad5). The method is outlined briefly as follows and previously described by Jones and Shenk, *Cell* 13:181–188, (1978). Ad5 DNA is isolated by proteolytic digestion of the virion and partially cleaved with Xba 1 restriction endonuclease. The Xba 1 fragments are then reassembled by ligation as a mixture of fragments. This results in some ligated genomes with a sequence similar to Ad5, except excluding sequences 28591 bp to 30474 bp. This DNA is then transfected into suitable cells (e.g. KB cells, HeLa cells, 293 cells) and overlaid with soft agar to allow plaque formation. Individual plaques are then isolated, amplified, and screened for the absence of the 1878 bp E3 region Xba 1 fragment.

The orientation of this fragment was such that the BglII site was nearest the T7 RNA polymerase site of pBluescrpt II KS-and the HindIII site was nearest the T3 RNA polymerase site of pBluescript II KS⁻. This plasmid was designated pHR.

Second, the ITR, encapsidation signal, Rous Sarcoma Virus promoter, the adenoviral tripartite leader (TPL) sequence and linking sequences were assembled as a block using PCR amplification. The ITR and encapsidation signal (sequences 1–92 of Ad-dl327 [identical to sequences from Ad5, Genbank accession #M73260] incorporated herein by reference) were amplified (amplification 1) together from Ad-dl327 using primers containing NotI or AscI restriction sites. The Rous Sarcoma Virus LTR promoter was amplified (amplification 2) from the plasmid pRC/RSV (sequences 209 to 605; Invitrogen, San Diego, Calif.) using primers containing an AscI site and an SfiI site. DNA products from amplifications 1 and 2 were joined using the "overlap" PCR method (amplification 3) (Horton et al., *BioTechniques*, 8:528–535 (1990)) with only the NotI primer and the SfiI primer. Complementarity between the AscI containing end of each initial DNA amplification product from reactions 1 and 2 allowed joining of these two pieces during amplification. Next the TPL was amplified (amplification 4) (sequences 6049 to 9730 of Ad-dl327 [identical to similar sequences from Ad5, Genbank accession #M73260]) from cDNA made from mRNA isolated from 293 cells (ATCC Accession No. CRL 1573) infected for 16 hrs. with Ad-dl327 using primers containing SfiI and XbaI sites respectively. DNA fragments from amplification reactions 3 and 4 were then joined using PCR (amplification 5) with the NotI and XbaI primers, thus creating the complete gene block.

Third, the ITR-encapsidation signal-TPL fragment was then purified, cleaved with NotI and XbaI and inserted into the NotI, XbaI cleaved pHR plasmid. This plasmid was designated pAvS6A⁻ and the orientation was such that the NotI site of the fragment was next to the T7 RNA polymerase site.

Fourth, the SV40 early polyA signal was removed from SV40 DNA as an HpaI-BamHI fragment, treated with T4 DNA polymerase and inserted into the SalI site of the plasmid pAvS6A- to create pAvS6 (FIG. 5).

D. Construction of Av1H9B

Factor IX cDNA (FIG. 6), which contains the entire protein coding sequence, 26 base pairs of 5' untranslated DNA (assuming translation starts at the third ATG of the message) and 160 base pairs of 3' untranslated DNA, was excised from pG1H9B by restriction digestion with ClaI, followed by filling in the 5' overhang using Klenow, followed by restriction digestion with SmaI. The Factor IX cDNA could also have been obtained according to the procedures disclosed in U.S. Pat. No. 4,994,371.

Figure 7:
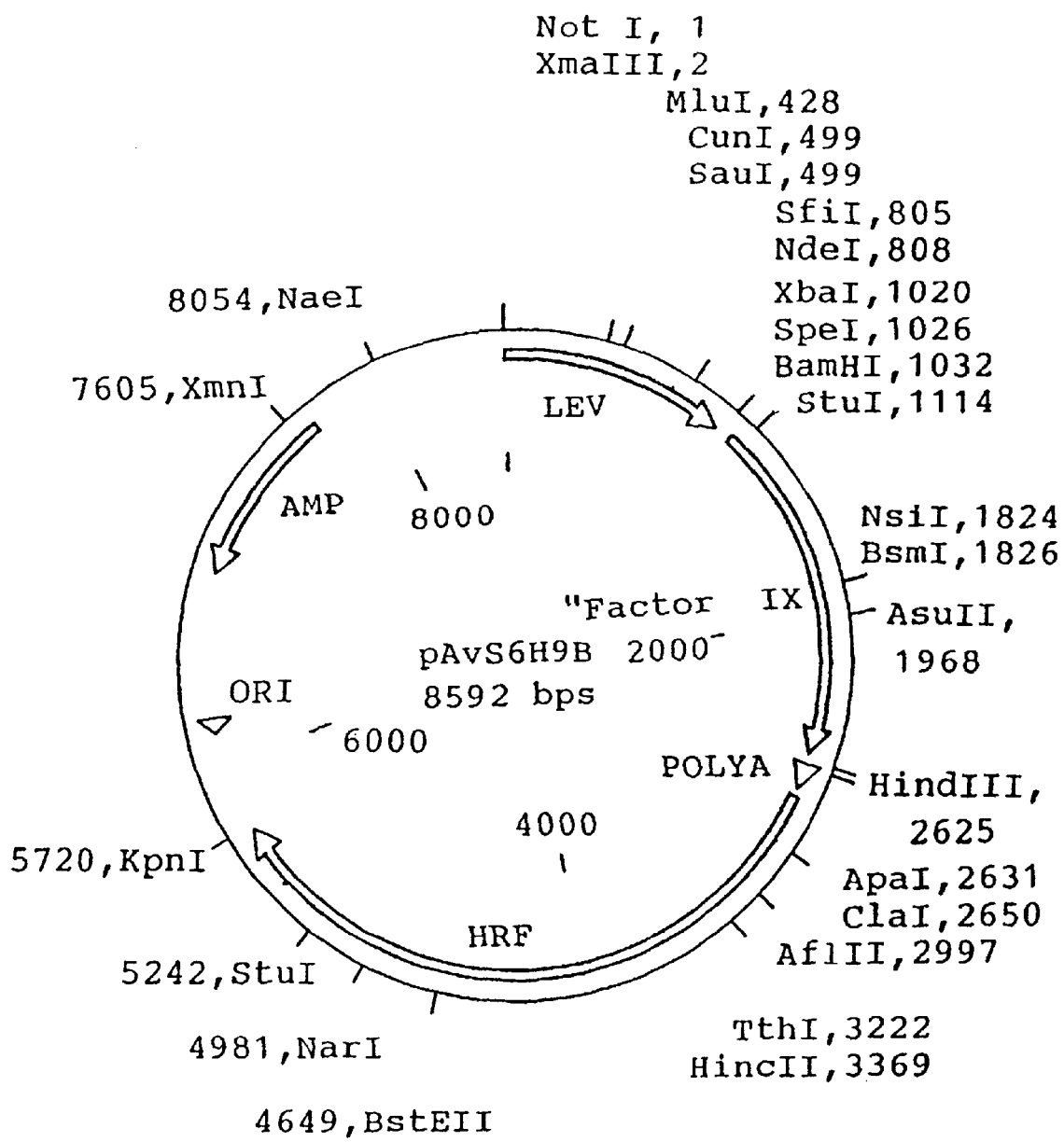
FIG. 7 is a map of pAvS6H9B.

The fragment encoding Factor IX was isolated by electrophoresis in a 1.0% agarose gel followed by electroelution of the DNA. This fragment was subcloned into pAvS6 which had been linearized with EcoRV and treated with calf intestinal phosphatase. The resulting shuttle plasmid pAvS6H9B (FIG. 7), contains the 5' inverted terminal repeat of adenovirus type 5 (Ad 5), the origin of replication of Ad 5, the Ad 5 encapsidation signal, the E1a enhancer, the RSV promoter, the tripartite leader sequence of Ad 5, Factor IX cDNA, the SV40 early polyadenylation signal, and Ad 5 sequences from nucleotide positions 3329–6246.

Figure 8:
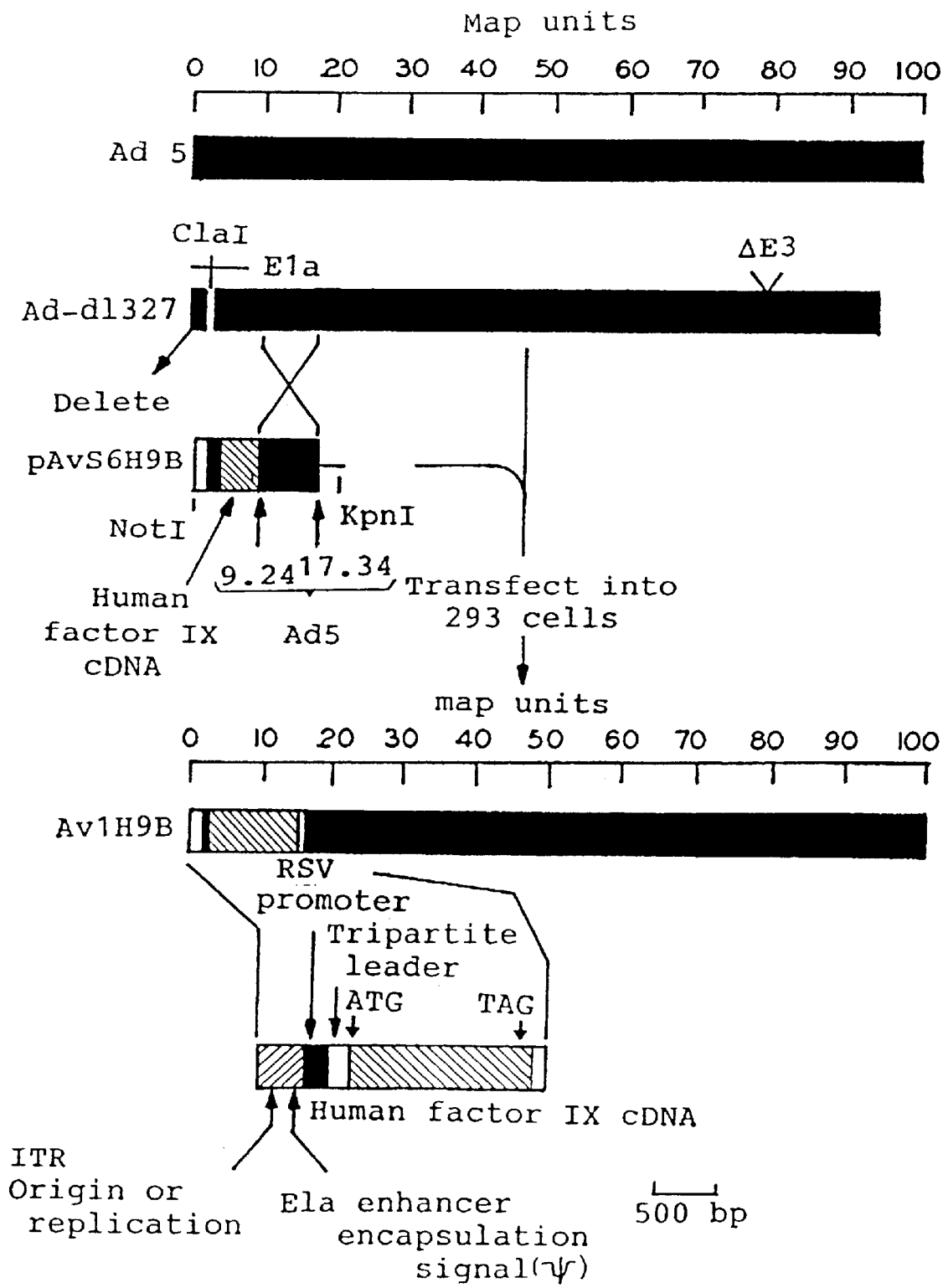
FIG. 8 is a schematic of the generation of Av1H9B.

The recombinant adenoviral vector Av1H9B was generated as depicted in FIG. 8. $1.5 \times 10^6$ 293 cells were cotransfected in a 60 mm tissue culture dish with 4 μg of the large Cla I fragment of Ad-dl327 (an E3 deletion mutant of Ad 5) and 5 μg of shuttle plasmid pAvS6H9B digested with Not I and Kpn I. Transfections were done using BRL's Transfinity calcium phosphate transfection system. Approximately 15 hours after transfection, medium containing DNA/calcium phosphate precipitate was removed from the dishes, the cells were gently washed with PBS, then overlaid with a 1:1 mixture of 2×MEM (GIBCO's 2×Modified Eagle Medium supplemented with 15% FBS) and 2% SeaPlaque agarose.

Plaques were picked using sterile Pasteur pipettes and transferred into 0.1 ml of infection medium (Improved Minimum Essential Medium (IMEM), 1% FBS) in an Eppendorf tube. Resuspended plaques were subjected to three freeze/thaw cycles, then cleared of cell debris by a 15 second centrifugation at full speed in a microfuge.

Recombinant adenovirus was amplified in 293 cells as follows. Approximately $5 \times 10^5$ 293 cells per dish were seeded into 30 mm dishes. The next day medium was removed from the cells and replaced with 0.2 ml of infection medium and 0.1 ml of a resuspended plaque. The plates were incubated with gentle rocking for 90 minutes in a 37° C., 5% $CO_2$ incubator. Subsequently, 2 ml of complete medium (IMEM, 10% FBS) were added. Approximately 40 hours later a cytopathic effect was clearly visible; cells were rounded-up and beginning to detach from the plate. Cells and medium were transferred to plastic tubes, subjected to four freeze/thaw cycles, and centrifuged at 2000×g for 5 minutes. The resulting supernatant is referred to as the crude viral lysate (CVL1).

Viral DNA was isolated from an aliquot of each CVL1, then analyzed for the presence of Factor IX cDNA by PCR, as follows. A 60 μl aliquot of supernatant was transferred into an Eppendorf tube and incubated at 80° C. for 5 minutes. The sample was centrifuged at full speed for 5 minutes in a microfuge, then 5 μl of the supernatant were used for PCR analysis. PCR analysis was done using the Perkin Elmer Cetus GeneAmp kit. Two different pairs of primers which amplify different portions of the human Factor IX cDNA were used. All samples yielded the expected amplified band.

EXAMPLE 2

In Vitro and in Vivo Function of the Vector of Example 1

Recombinant adenovirus vectors containing Factor IX cDNA were tested for their ability to express human Factor IX in 293 cells. Approximately 5×10⁵ 293 cells were seeded per 60 mm dish. The next day, medium was replaced with 0.1 ml of recombinant adenovirus and 0.1 ml of infection medium. Plates were incubated for 1 hour with gentle rocking at 37° C. in 5% CO$_2$, followed by addition of 4 ml of complete medium. The cells were gently washed five times with PBS, then 4 ml of complete medium were added. Media samples were collected 24 hours later and centrifuged at 1500×g for 5 minutes. Supernatants were assayed for human Factor IX by ELISA (Asserachrom IX:Ag ELISA kit, American Bioproducts), and the levels were 445 and 538 ng/ml for the two samples, demonstrating that the recombinant adenoviral vectors are able to express human Factor IX. Uninfected 293 cells yielded background levels of Factor IX.

One recombinant adenovirus was selected for a large scale virus preparation. Approximately 5×10⁶ 293 cells were seeded onto a 15 cm tissue culture dish. The next day, the medium was replaced with 4 ml of infection medium plus 1 ml of the crude viral stock. Then the plates were incubated at 37° C., 5% CO$_2$ with gentle rocking for 90 minutes, followed by addition of 15 ml of complete medium. Approximately 40 hours later, when a cytopathic effect was clearly visible, cells and medium were transferred to a 50 ml plastic tube. Cells were lysed by five freeze/thaw cycles and cell debris was removed by centrifugation at 1500×g for five minutes. This supernatant was termed CVL2.

15 ml of CVL2 then was mixed with 35 ml of infection medium and 5 ml of this mixture was added to each of ten 15 cm plates of nearly confluent 293 cells. The plates were incubated at 37° C., 5% CO$_2$ with gentle rocking for 1 hour, followed by addition of 15 ml complete medium to each plate. Twenty-four hours later a cytopathic effect was observed; cells were rounded-up, but not lysed. Cells and medium were centrifuged at 2000×g for 10 minutes. The cell pellet was resuspended in 6 ml of complete medium. Cells were lysed by five freeze/thaw cycles, followed by centrifugation in a SW40 rotor at 7000 rpm for 10 minutes at 4° C. Virus in the supernatant was purified on a CsCl step gradient as follows. 3.0 ml of 1.25 g/ml CsCl in TD buffer (25 mM Tris, 137 mM NaCl, 5 mM KCl, 0.7 mM Na$_2$HPO$_4$, pH7.5) was placed in an ultraclear Beckman #344060 ultracentrifuge tube. This was underlaid with 3.0 ml of 1.40 g/ml CsCl in TD buffer. The CsCl layers were overlaid with 4.5 ml of viral supernatant. Centrifugation was done at 35,000 rpm, 22° C. for 1 hour in a SW40 rotor. Two bands were visible, an upper band that consists of empty capsids and a lower band consisting of intact recombinant adenovirus.

The lower band was collected with a 3 ml syringe and a 21 gauge needle, and then rebanded as follows. 9.0 ml of 1.33 g/ml CsCl in TD buffer was placed into an ultracentrifuge tube. This was overlaid with the virus collected from the first spin. Centrifugation was done at 35,000 rpm, 22° C. for 18 hours. The opalescent band was collected as above and glycerol was added to a final concentration of 10%. The adenovirus was dialyzed against one liter of 10 mM Tris pH 7.4, 10 mM MgCl$_2$, and 10% glycerol at 4° C. Dialysis was done for 4 hours and the buffer was changed three times at one hour intervals. The virus was recovered and stored at −70° C. in aliquots in sterile Eppendorf tubes. The titer of this virus preparation was 9.6×10⁹ pfu/ml.

In the first in vivo experiment, the recombinant adenovirus Av1H9B was injected into three C57BL/6 mice by three different methods: an intraparenchymal injection into the liver, infusion into the portal vein, and infusion into the tail vein.

The animal which received an intraparenchymal injection was anesthetized under Metofane. A longitudinal incision approximately 7 mm in length was made just below the xiphoid. Pressure was applied to the flanks causing protrusion of the median and left lateral lobes. For injection, 0.1 ml of virus (1×10⁹ pfu) was diluted to 1.0 ml with Hanks Balanced Salt Solution (HBSS). The virus was injected into 4 different sites of the liver: 0.25 ml was injected into each half of the median lobe and into the left and right sides of the left lateral lobe. Each injection was done over approximately one minute. Upon removal of the needle, hemostasis was achieved by placing small pieces of gelfoam over the injection site. After 2 minutes, the gelfoam was removed, the liver was gently placed into the abdominal cavity, and the skin incision was closed with autoclips. Animals awakened within several minutes of surgery and were ambulatory within one hour.

The animal which received a portal vein infusion of AdH9B was anesthetized under Metofane. A midline longitudinal incision was made from the xiphoid to just above the pelvis. The intestines were gently externalized to the left side of the animal with wet cotton tip applicators. An 0.1 ml aliquot of virus (1×10⁹ pfu) was diluted to 1.0 ml with HBSS. The viral suspension was infused over 30 seconds into the portal vein using a 1 ml syringe and a 27 gauge needle. A 3×3 mm piece of gelfoam was placed over the injection site. The needle then was withdrawn. Hemostasis was achieved by applying mild pressure to the gelfoam for 5 minutes using a wet cotton tip applicator. The gelfoam was left in place. The intestines were gently returned to the abdominal cavity. The incision was closed using autoclips. The animal awakened within 30 minutes of surgery and was ambulatory within 1 hour.

A tail vein infusion of Av1H9B was performed using 0.1 ml of virus (1×10⁹ pfu) diluted to 1.0 ml with HBSS. The viral suspension was infused over a ten second period using a 27 gauge needle.

Figure 9:
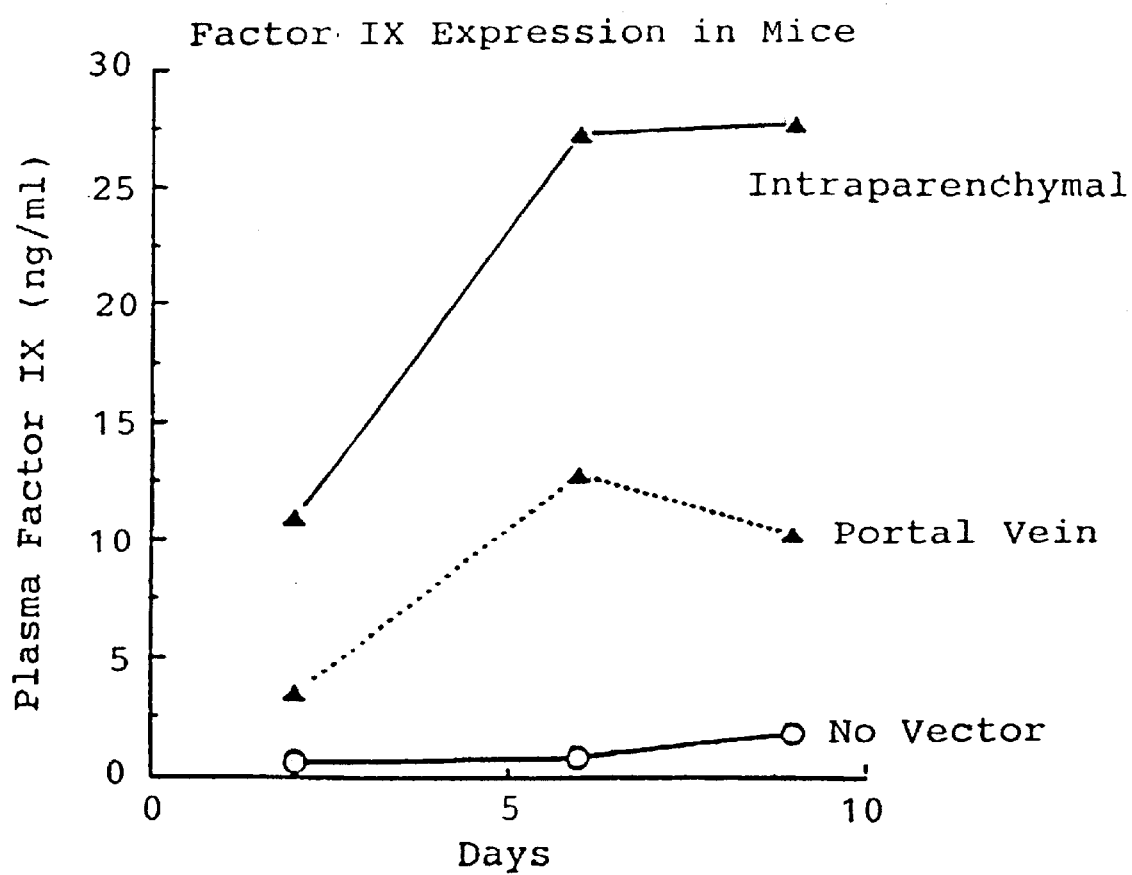
FIG. 9 is a graph of plasma levels of Factor IX in mice given intraparenchymal or portal vein injections of Av1H9B.

The animals which received an intraparenchymal injection and portal vein infusion, as well as a control mouse which received no virus, were bled via the retro-orbital plexus on days 2, 6, and 9 after virus delivery. The animal which received a tail vein infusion was bled 2 days after virus delivery. Plasma levels of human Factor IX were determined by ELISA. The results are shown in FIG. 9.

At this point, it was important to determine vector levels in the livers of the mice. Therefore, the animals which received an intraparenchymal injection and a portal vein infusion and the negative control mouse were sacrificed on day 9 after infusion and the mouse which received a tail vein injection was sacrificed on day 2 after infusion. The liver of each mouse was removed and extensively minced with a razor blade. One-half of each liver was placed into a 15 ml conical tube and 1.0 ml of lysis buffer (10 mM Tris, 0.14 M NaCl, pH 8.6) was added. The tissue was homogenized using a 1 ml syringe and a 20 gauge needle. Next, 1.0 ml of 2×PK buffer (200 mM Tris pH 7.5, 25 mM EDTA, 300 mM NaCl, 2% (w/v) SDS, and 500 μg/ml proteinase K) was added. The tube was inverted several times, then incubated at 37° C. overnight. The samples were extracted twice with phenol/chloroform (1:1) and once with chloroform/isoamyl alcohol (24:1). DNA was ethanol precipitated, washed with 70% ethanol, and resuspended in 10 mM Tris, pH 7.5, 1 mM EDTA.

A Southern analysis was performed to quantitate the levels of vector in the liver. Ten micrograms of each DNA sample were cut with BamHI. The digested DNA samples were subjected to electrophoresis in an 0.8% Seakem agarose gel in 40 mM Tris, 20 mM NaAcetate, 1 mM EDTA, pH7.5.

Figure 10:
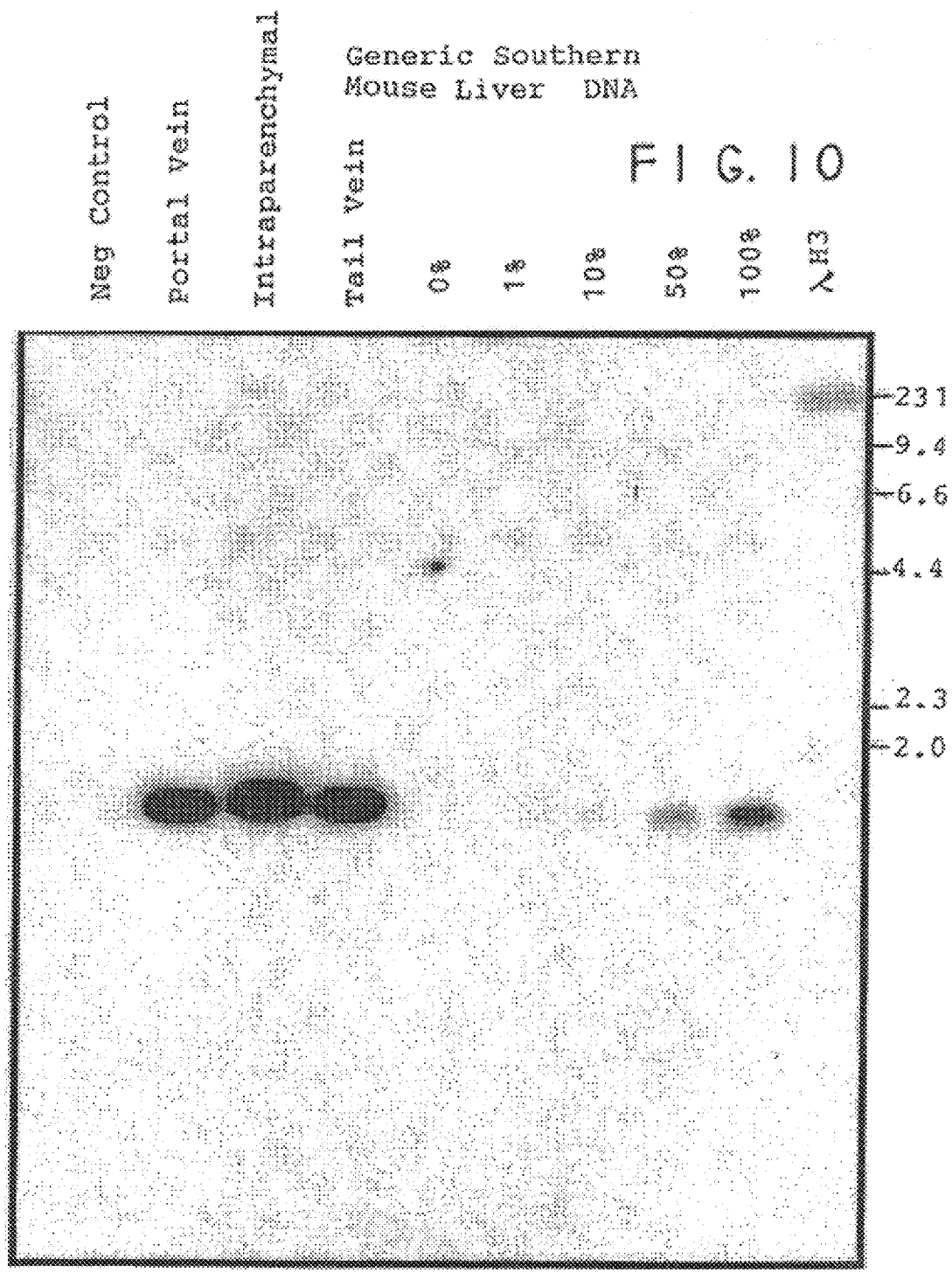
FIG. 10 is an autoradiogram of a Southern analysis to determine the presence of Factor IX DNA in mouse liver.

After electrophoresis, the gel was treated with 0.2 N NaOH, 0.6 M NaCl for 1 hour, then neutralized with 1 M Tris pH 7.4, 0.6 M NaCl for 30 minutes. The DNA was transferred to a nylon membrane by blotting in 10×SSC. The nylon membrane was baked at 80° C. for 1 hour in a vacuum oven. It was prehybridized for 3 hours at 42° C. in 5×Denhardt's, 5×SSC, 50 mM NaPhosphate pH 6.5, 250 μg/ml salmon sperm DNA, 0.1% SDS, and 50% formamide. The membrane was hybridized for 24 hours at 42° C. in 1×Denhardt's, 5×SSC, 20 mM NaPhosphate pH 6.5, 100 μg/ml salmon sperm DNA, 0.1% SDS, 50% formamide, and 33 μCi of random primer labeled human Factor IX cDNA. Random primer labeling was performed using the BRL kit. The membrane was washed in 2×SSC, 0.1% SDS for 20 minutes at room temperature, followed by a 30 minute wash in 2×SSC, 0.1% SDS at 50° C., and then a 30 minute wash in 0.1×SSC, 0.1% SDS at 68° C. The membrane was exposed to film for 16 hours, then developed. A copy of the autoradiogram is shown in FIG. 10. All three routes of administration yielded the same results. The Factor IX bands were the appropriate size with an intensity that indicated an average of 5–10 copies per liver cell.

EXAMPLE 3

In vivo Expression of Factor IX in Mice Injected with Av1H9B

A second large scale virus preparation of Av1H9B was performed using the same protocol described above, except that 28 15 cm plates of 293 cells were used to amplify the virus. This preparation yielded a much thicker opalescent band upon CsCl gradient centrifugation than the first virus preparation. The titer of this virus preparation was $1.1 \times 10^{11}$ pfu/ml.

A second in vivo experiment, designed to follow the time course of expression, was initiated using the new Av1H9B preparation. Virus was administered to mice as described above, except that 0.1 ml of a virus suspension ($1 \times 10^{10}$ pfu) was diluted to 1.0 ml with infection medium. Twenty-seven mice received an injection of recombinant adenovirus: 20 mice received a tail vein injection, 18 with Av1H9B and 2 with Av1lacZ4 (encoding β-galactosidase), 4 mice received an intraparenchymal injection of the liver, and 3 received an intramuscular injection. A negative control mouse was not injected. The animals were bled once a week for seven weeks. Plasma levels of human Factor IX are shown in Table I.

As shown in Table I, IP means intraparenchymal injection of Av1H9B, TV means a tail vein injection of Av1H9B, IM means an intramuscular injection of Av1H9B, LacZ means a tail vein injection of Av1lacZ4, and NI means no injection (control).

TABLE I

| Mouse | Injection | Week 1 | Week 2 | Week 3 | Week 4 |
|---|---|---|---|---|---|
| | | ng/ml Factor IX in plasma | | | |
| 1. | TV | 376 | 475 | 281 | 171 |
| 2. | TV | 270 | 500 | 392 | 336 |
| 3. | TV | 229 | 374 | — | — |
| 4. | TV | 240 | — | — | — |
| 5. | TV | 362 | — | — | — |
| 6. | TV | 346 | — | — | — |
| 7. | TV | 303 | 422 | 252 | 142 |
| 8. | TV | 260 | 573 | 394 | 220 |
| 9. | TV | 353 | 376 | 273 | 149 |
| 10. | TV | 321 | 357 | 270 | 246 |
| 11. | TV | 431 | 482 | 233 | 203 |
| 12. | TV | 347 | 332 | — | — |
| 13. | TV | 135 | 244 | 126 | 61 |
| 14. | TV | 261 | 294 | 187 | 148 |
| 15. | TV | 212 | 269 | 132 | 91 |
| 16. | TV | 207 | 255 | 214 | 176 |
| 17. | TV | 278 | 218 | 151 | 149 |
| 18. | TV | 170 | 308 | — | — |
| 19. | IM | 0.9 | 3.0 | 0.0 | 0.0 |
| 20. | IM | 1.0 | 2.7 | 0.0 | 0.0 |
| 21. | IM | 1.1 | 2.6 | 1.0 | 1.2 |
| 22. | IP | 364 | 316 | 174 | 131 |
| 23. | IP | 211 | 308 | 134 | 66 |
| 24. | IP | 305 | 252 | 155 | 206 |
| 25. | IP | 527 | 406 | 133 | 94 |
| 26. | LacZ | 0.0 | 2.8 | 1.5 | 0.4 |
| 27. | LacZ | 0.0 | 2.6 | 2.0 | 1.2 |
| 28. | NI | 0.0 | 2.6 | 1.5 | 0.5 |

| Mouse | Injection | Week 5 | Week 6 | Week 7 |
|---|---|---|---|---|
| 1. | TV | 98 | 34 | 16 |
| 2. | TV | 187 | 67 | 16 |
| 3. | TV | — | — | — |
| 4. | TV | — | — | — |
| 5. | TV | — | — | — |
| 6. | TV | — | — | — |
| 7. | TV | — | — | — |
| 8. | TV | 197 | 60 | 25 |
| 9. | TV | 131 | 90 | 46 |
| 10. | TV | 179 | 76 | 16 |
| 11. | TV | — | — | — |
| 12. | TV | — | — | — |
| 13. | TV | 84 | 62 | 17 |
| 14. | TV | 133 | 65 | 26 |
| 15. | TV | 94 | 64 | 33 |
| 16. | TV | — | — | — |
| 17. | TV | 92 | 57 | 23 |
| 18. | TV | — | — | — |
| 19. | IM | 0.0 | 2.0 | 0.0 |
| 20. | IM | 0.0 | 2.0 | 4.1 |
| 21. | IM | 0.1 | 2.0 | 0.0 |
| 22. | IP | 112 | 53 | 48 |
| 23. | IP | 42 | 28 | 19 |
| 24. | IP | 299 | 203 | 154 |
| 25. | IP | 57 | 21 | 13 |
| 26. | LacZ | 0.0 | 1.5 | 5.0 |
| 27. | LacZ | 0.0 | 1.5 | 4.0 |
| 28. | NI | 1.4 | 1.7 | 0.5 |

EXAMPLE 4

Assay for Biological Activity of Human Factor IX

The biological activity of human Factor IX in mouse plasma was determined by using an immunocapture, chromogenic assay. A 96-well microtiter plate was coated with a BGIX1 monoclonal antibody obtained from Elcatech, Inc., which recognizes, but does not inactivate, human Factor IX. Coating was done by adding 100 μl of a 10 μg/ml suspension of the antibody to each well and incubating at room temperature overnight. Plasma samples obtained from Mouse 7 in Example 3 two weeks after injection with the recombinant adenovirus (100 μl of 1:5 and 1:10 dilutions) were added to the wells and human Factor IX was allowed to bind. The wells were washed to remove unbound material, and captured human Factor IX was activated by adding 100 μl of a 2 μg/ml suspension of Factor XIa (Enzyme Research Labs) and incubating at 37° C. for 30 minutes. The wells were washed, and then 100 μl of a mixture containing 5.0 μg phospholipid (Kabi Pharmacia, Franklin, Ohio), 0.1 unit Factor X (Kabi), 0.5 unit Factor VIII (Elcatech), 3.4 μg I-2581 thrombin inhibitor (Kabi) and 2.5 mM $CaCl_2$ were added. The plate was incubated at 37° C. for 30 minutes, during which time Factor X was converted to Factor Xa. 100 µl of 0.5 mM N-N-alpha-benzyloxycarbonyl-D-arginyl-L-glycyl-L-arginine-p-nitroanilide-dihydro choloride, a chromogenic Factor Xa substrate, then was added and the plate was incubated at room temperature for ten minutes. The color development was stopped by adding 50 µl of 50% acetic acid. The absorbance at 405 nm was determined using a Bio-Rad microplate reader. Standard curves (log-log and linear-linear) were generated using normal pooled human plasma, assuming Factor IX levels of 5000 ng/ml. Biologically active Factor IX was determined to be 511 ng/ml according to the log-log method, and 415 ng/ml according to the linear-linear method. Such results are within experimental error, and indicate that essentially all of the total Factor IX antigen determined in Example 3 (422 ng/ml) is biologically active.

EXAMPLE 5

Figure 11:
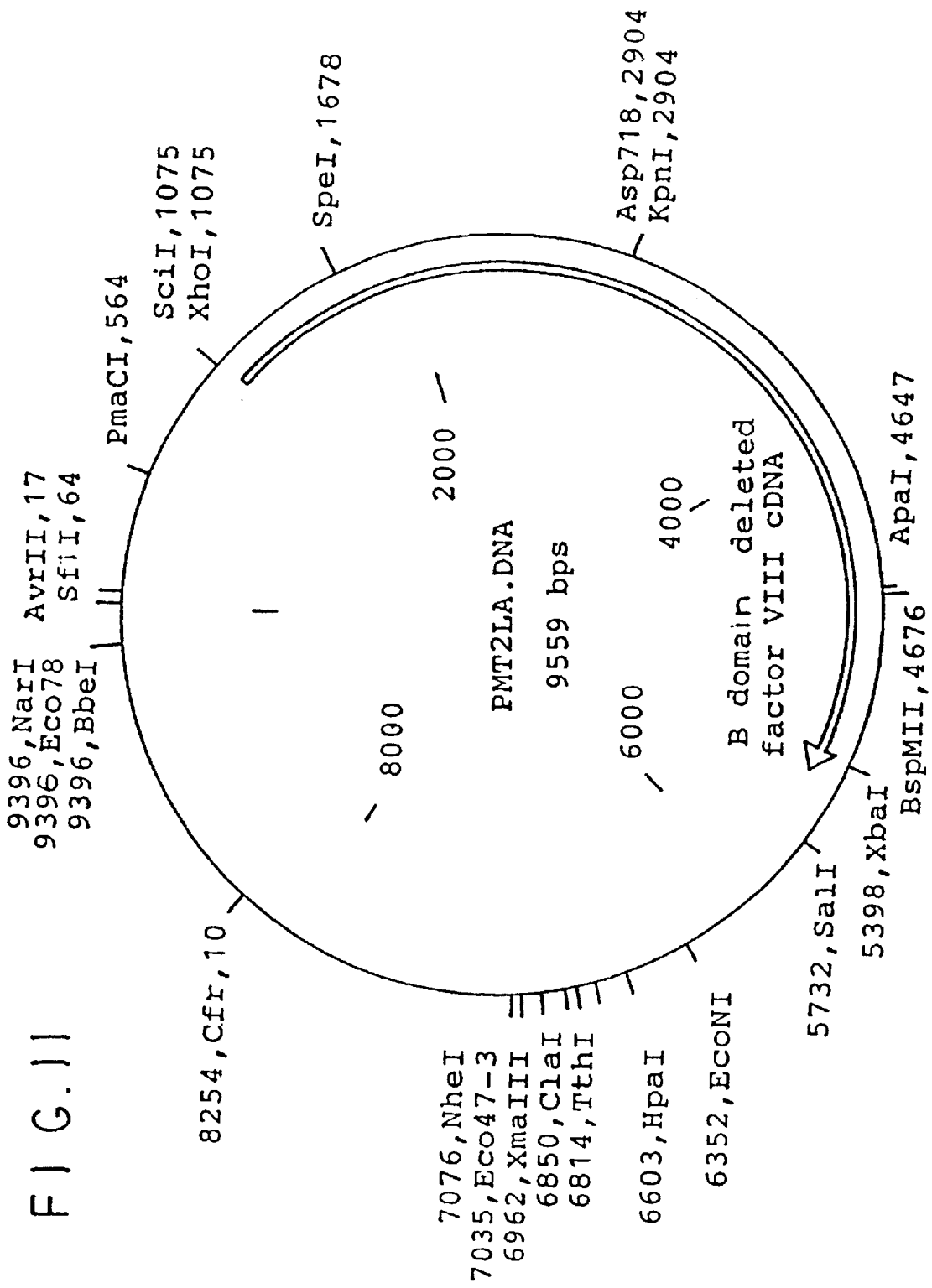
FIG. 11 is a map of plasmid pMT2LA.

Construction of Adenoviral Vector Including DNA Encoding a Factor VIII Derivative pAVS6H81 (FIG. 13) was constructed from pMT2LA (FIG. 11) and pAVS6. (FIG. 5). pMT2LA (Genetics Institute, Cambridge, Mass.) includes cDNA encoding a derivative of human Factor VIII in which the B domain of Factor VIII is deleted. Such cDNA is further described in Toole et al., *Nature,* Vol. 312, pgs. 342–349 (November 1984), Vehar et al., *Nature,* Vol. 312, pgs. 337–342 (November 1984), and Toole et al., *PNAS,* Vol. 83, pgs. 5939–5942 (August 1986). The cDNA is controlled by a Rous Sarcoma Virus promoter. The 4.6 kb cDNA (FIG. 12) contains no natural 5' untranslated DNA, and 216 bp of 3' untranslated DNA. The B domain deletion removes nucleotides 2334–4973 of the coding sequence of the full length Factor VIII. The cDNA for B domain deleted Factor VIII could also have been obtained according to the procedures disclosed in U.S. Pat. No. 4,868,112.

Figure 13:
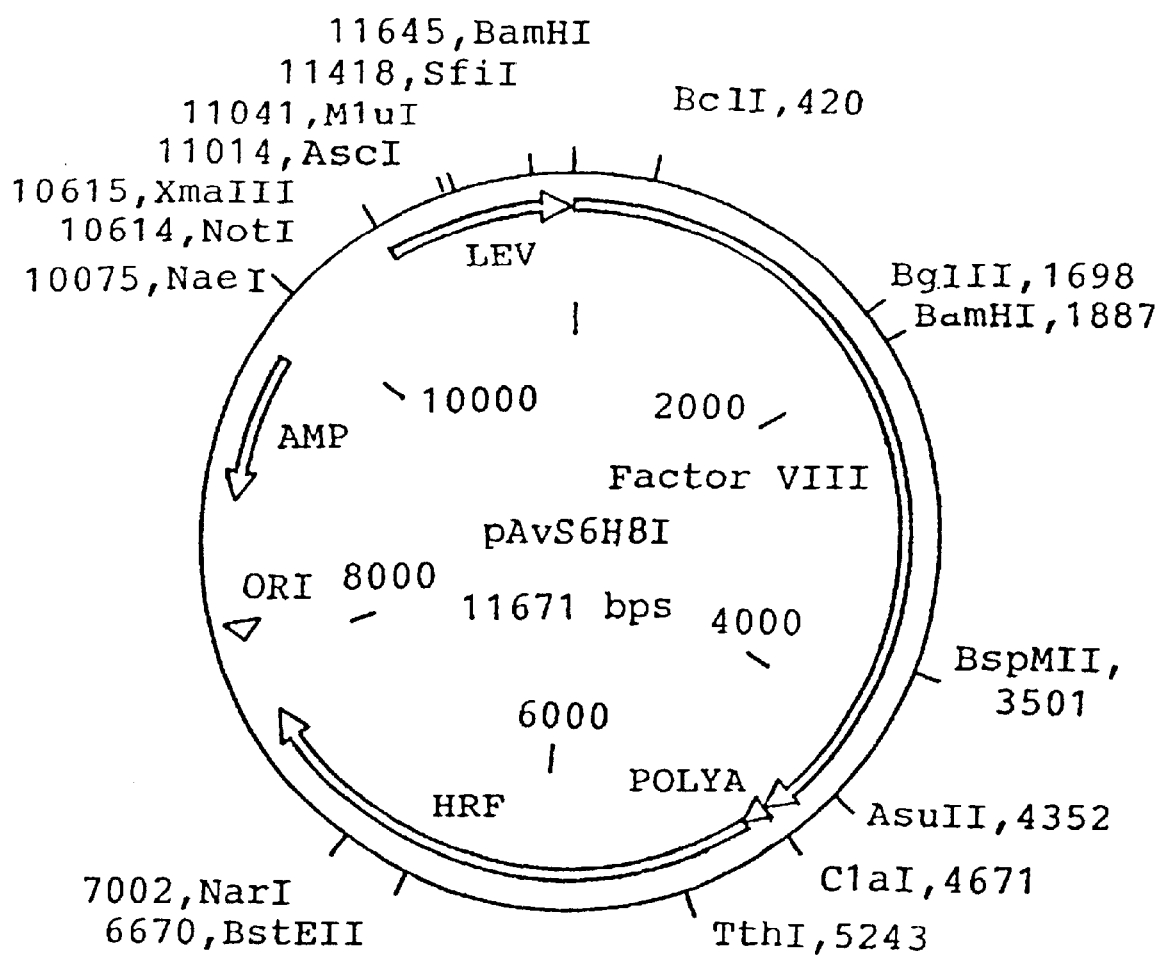
FIG. 13 is a map of plasmid pAvS6H81.

The cDNA was excised from the plasmid pMT2LA by restriction digestion with XhoI and SalI. The ends were filled in using Klenow, and the fragment encoding the Factor VIII derivative was isolated on an 0.8% agarose gel, followed by electroelution. This fragment was subcloned into the EcoRV site of pAVS6 (FIG. 10) to generate pAVS6H81. (FIG. 13.)

Figure 14:
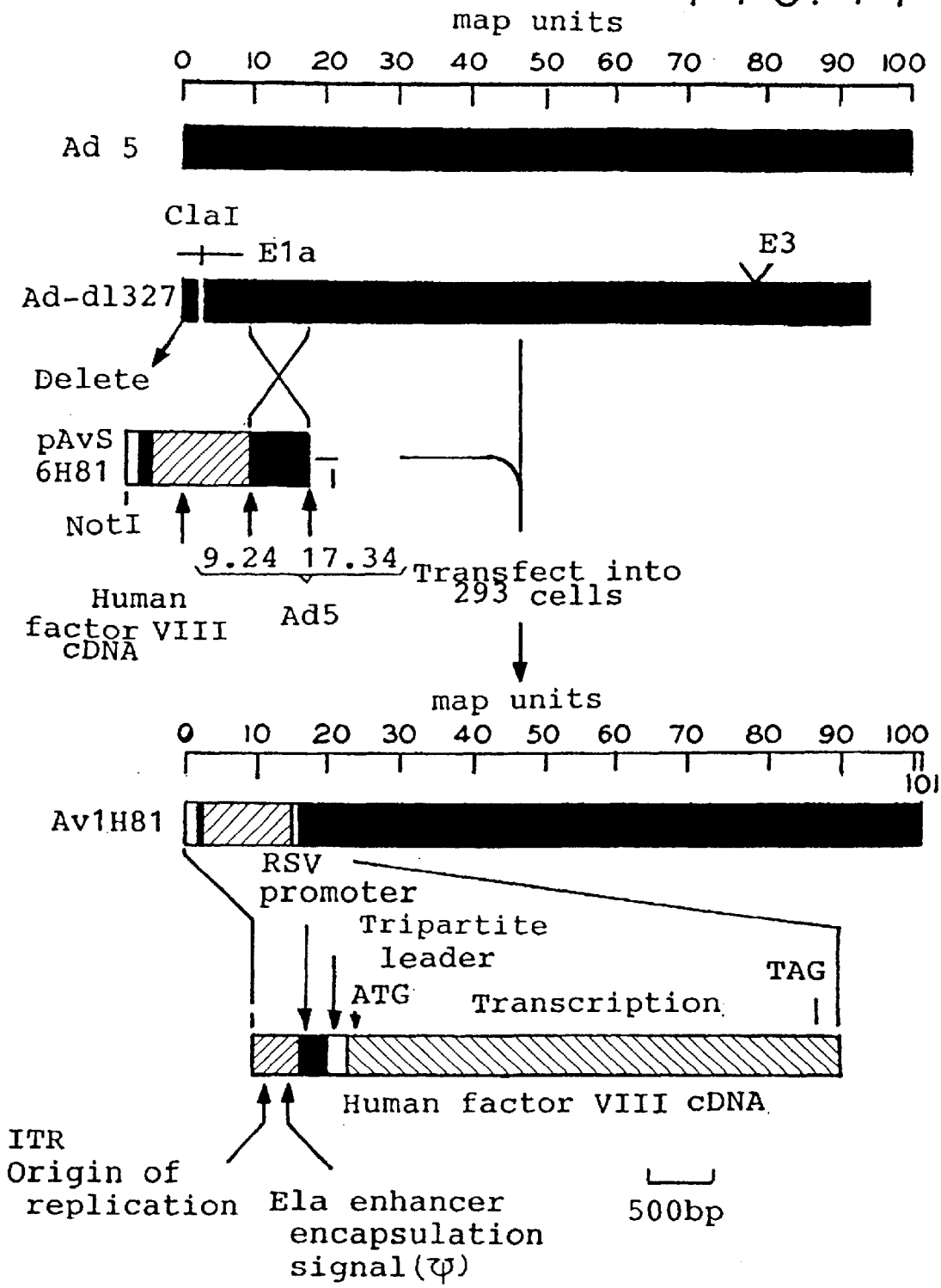
FIG. 14 is a schematic of the construction of Av1H81.

The recombinant adenoviral vector Av1H81 is generated as depicted in FIG. 14. 1.5×10⁶ 293 cells are cotransfected in a 60 mm tissue culture dish with 4 µg of the large ClaI fragment of Ad dl 327 and 5 µg of pAvS6H81 digested with NotI. Transfections are done using BRL's Transfinity calcium phosphate transfection system. Approximately 15 hours after transfection, medium containing DNA/calcium phosphate precipitate is removed from the dishes, the cells are gently washed with PBS, then overlaid with a mixture of 2×MEM and 2% Sea Plaque agarose.

Recombinant adenovirus can be prepared from plaques and analyzed by PCR for the presence of human Factor VIII cDNA.

EXAMPLE 6

Generation of Adenoviral Vectors Including DNA Encoding Factor VIII Plus Genomic Elements A. Construction of pAvALH81

Figure 15:
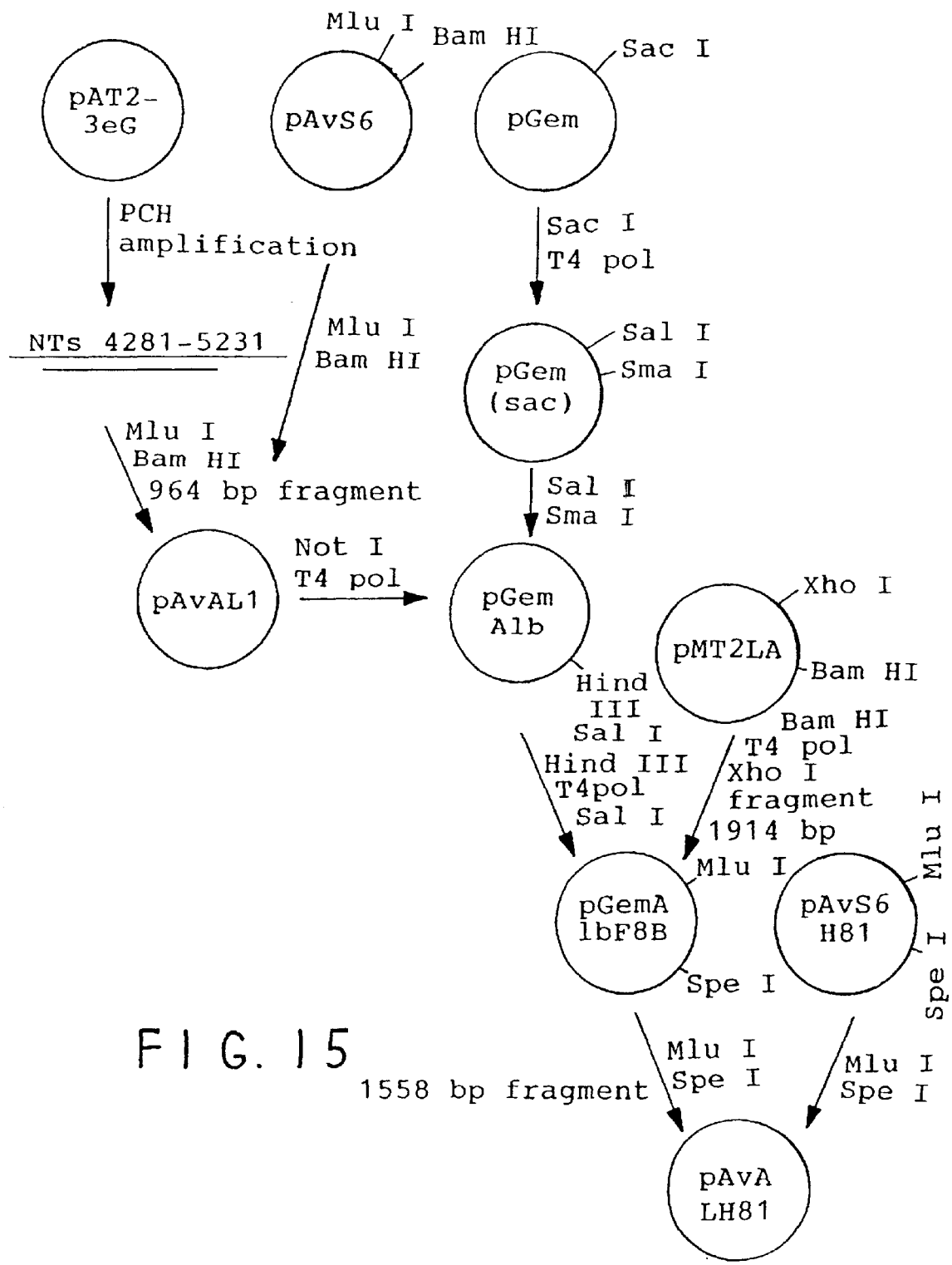
FIG. 15 is a schematic of the construction of plasmid pAvALH81.

A schematic of the construction of pAvALH81 is shown in FIG. 15. The mouse albumin promoter (Zaret et al., *Proc. Nat. Acad. Sci. USA,* Vol. 85, pgs. 9076–9080 (1988)), containing 3.5 copies of a liver-specific transcription factor binding site (eG binding sites, Liu et. al., *Mol. Cell. Biol.,* Vol. 11, pgs. 773–784 (1991) and Di Persio et al., *Mol. Cell. Biol.,* Vol. 11, pgs. 4405–4414 (1991)) was PCR amplified from pAT2-3eG (FIG. 15, provided by Kenneth Zaret, Brown University, Providence, R.I.) using oligo MGM8.293, (SEQ ID NO:1)
5'-GGC TAG ACG CGT GCT ATG ACC ATG ATT ACG AA-3' complementary to nts 4281–4299 of pAT2-3eG with the addition of an MluI restriction site, as the 5' oligo, and oligo MGM5.293,

5'-GGT ACG GAT CCA TCG ATG TCG ACG CCG GAA AGG TGA TCT GTGT-3' (SEQ ID NO:2)

complementary to nts 5231–5212 of pAT2-3eG with the addition of BamHI, ClaI, and SalI restriction sites, as the 3' oligo. The PCR product was cut with MluI and BamHI and inserted into PAVS6 (FIG. 5) cut with MluI and BamHI to generate pAVAL1 (FIG. 15). The sequence of the 964 bp PCR-generated albumin promoter has been verified by sequencing. In addition, at least 50 bp on either side of the MluI site (nt 428) and BamHI site (nt 1392) in pAVAL1 (FIG. 15) have also been verified by sequencing. The plasmid pAT-2-3eG is prepared according to the procedures disclosed in Dipersio et al., *Mol. Cell. Biol.,* 11:4405–4414 (1991) and Zaret et al., *Proc. Nat. Acad. Sci.,* Vol. 85, pgs. 9076–9080 (1988), which disclose the preparation of a mouse albumin promoter with two copies of a liver-specific transcription factor binding site. The plasmid pAT2-3eG has been deposited under the Budapest Treaty in the American Type Culture Collection, 1230 Parklawn Drive, Rockville, Md. 20892, and assigned accession number 69603.

Figure 16:
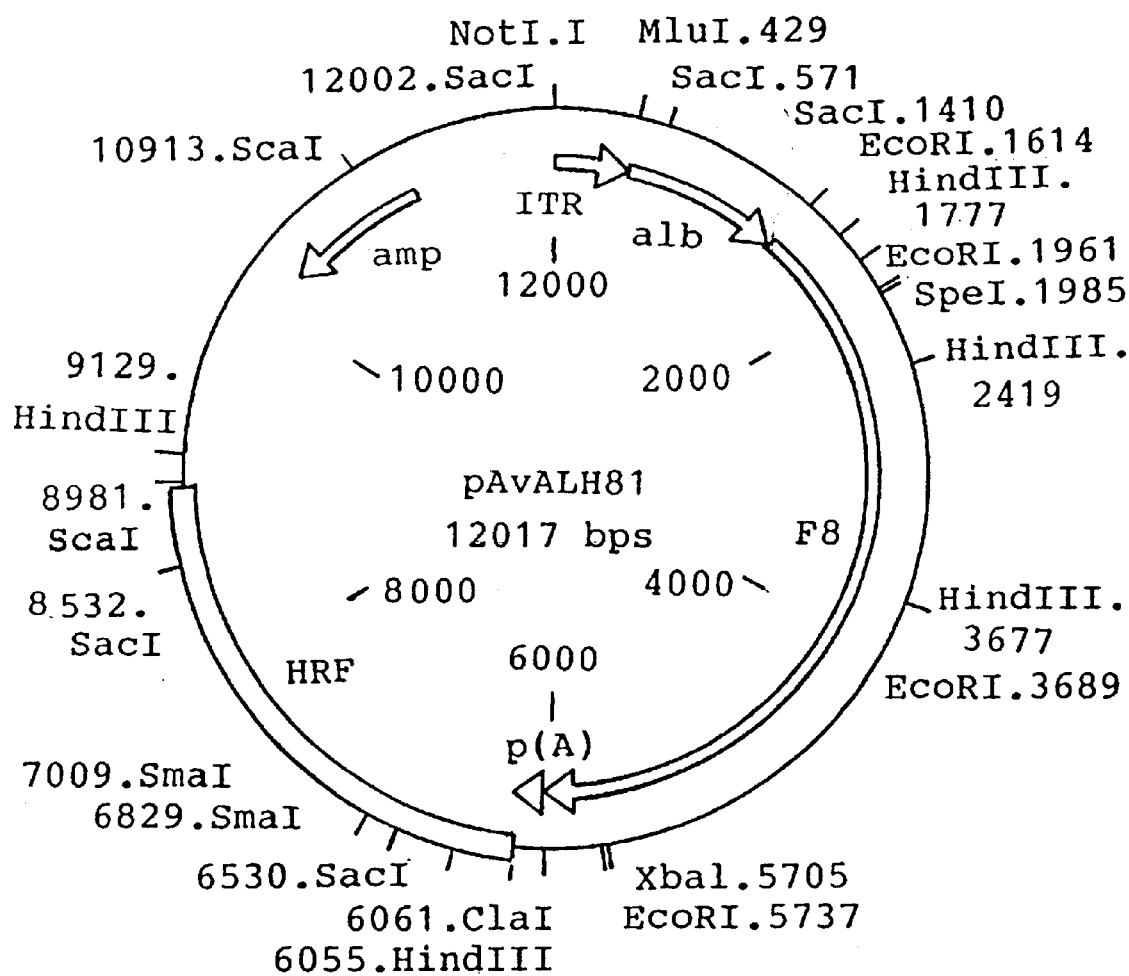
FIG. 16 is a map of plasmid pAvALH81.

The ITR, encapsidation signal (see construction of pAVS6) and the albumin promoter were removed from pAVAL1 by digestion with NotI (the ends were filled in with T4 DNA polymerase) and SalI, and inserted into pGEM(sac) (FIG. 15), cut with SalI and SmaI to generate pGEMalb (FIG. 15) (pGEM(sac) was created by cutting PGEM (FIG. 15, Promega; Madison, Wis.) with SacI, and blunting the ends with T4 DNA polymerase and religation, thereby removing the SacI site.) A 1914 bp fragment, containing the 5' region of the B-domain deleted factor VIII cDNA was isolated from pMT2LA (FIG. 11) by digestion with BamHI (filling in the 5' end with T4 DNA polymerase) and digestion with XhoI, and inserted into pGEMalb digested with HindIII (filled in with T4 DNA polymerase) and SalI, to generate pGEMalbF8B (FIG. 15). pGEMalbF8B was cut with MluI and SpeI, and the resulting 1556 bp fragment was inserted into pAvS6H81 (FIG. 13), cut with MluI and SpeI, to generate the adenovirus shuttle plasmid, pAvALH81 (FIG. 16). At least 50 bp on either side of the MluI site (nt 429) and SpeI site (nt 1985) have been verified by sequencing of Av1ALH81 viral DNA (see below). The sequence of the Factor VIII B-domain deleted cDNA has been verified by sequencing of bases 1075 to 5732 from the original plasmid, pMT2LA (FIG. 11) obtained from Genetics Institute. It should be noted that this sequence differs from the sequence reported by Genetics Institute by two bases. One base change, nt 1317 of pMT2LA was reported by Genetics Institute to be a T (Toole et. al., Nature, Vol. 312, pgs. 342–347 (1984) and by Wood et. al., Nature, Vol. 312, pgs. 330–337 (1984) to be an A. In addition, nt 5721 of pMT2LA, reported by Genetics Institute to be a T, was deleted, thus creating a BamHI site within the Factor VIII 3' untranslated region. This mutation does not change the Factor VIII coding region.

B. Construction of pAvAPH81

Figure 17:
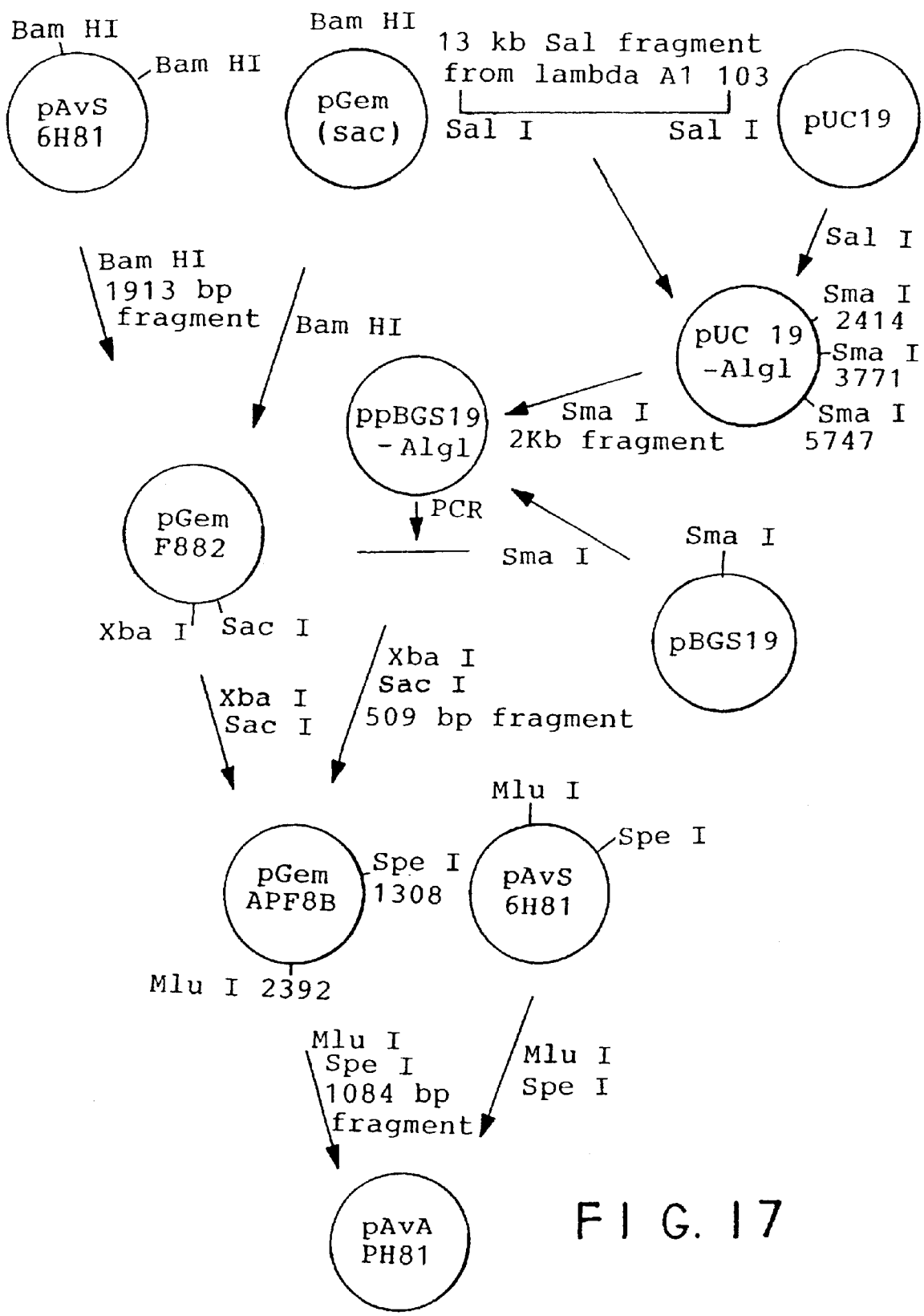
FIG. 17 is a schematic of the construction of plasmid pAvAPH81.
Figure 18:
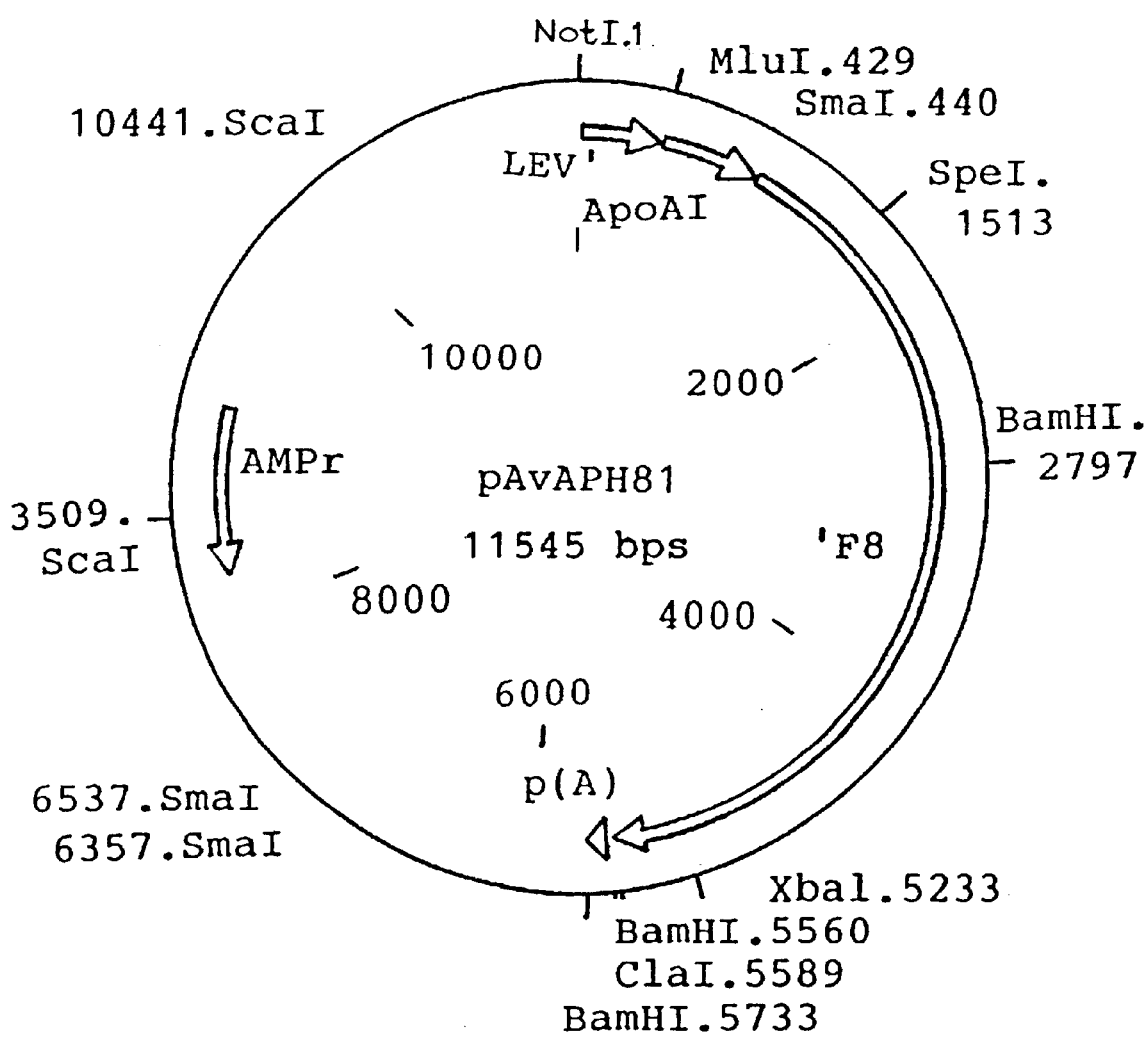
FIG. 18 is a map of plasmid pAvAPH81.

A schematic of the construction of pAvAPH81 is shown in FIG. 17. A 1913 bp fragment was isolated from pAVS6H81 (FIG. 13) by digestion with Bam HI, and inserted into pGEM(sac) (FIG. 15) cut with Bam HI, to create pGemF8B2 (FIG. 17). The ApoA1 promoter, first exon (untranslated), first intron, and second exon to the ATG (Genbank #X07496) were PCR amplified using pBGS19-AIgI (FIG. 17) as the template. pBGS19-AIgI (FIG. 17) was constructed in two steps: 1) The 13 kb SalI fragment was removed from Lambda Al 103 (Swanson, et. al., *Transgenic Research*, Vol. 1, pgs. 142–147 (1992), and inserted into pUC19 (FIG. 17, Gibco BRL) to generate pUC19-AIgI (FIG. 17). 2) The 2 kb SmaI fragment was isolated from pUC19-AIgI (FIG. 30) and inserted into pBGS19 (FIG. 17) to generate pBGS19-A1gI (FIG. 17). pBGS19 (ATCC No. 37437) is a kanamycin analog of pUC19. PCR-amplification of pBGS19-AIgI was performed using oligo SSC1.593,

5'GCT CTA GAA CGC GTC GGT ACC CGG GAG ACC TCG AAG CC-3' (SEQ ID NO:3)

complementary to bases 5862 to 16 of pBGS19-AIgI, containing an XbaI and a MluI site, as the 5' oligo, and a 3' oligo SSC2.593,

5'-GGA ATT CGA GCT GTAT TGG CAT CCT GAA GGG CGG TGG GGA CCT GG-3' (SEQ ID NO:4)

complementary to human factor VIII (Genbank #KO1740, nts 151–165 (to the SacI site), and nts 463–487 of pBGS19-AIgI, complementary to the ApoA1 gene (Genbank #X07496) with the addition of a SacI and an EcoRI site. The PCR fragment was digested with XbaI and SacI and the resulting 509 bp fragment was inserted into pGemF8B2 (FIG. 17) digested with XbaI-SacI, to generate pGemAPF8B (FIG. 17). pGemAPF8B was then digested with MluI-SpeI, and the resulting 1084 bp fragment was ligated into pAVS6H81 (FIG. 18) cut with MluI and SpeI, to generate the shuttle plasmid, pAvAPH81 (FIG. 18). The sequence of pAvAPH81, from nts 290 to 1619, which include the PCR-generated ApoA1 promoter region, and all cloning junctions, has been verified.

C. Construction of pAvALAPH81

Figure 19:
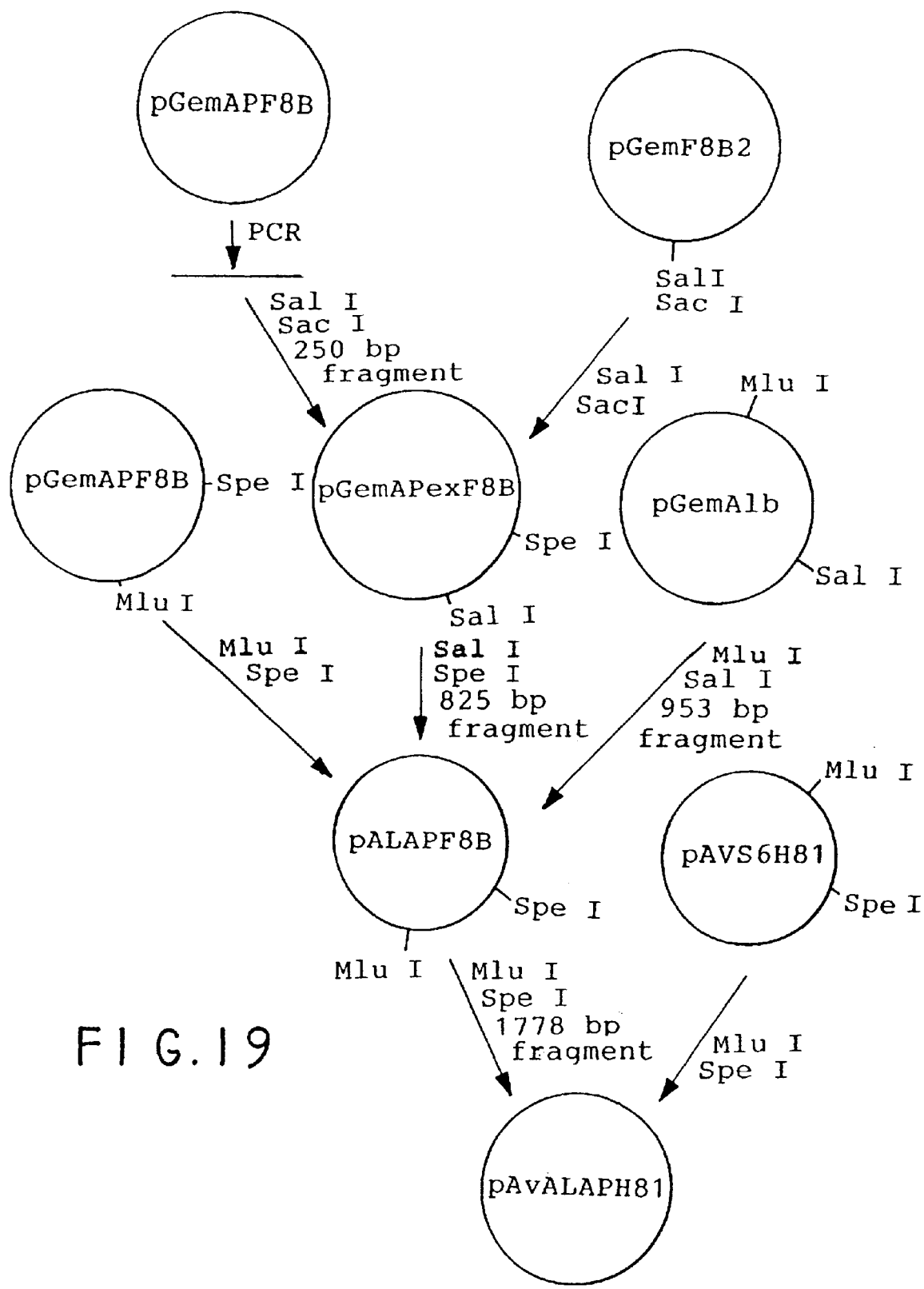
FIG. 19 is a schematic of the construction of plasmid pAvALPH81.
Figure 20:
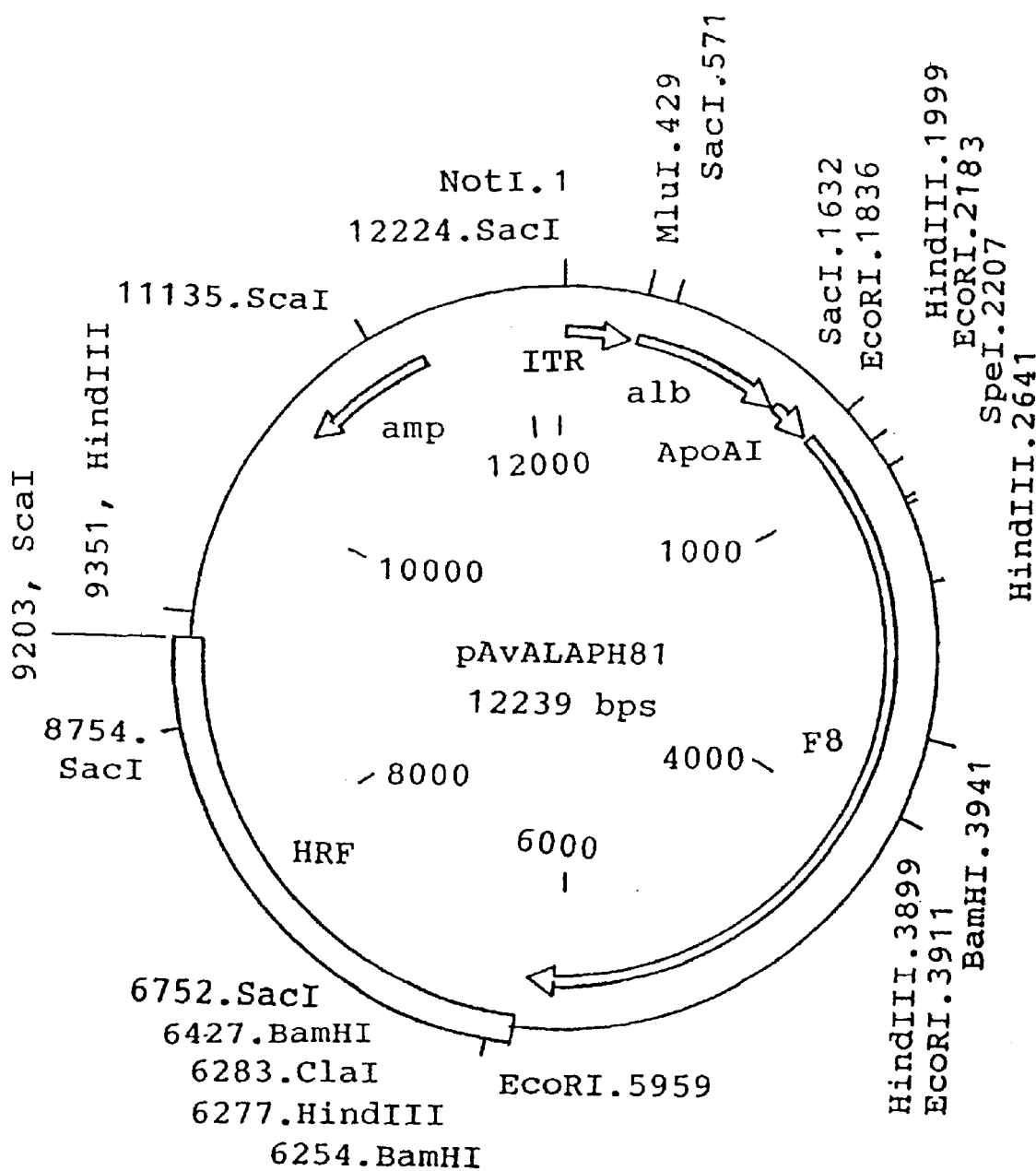
FIG. 20 is a map of plasmid pAvALAPH81.

A schematic of the construction of pAvALAPH81 is shown in FIG. 19. A SalI site was added upstream from the ApoA1 transcription initiation site by PCR amplification of pGemAPF8B (FIG. 17) using a 5' oligo SSC3.593,

5'-GAA TTC GTC GAC AGA GAC TGC GAG AAG GAG GTG CG-3' (SEQ ID NO:5)

complementary to the ApoA1 gene (Genebank #X07496) and nts 252–274 of pBGS19-A1g1 (FIG. 17) with the addition of an EcoRI and a SalI site, and a 3' oligo, SSC2.593 (see above). The PCR fragment was digested with SalI-SacI, and the resulting 250 bp fragment was inserted into pGemF8B2 (FIG. 17) cut with SalI-SacI, to create pGemAPexF8B (FIG. 19). The plasmid, pALAPF8B (FIG. 19) was generated by a 3-way ligation of the 953 bp MluI-SalI fragment isolated from pGEMalb (FIG. 15), the 825 bp SalI-SpeI fragment isolated from pGemAPexF8B (FIG. 19), inserted into pGemAPF8B (FIG. 17) cut with MluI-SpeI. The 1778 bp MluI-SpeI fragment was isolated from pALAPF8B (FIG. 19) and inserted into pAVS6H81 (FIG. 13) to generate the shuttle plasmid, pAvALAPH81 (FIG. 20).

D. Generation of Recombinant Adenovirus Vectors

Figure 21:
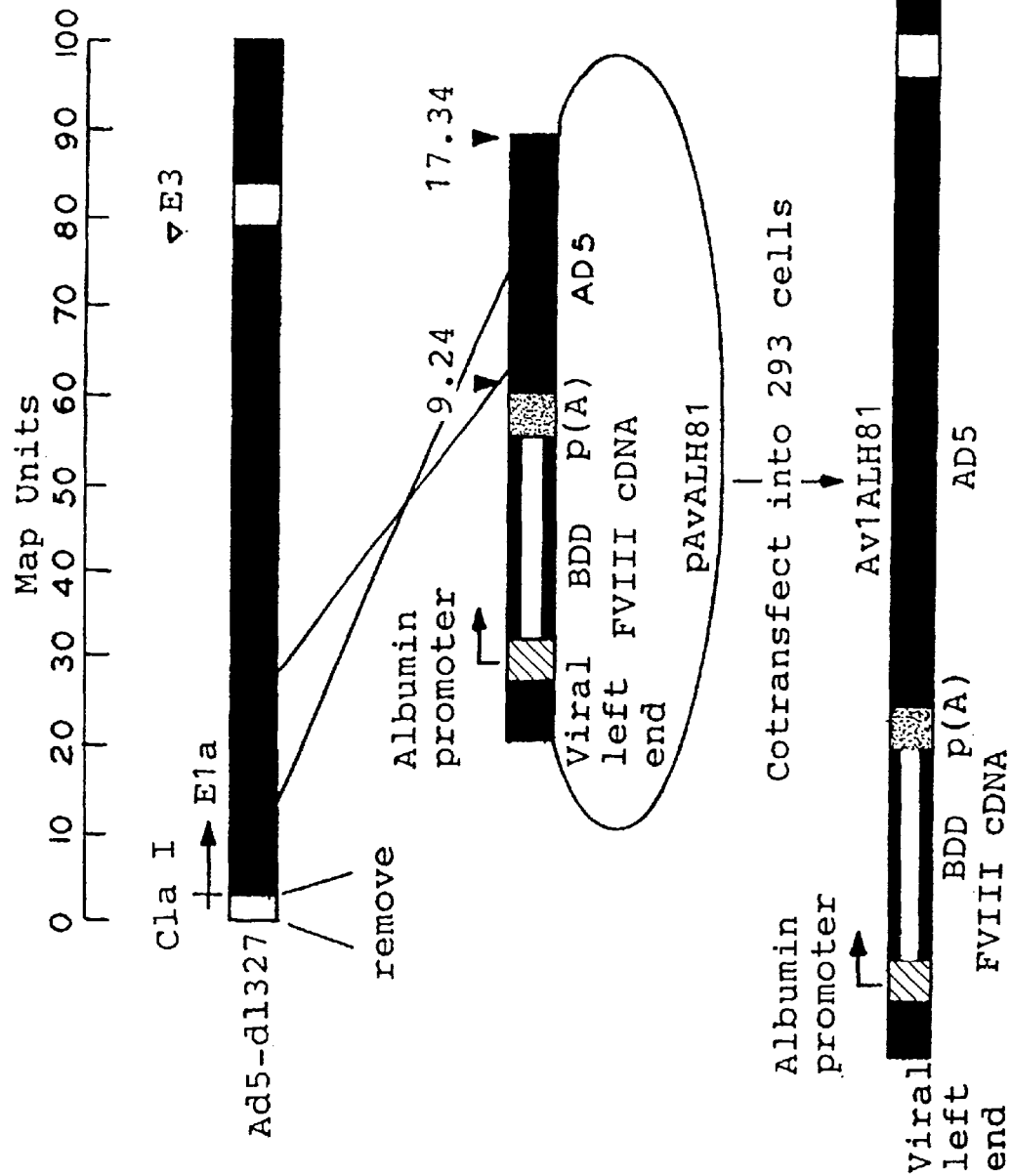
FIG. 21 is a schematic of the generation of Av1ALH81.

The recombinant adenoviral vector, Av1ALH81, was generated as outlined in FIG. 21. $2 \times 10^6$ 293 cells were cotransfected in a 100 mm tissue culture dish with 10 μg of the large ClaI fragment of Ad-dl327, and 10 μg of the undigested shuttle plasmid, pAvALH81 (FIG. 16). Transfections were performed using the Transfinity calcium phosphate transfection system from BRL. Approximately 12 hrs after DNA addition, the cells were washed 2× with 1× PBS, then overlaid with a 1:1 mixture of 2×MEM (GIBCO'S 2×Modified Eagle Medium supplemented with 15% FBS) and 2% SeaPlaque agarose.

Plaques were harvested with sterile Pasteur pipettes and transferred into 0.1 ml of infection medium (Improved Minimum Essential Medium ([IMEM], 2% FBS) in an Eppendorf tube, and subjected to three rounds of freeze/thaw cycles. Cell debris was removed by a 15 second centrifugation at full speed in a microfuge.

Plaques were screened for the presence of recombinant adenovirus as follows. Approximately $5 \times 10^5$ 293 cells were seeded per well of 6-well tissue culture plates. The following day, media was removed from the cells and replaced with 0.4 ml of infection medium and 0.05 ml of the resuspended plaque. The plates were incubated with rocking, for 90 min. in a 37° C./5% $CO_2$ incubator, after which 2 ml of complete medium (IMEM, 10% FBS) were added. When the cytopathic effect (CPE) was complete, cells were rounded and becoming detached from the plate (approximately 40–120 hrs after infection), cells and medium were transferred to 15 ml conical tubes, and centrifuged at 1000 rpm for 5 min. to pellet cells. The medium was removed from the cell pellet, and the cells were processed as follows.

Cells were resuspended in 250 μl of PK buffer (5 mM Tris pH 8.0, 5 mM EDTA, pH 8.0, and 0.5% SDS) plus 250 μl of Proteinase K (1 mg/ml), and incubated 4 hrs or overnight at 37° C. The solution was transferred to Eppendorf tubes and extracted with an equal volume of phenol 1×, phenol-CHCl$_3$ 1×, and CHCl$_3$ 1×, and ethanol precipitated. Pellets were resuspended in 50 μl of TE buffer (10 mM Tris pH 8.0, 1 mM EDTA pH 8.0), and genomic DNA was analyzed by restriction digestion. One plaque yielded the expected product.

This plaque of Av1ALH81 was plaque purified as follows. 5×10$^5$ 293 cells per well were plated on a 6-well tissue culture plate. The next day, medium was removed from the cells, and 0.4 ml of infection medium containing 3 varying amounts of the resuspended plaque were added to each well, 25 μl, 2.5 μl, and 0.25 μl. The plate was rocked for 1.5 hrs in a 37° C./5% CO$_2$ incubator, after which the media was removed, and the wells were overlaid with a 1:1 mixture of 2×MEM and 2% SeaPlaque agarose as described. Plaques were visible in all wells 9 days after infection. Several plaques were picked from the lowest dilution well (0.25 μl of resuspended plaque), and screened for the presence of Av1ALH81 as described. All plaques yielded the expected virus.

One plaque-purified plaque was selected for large scale virus preparation. 5×10$^5$ cells were plated in each well of a 6 well plate and the next day infected with 50 μl of the resuspended plaque-purified plaque as described. Five days after infection, the CPE was complete, cells and medium were transferred to 15 ml conical tubes and subjected to four freeze/thaw cycles, then cleared of cell debris by centrifugation at 1000 rpm for 5 min. The resulting supernatant is referred to as crude viral lysate #1 (CVL-1). This CVL was used to infect a 150 mm plate containing approximately 2×10$^7$ 293 cells as follows.

Medium was replaced with 1.25 ml of Infection Medium plus 100 μl of CVL, and the plate was rocked for 1.5 hrs as described, after which 20 mls of complete medium was added. Approximately 20 hrs after infection, the CPE was complete, and cells and medium were transferred to a 50 ml conical tube, spun for 5 min at 1000 rpm, supernatant was removed and saved, and the cell pellet was resuspended in 5 ml of supernatant. After four freeze/thaw cycles, the CVL was removed of cell debris as described. The resulting supernatant is referred to as CVL-2. 30–80% confluent 150 mm plates of 293 cells were infected using the CVL-2 as follows.

600 μl of CVL-2 was added to 38 mls of Infection Medium, medium was removed from the plates, and replaced with 1.25 ml of the CVL-2-Infection Medium mixture. Plates were rocked for 1.5 hrs as described, after which 20 mls of complete medium was added to each plate. The CPE was complete after 30 hrs and cells were processed as follows. Cells and media were harvested into 250 ml centrifuge bottles and spun at 1500 rpm for 10 min. The cell pellet was resuspended in 20 mls of supernatant. Cells were lysed by five freeze/thaw cycles, followed by centrifugation in a SW40 rotor at 7000 rpm for 10 min at 4° C. Virus in the supernatant was purified on a CsCl step gradient as follows.

3.0 ml of 1.25 g/ml CsCl in TD buffer (25 mM Tris, 137 mM NaCl, 5 mM KCl, 0.7 mM Na$_2$HPO$_4$ Ph 7.5) was placed in four ultraclear Beckmann #344060 ultracentrifuge tubes. 3.0 ml of 1.4 g/ml CsCl in TD buffer was then underlaid. The CsCl layers were overlaid with 5.0 ml of viral supernatant. Centrifugation was performed at 35,000 rpm, 22° C. for 1 hr in a SW40 rotor. Two bands were visible, an upper band consisting of empty capsids, and a lower band composed of intact recombinant adenovirus.

The lower band was collected with a 3 ml syringe and a 18 gauge needle, and then rebanded by placing 8.0 ml of 1.33 g/ml CsCl in TD buffer into two ultracentrifuge tubes, and overlaying with virus collected from the first spin. Centrifugation was performed at 35,000 rpm, 22° C. for 18 hrs. The viral band was collected as described and glycerol was added to a final concentration of 10%. The virus was dialyzed against one liter of 10 Mm Tris pH 7.4, 10 Mm MgCl$_2$, and 10% glycerol at 4° C. Dialysis lasted for four hours with buffer changes every hour. The virus was recovered and stored at −70° C. in aliquots in sterile Eppendorf tubes. The titer of this virus preparation (Lot # MS1-1) was 1.5×10$^{11}$ pfu/ml. A second Av1ALH81 viral prep was made in a similar manner as described, again using 600 μl of CVL-2 and 30–150 mm plates of 80% confluent 293 cells. The titer of the second prep (Lot # MS1-2) was 9×10$^{10}$ pfu/ml.

Figure 22:
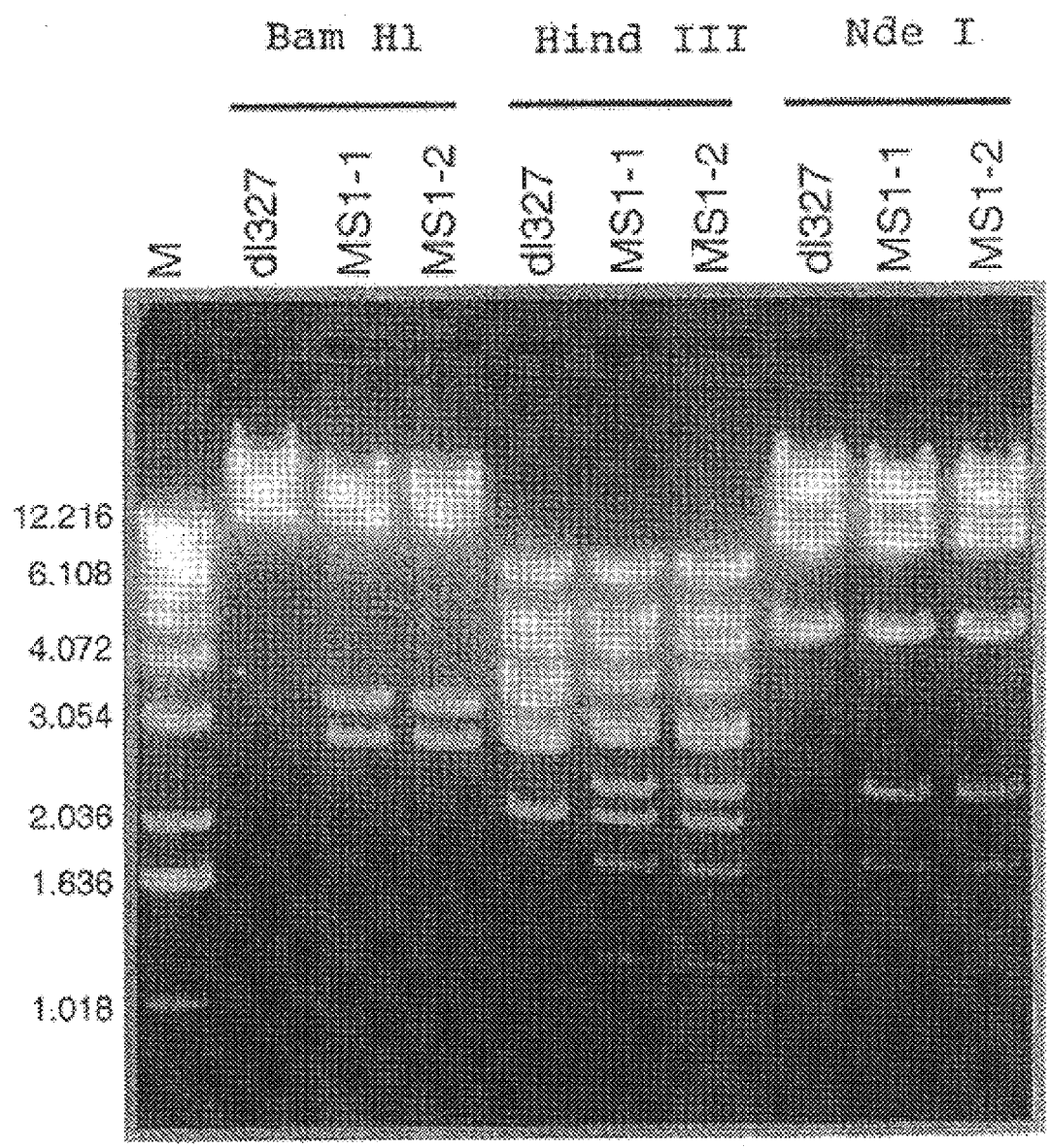
FIG. 22 is a photograph of an ethidium bromide stained gel showing restriction digestion analysis of Av1ALH81 DNA.

At this stage, the viral DNA is checked for deletions or rearrangements. Studies utilizing retroviral vectors containing Factor VIII cDNA sequences have been shown to delete and/or rearrange portions of the Factor VIII cDNA at high frequencies (Lynch et. al., 1993), and similar rearrangements may be seen with Factor VIII-containing adenoviral vectors. Therefore, viral DNA was isolated from both lots (MS1-1, and MS1-2) of AvALH81 as follows. 100 μl of purified virus was added to 100 μl of TE, 5 μl of 10% SDS, and 20 μl of 10 mg/ml Proteinase K (Sigma), and digested overnight at 37° C. The viral DNA was extracted with an equal volume of phenol 1×, phenol-CHCl$_3$ 1×, and CHCl$_3$ 1×, then the supernatant was put over a Centricon 10 concentrator (Amicon) and the volume was increased to 2 mls with TE, and spun at 5000 rpm for one hour. The centricon was then washed with 2 mls of TE, and spun for 30 min at 5000 rpm. DNA was recovered by inverting the upper chamber of the centricon, inserting into the collection tube, and centrifugation at 3000 rpm for 5 min. Final volume of the purified DNA was increased to 100 μl, and the DNA concentration was calculated. 10 μg of MS1-1, MS1-2, and dl327 DNA was digested overnight with BamHI, HindIII, or, NdeI, and run on a 0.8% agarose gel. DNA fragments were visualized with ethidium bromide staining (FIG. 22). Both Av1ALH81 lots look the same, and all restriction fragments are of the predicted sizes. Therefore, unlike the Factor VIII-containing retroviral vectors (Lynch et. al., 1993), the genome of Av1ALH81 is stable.

Figure 23:
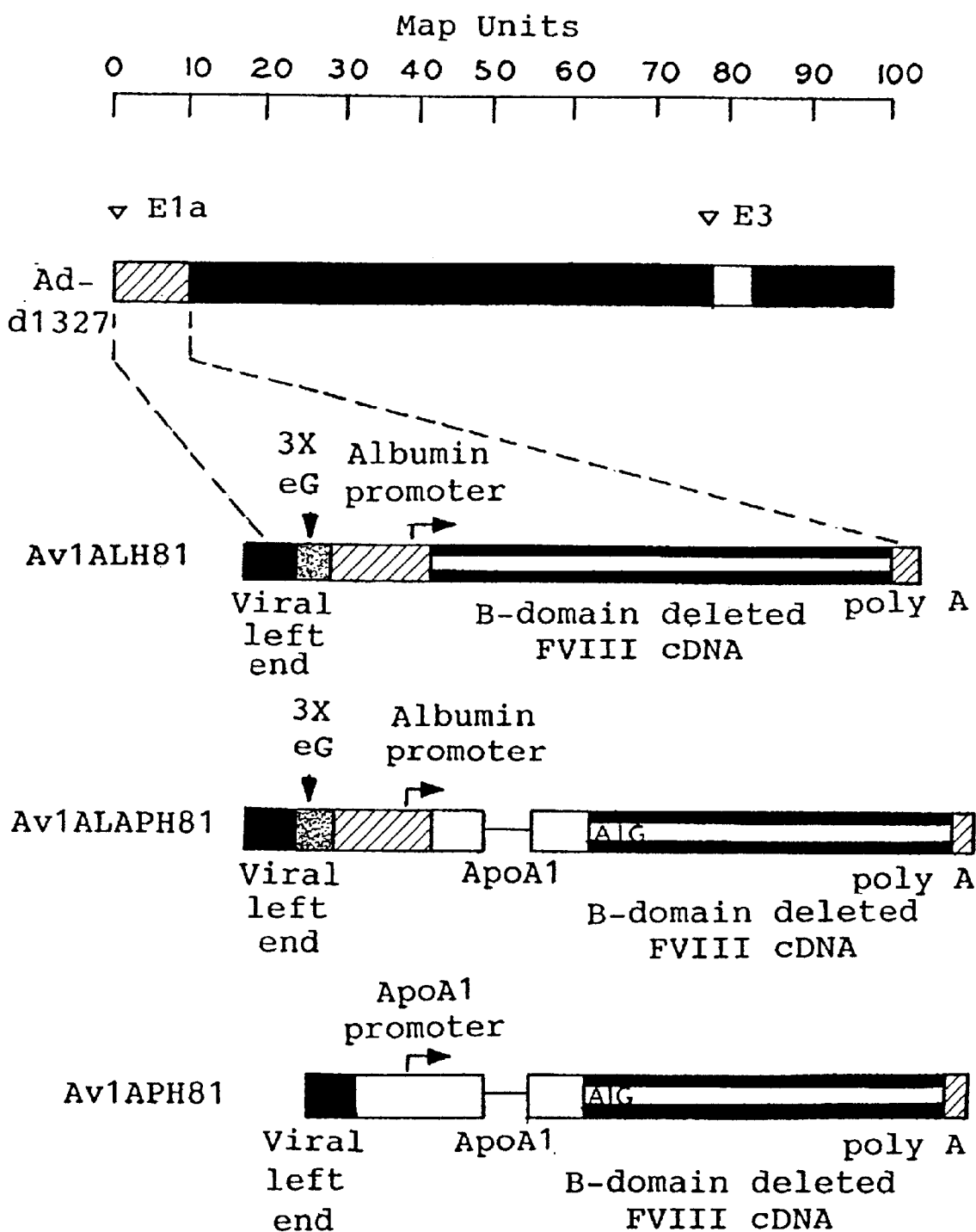
FIG. 23 is a schematic of adenoviral vectors Ad5-dl327, Av1ALH81, and Av1ALAPH81.

The recombinant adenoviral vector Av1ALAPH81 was generated as outlined in FIG. 23. 2×10$^6$ 293 cells were cotransfected in a 100 mm tissue culture dish with 10 μg of the undigested shuttle plasmid, pAvALAPH81 (FIG. 20). Generation of adenoviral vector Av1ALAPH81 then was carried out in the same manner as the generation of adenoviral vector Av1ALH81. Av1APH81 can be generated in the same manner.

EXAMPLE 7

In Vivo Expression of Adenoviral Vectors Including DNA Encoding Factor VIII Plus Genomic Elements A. Factor VIII Tri-Sandwich ELISA Before Av1ALH81 could be tested for Factor VIII expression in vivo, in mice, or in vitro, in tissue culture cells, it was necessary to develop an assay capable of measuring low levels of human Factor VIII present in mouse plasma. The only commercially available Factor VIII assay, Coatest (Kabi Pharmaceuticals) measures the biological activity of Factor VIII protein, and can be used to measure Factor VIII levels in tissue culture cells. However, Coatest cannot distinguish human Factor VIII from animal Factor VIII and, therefore, is not useful for measuring human Factor VIII in animal plasma. To measure the amount of human Factor VIII present in tissue culture medium or animal plasma samples, a quantitative Factor VIII tri-sandwich ELISA was developed. This ELISA can measure human Factor VIII specifically in mouse and dog plasma, and can measure reproducibly Factor VIII concentrations down to 1.0 ng/ml. The assay is performed as follows.

Figure 24:
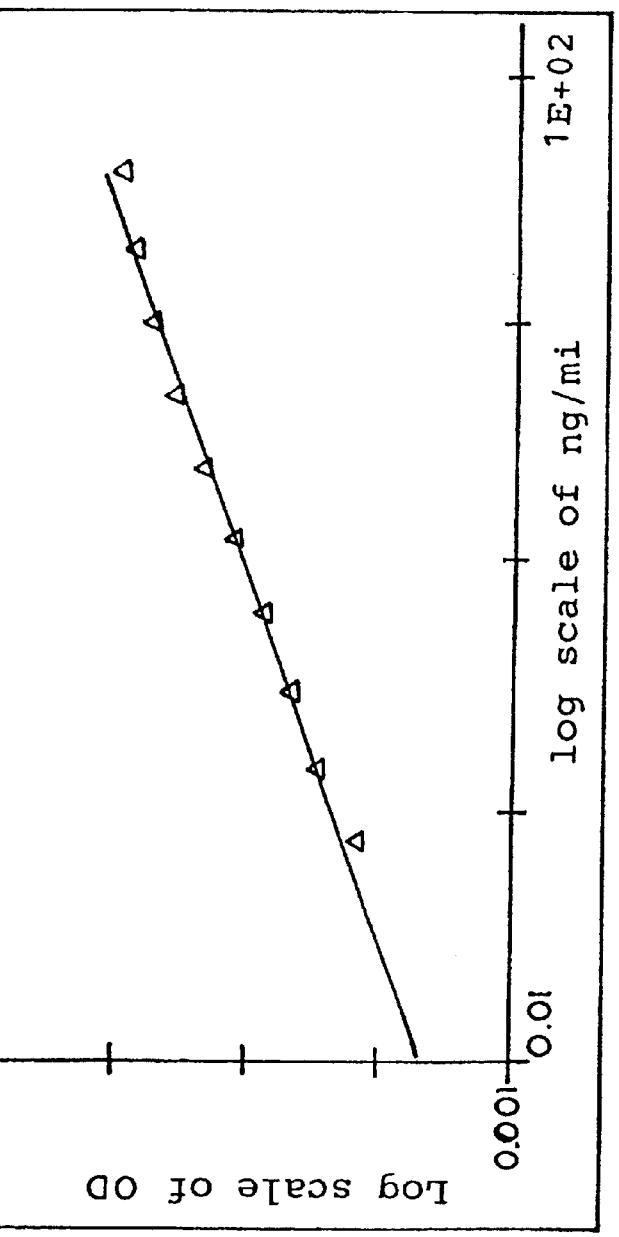
FIG. 24 is a standard log-log curve of a human Factor VIII—specific ELISA assay.

A 96 well microtiter plate is coated with two commercially available monoclonal antibodies with unique epitopes for Factor VIII protein and incubated overnight at 4° C. to allow adherence to the plastic wells. 0.5 ug of each antibody (N7, Biodesign; and ESH2, American Diagnostica) were diluted in dilution buffer (1.59 g $Na_2CO_3$, 2.93 g $NaHCO_3$, sterile $H_2O$ to one liter, pH 9.6), and 100 µl of the dilution was added to each well. These antibodies constitute the primary antibody. The use of two capture antibodies, that act cooperatively to increase the sensitivity of the assay, has not been described previously. After the overnight incubation, the plate is washed gently 3x with 200 µl per well of 1xPBS and blotted dry. Blocking agent [1xPBS, 10% Horse Serum (heat inactivated, BioWhittaker), and 1 mm $CaCl_2$] is added, and incubated for two hours at room temperature, after which the plate is washed with 200 µl per well of washing solution [1xPBS, 0.05% Tween 20 (Sigma)] 3x and blotted dry. Samples then are diluted appropriately (usually a 5-fold dilution) in TNTC (50 mm Tris pH 7.2, 5 mm $CaCl_2$, 0.1% Tween 20, 0.5 M NaCl), aliquoted into each well, and incubated for one hour at 37° C., after which the wells are washed with the washing solution as described. The secondary antibody, which is diluted serum from a hemophiliac (a 1:1000 dilution in the blocking agent solution, 100 µl per well) containing Factor VIII inhibitor antibodies, is added and allowed to bind for one hour at 37° C., after which the wells are washed with the washing solution as described. The third antibody, a commercially available goat anti-human IgG antibody conjugated to horseradish peroxidase (goat anti-human IgG-HRP, Pierce, 0.8 mg/ml, diluted 1:5000 in blocking agent, 100 µl per well), is added, and incubated for one hour at 37° C. The excess antibody then is washed out of the wells (as described, but 5x) and the substrate tetramethylbenzidine (TMB) (Kirkegaard and Perry Labs; 100 µl of the commercially available solution), which when cleaved by the HRP, yields a blue color, is added to each well. The level of color that develops is proportional to the amount of Factor VIII present in the sample. The reaction is stopped, after 2–3 minutes with an acid stop solution (TMB stop solution, Kirkegaard and Perry Labs, 100 µl per well) and the absorbance is determined using a microtiter plate reader. An example of a typical standard curve, using full-length human Factor VIII protein concentrations ranging from 0.078 ng/ml to 40.00 ng/ml is displayed in FIG. 24.

B. Half-Life Study of B-Domain Deleted Factor VIII in Mouse Plasma

After development of this extremely sensitive Factor VIII ELISA, a half-life study of B-domain deleted (BDD) Factor VIII in mouse plasma was undertaken. It had been reported (Hoeben et. al., 1993) that the half-life of human Factor VIII in mice was only one hour, compared to the 10 to 12 hour half-life of full-length human Factor VIII in humans and dogs (Brinkhous et al., *PNAS,* Vol. 82, pgs. 8752–8756 (1985)). The determination of the half-life of BDD human Factor VIII in mice was important for the subsequent evaluation of the efficacy of Av1ALH81 for gene therapy protocols utilizing the mouse as an in vivo model.

Figure 25:
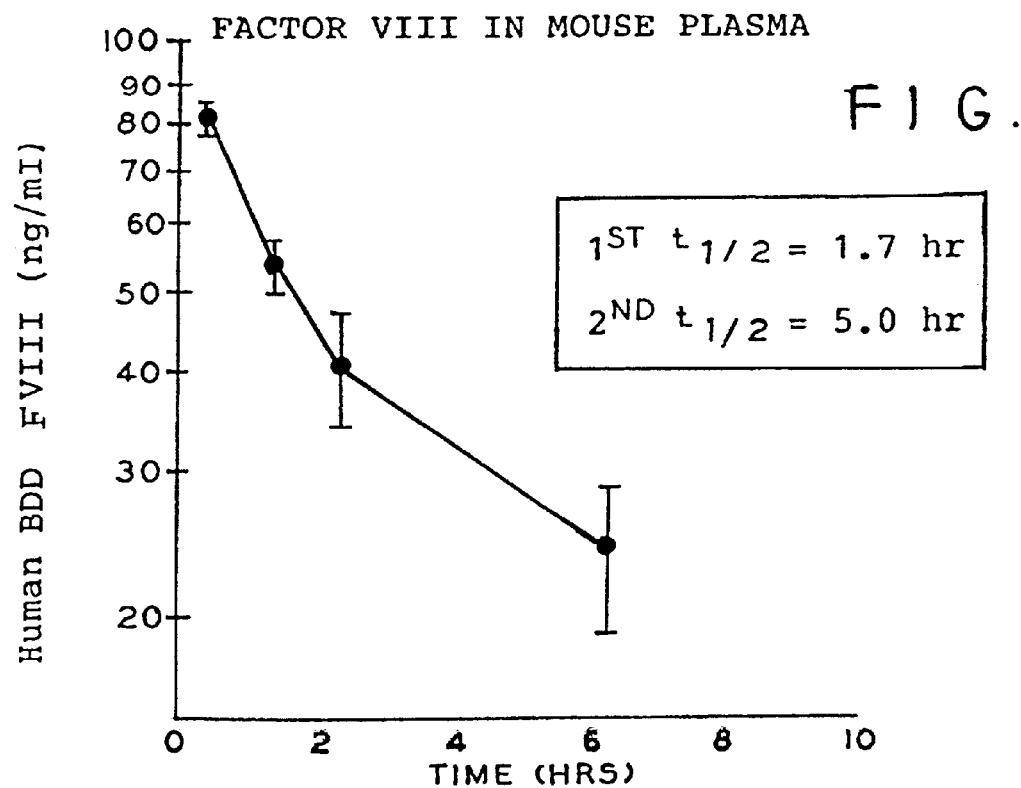
FIGS. 25 and 26 are graphs of the amounts of human Factor VIII in mouse plasma over time in two separate experiments.
Figure 26:
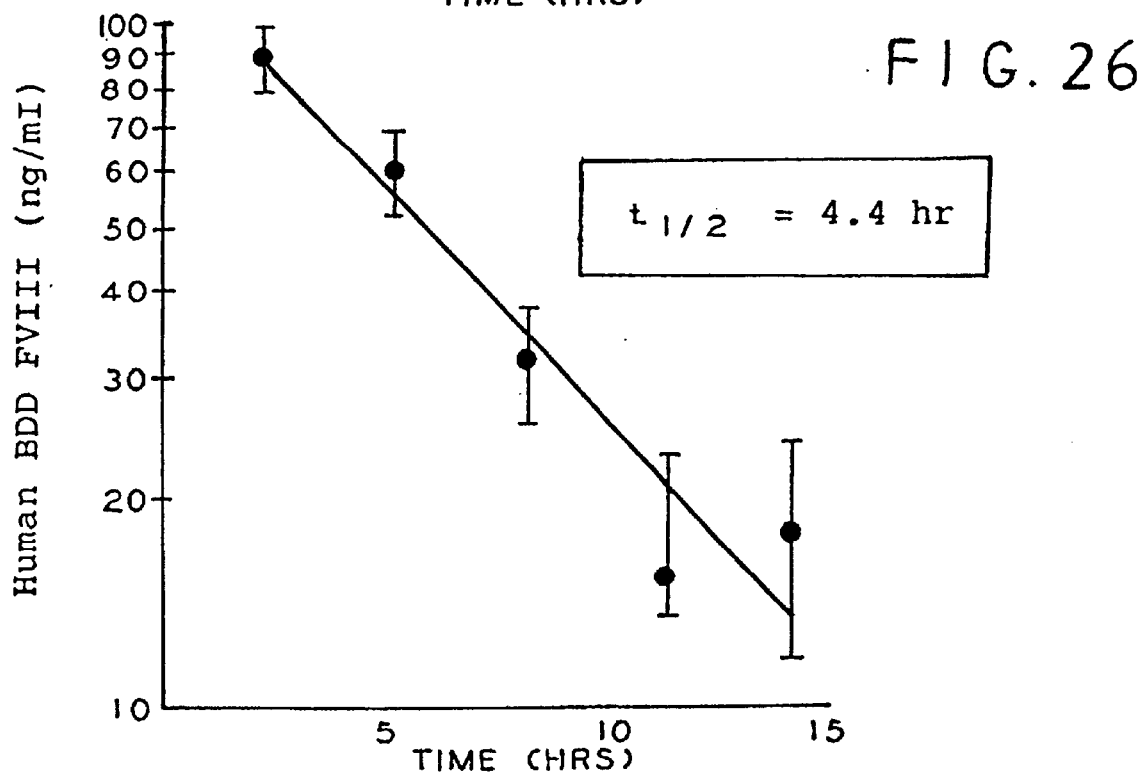

The half-life study was performed twice. In the first experiment (FIG. 25) five C57bl/6 female mice were injected via tail vein with 400 ng of BDD Factor VIII protein. Blood was drawn at 0.5, 1.5, 2.5. and 6.5 hours post injection. In the second experiment (FIG. 26), designed to focus on the 2 to 14 hour post injection time range, four C57bl/6 female mice were injected via tail vein, with 500 ng of BDD Factor VIII. Blood was drawn at 2, 5, 8, 12, and 14 hours post injection and plasma analyzed for the presence of human Factor VIII antigen. The results are displayed in FIGS. 25 and 26. The half-life of human Factor VIII in mice was calculated to be 4–5 hours. This result contrasts with the half-life calculated by Hoeben et. al. (1993). However, in the study by Hoeben et. al. (1993), the half-life of Factor VIII in mice was analyzed over only a 2 hour time period. In the study reported here, it was found that there was a sharp decrease (half-life 1.7 hours) in the level of Factor VIII antigen in mouse plasma between 30 minutes and 2 hours post injection (FIG. 25), with the decay leveling off to a half-life of 4–5 hours at subsequent time points (FIGS. 25 and 26). Therefore, the results indicate that the half-life of human BDD Factor VIII in mice is approximately 2–3 times shorter than the human Factor VIII half-life in humans and dogs.

C. Production of Biologically Active Factor VIII In Vitro

To determine if Av1ALH81 transduction resulted in the production of biologically active Factor VIII in vitro, 293 cells were infected with CVL-1, generated from two separate plaques of plaque-purified Av1ALH81 as follows. The medium was removed from 3–150 mm plates of 293 cells containing 1.5×10$^7$ cells, and replaced with 1.15 mls of Infection Medium, plus 100 µl of CVL-1 from either Av1ALH81 plaque (plaque 1 or plaque 2), or, for the negative control plate, 1.25 mls of Infection Medium. Plates were rocked for 1.5 hrs. as described, after which 20 mls of complete medium was added to each plate. 1.0 ml of medium was collected from each plate at 0, 12, and 24 hr. time points, and analyzed for the presence of Factor VIII antigen, using the human Factor VIII-specific ELISA, described above, and analyzed for biological activity, using the Coatest Assay (Kabi Pharmaceuticals). The results are displayed in Table II below.

TABLE II

Expression of Factor VIII in Av1ALH81 Transduced 293 Cells

| | | Assay | |
|---|---|---|---|
| Virus | Time (hrs) | ELISA (ng/ml) total antigen | Coatest (ng/ml)* biological activity |
| Av1ALH81 plaque 1 | 0 | 0.0 | 0.0 |
| | 12 | 9.8 | 6.9 |
| | 24 | 10.2 | 1.0 |
| Av1ALH81 plaque 2 | 0 | 0.0 | 0.0 |
| | 12 | 22.1 | 7.6 |
| | 24 | 24.3 | 0.0 |
| No virus | 0 | 0.0 | 0.0 |
| | 12 | 0.0 | 0.0 |
| | 24 | | 0.0 |

*converted from units in which one unit of activity equals 200 ng/ml of Factor VIII.

As shown, in Table II, the cells produced 10–20 ng/ml of Factor VIII total antigen as determined by ELISA, and at 12 hrs., 7 ng/ml of Factor VIII was biologically active. However, by 24 hours, the biological activity was lost. The lower level of biologically active Factor VIII at 12 hours and the lack of active Factor VIII at 24 hours can be explained by the fact that the cells were undergoing a cytopathic effect that started at 12 hours and was complete by 24 hours.

Therefore, de novo synthesis of Factor VIII had probably begun to decrease at 12 hours and the Factor VIII present in the medium was becoming degraded by 24 hours.

D. In Vivo Expression of BDD Factor VIII From Av1ALH81

Figure 27:
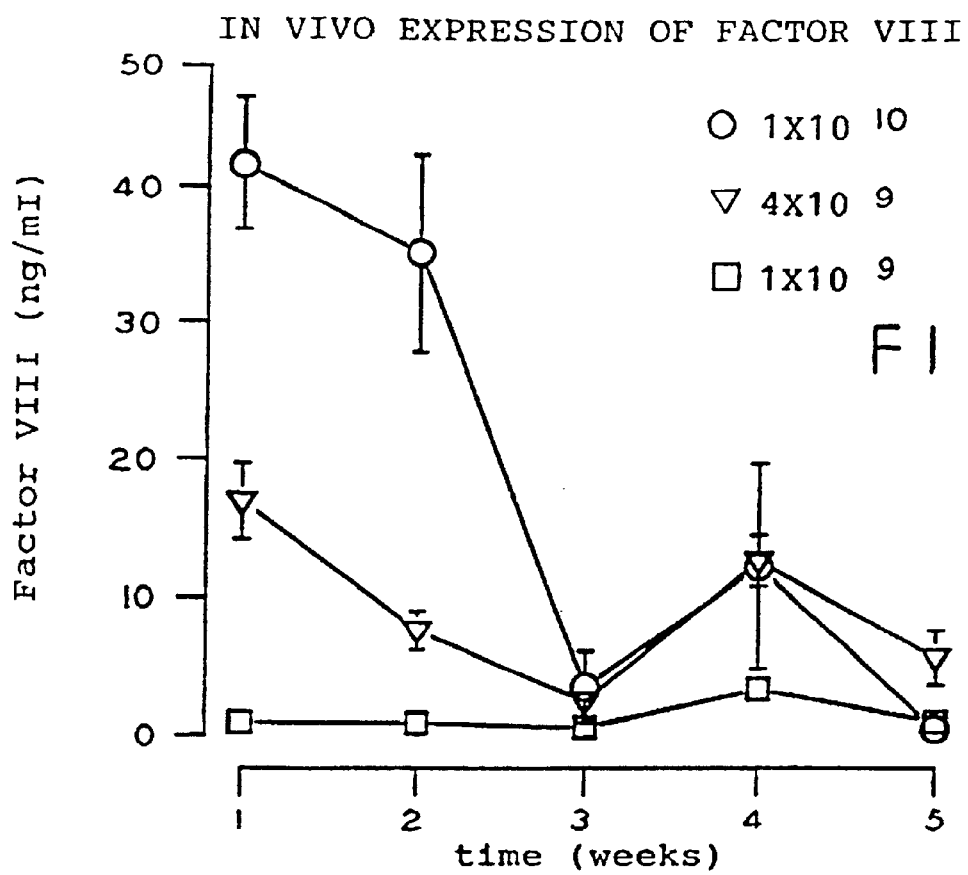
FIG. 27 is a graph of in vivo expression of human Factor VIII in mouse plasma over time after injection of various doses of Av1ALH81.

To determine if human BDD Factor VIII was expressed from Av1ALH81 in vivo, and if so, to follow the time course of Factor VIII expression, 15 C57bl/6 female mice were injected with Av1ALH81. The virus was diluted in injection medium (IMEM +1% FBS) to a total volume of 0.5 ml. Five mice received a dose of $1 \times 10^{10}$ pfu (67 μl of virus; concentration of $1.5 \times 10^{11}$ pfu/ml), five mice received a dose of $4 \times 10^9$ pfu (27 μl virus) and five mice received $1 \times 10^9$ pfu (7 μl virus). The viral suspension was infused via tail vein over a ten second period using a 0.5 ml syringe and a 27 gauge needle. The control mouse received no injection. One mouse that received $1 \times 10^{10}$ pfu of Av1ALH81 died two days after injection. Blood was taken from each mouse at one week intervals and analyzed for the presence of human Factor VIII antigen by ELISA. The results of the analysis, for the first five weeks post injection, is displayed in Table III below, and graphically in FIG. 27.

TABLE III

In Vivo Expression of Factor VIII

| Mouse | Virus Dose | ELISA (Factor VIII ng/ml) | | | | |
| --- | --- | --- | --- | --- | --- | --- |
| | | Week 1 | Week 2 | Week 3 | Week 4 | Week 5 |
| 1 | $1 \times 10^{10}$ | 53.3 | 19.3 | 0.0 | 4.3 | 0.0 |
| 2 | $1 \times 10^{10}$ | 45.9 | 54.6 | 0.0 | 34.3 | 0.0 |
| 3 | $1 \times 10^{10}$ | 34.5 | 35.3 | 3.0 | 2.6 | 0.0 |
| 4 | $1 \times 10^{10}$ | 33.1 | 31.1 | 10.9 | 7.7 | 1.8 |
| Mean | — | 41.7 | 35.1 | 3.5 | 12.2 | 0.5 |
| 5 | $4 \times 10^9$ | 18.9 | 7.3 | 0.0 | 14.9 | 1.1 |
| 6 | $4 \times 10^9$ | 13.0 | 6.2 | 5.1 | 7.9 | 3.1 |
| 7 | $4 \times 10^9$ | 9.8 | 5.2 | 3.1 | 12.4 | 5.1 |
| 8 | $4 \times 10^9$ | 25.9 | 13.1 | 3.4 | 18.4 | 12.9 |
| 9 | $4 \times 10^9$ | 17.1 | 5.9 | 0.5 | 9.7 | 6.0 |
| Mean | — | 16.9 | 7.5 | 2.3 | 12.6 | 5.6 |
| 10 | $1 \times 10^9$ | 0.8 | 0.0 | 0.0 | 3.6 | 0.8 |
| 11 | $1 \times 10^9$ | 0.4 | 0.0 | 0.5 | 5.1 | 0.3 |
| 12 | $1.10^9$ | 1.1 | 1.6 | 2.2 | 4.2 | 2.5 |
| 13 | $1 \times 10^9$ | 1.0 | 1.7 | 0.0 | 1.7 | 1.3 |
| 14 | $1 \times 10^9$ | 1.4 | 0.9 | 0.0 | 1.9 | 0.0 |
| Mean | — | 0.9 | 0.9 | 0.5 | 3.3 | 1.0 |
| Control | 0 | 0.0 | 0.0 | 0.0 | 0.0 | 0.0 |

The mice receiving the highest viral dose ($1 \times 10^{10}$ pfu) were producing 42 and 35 ng/ml human BDD Factor VIII one and two weeks post injection, respectively. If these values are corrected for the difference in half-life of human Factor VIII in mice (4–5 hrs., see above) compared to humans (10–12 hrs.), levels in the plasma are adjusted to 126 and 96 ng/ml of Factor VIII at one and two weeks, respectively. Physiological levels of Factor VIII in humans is ~100–200 ng/ml and therapeutic levels are ~10 ng/ml. Therefore, these mice are producing physiological levels of Factor VIII. In addition, the mice that received the lower dose of $4 \times 10^9$ pfu of Av1ALH81 are producing Factor VIII protein well over therapeutic levels. The expression of human Factor VIII, in an animal model, has never before been demonstrated.

Figure 28:
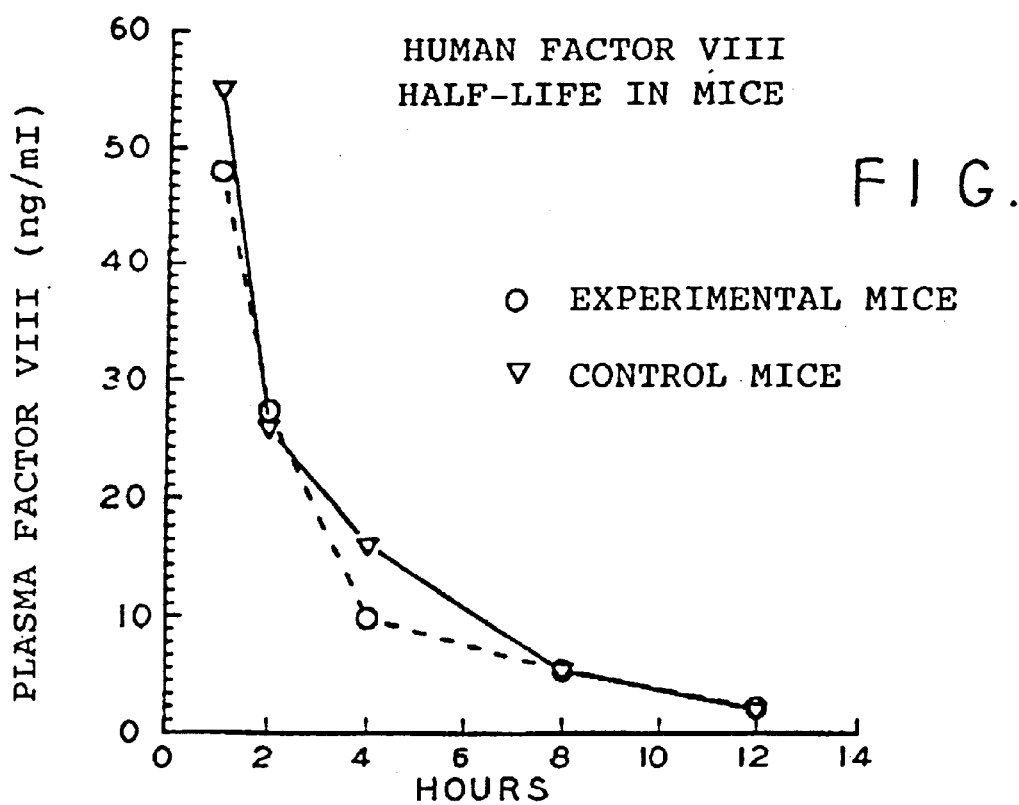
FIGS. 28 and 29 are graphs of human Factor VIII half-life in experimental mice and control mice.
Figure 29:
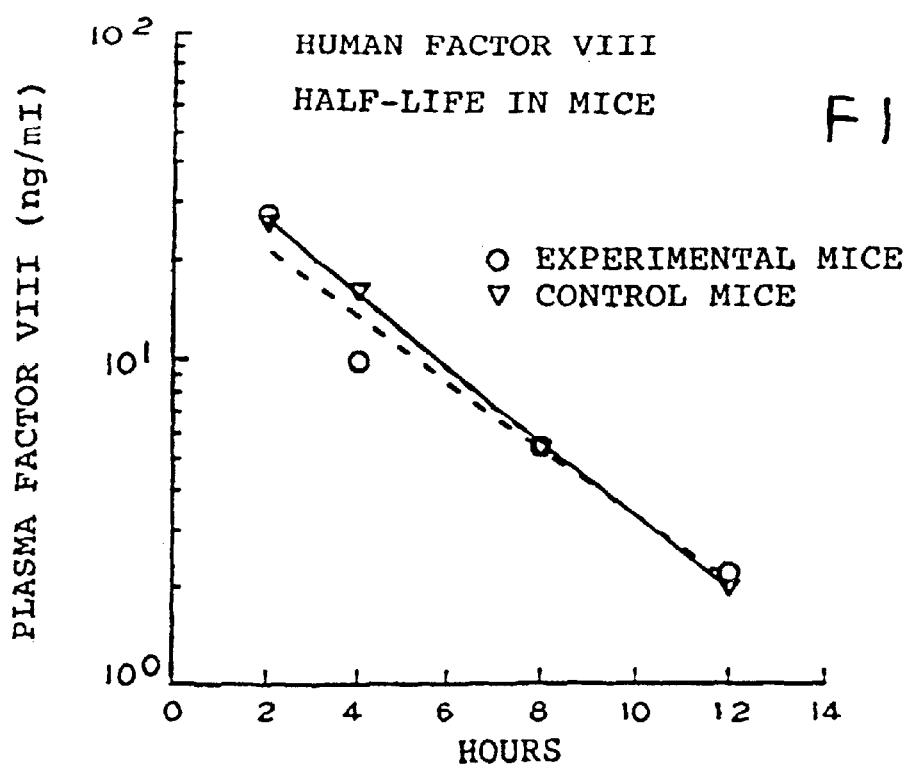

Three to five weeks post injection, however, the Factor VIII levels had decreased significantly. To determine if this decrease in Factor VIII expression at three weeks was due to an immunological response to the Factor VIII antigen, a second half-life study was performed using full-length human Factor VIII protein. The four mice that had received the highest viral dose ($1 \times 10^{10}$ pfu), and four control mice were injected, via tail vein, with 500 ng of full-length human Factor VIII. Blood was drawn at 1, 2, 4, 8, and 12 hours post injection and analyzed for the presence of human Factor VIII antigen by ELISA. FIGS. 28 and 29 display the results of this analysis. The half-life of full-length Factor VIII is similar in both sets of mice, and can be calculated to be about 3.0 hrs. Two conclusions can be drawn from these data: 1) The half-life of full-length Factor VIII and BDD Factor VIII in mouse plasma are comparable, 3 hrs. and 4–5 hrs., respectively, and 2) the loss in Factor VIII expression in the mice at 3 weeks is not due to rapid clearance of the Factor VIII by specific antibodies in mouse plasma, and, therefore, may be due to the loss of vector from the liver (or loss of the cells containing the vector), or reduced transcription of the Factor VIII cDNA.

Figure 30:
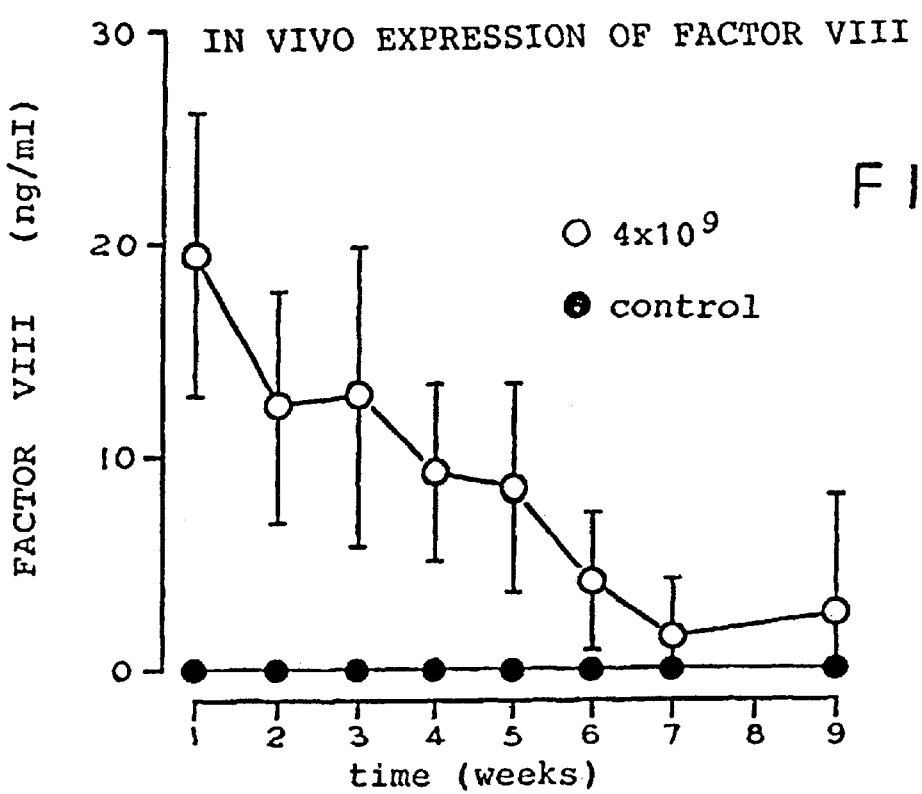
FIG. 30 is a graph of in vivo expression of human Factor VIII in mice given $4 \times 10^9$ pfu of Av1ALH81.

The time course of Factor VIII expression in mice was repeated, and the data are shown in FIG. 30.

EXAMPLE 8

Fifteen C57bl/6 female mice were injected via tail vein $4 \times 10^9$ pfu (27 μl of virus) of Av1ALH81 in injection medium (IMEM+1% FBS). The viral suspension was infused via the tail vein over a ten second period using a 0.5 ml syringe and a 27 gauge needle. A control mouse received no injection. Blood was taken from each mouse at one week intervals and analyzed for the presence of human Factor VIII antigen by ELISA. The results are shown graphically in FIG. 30.

EXAMPLE 9

Construction of Adenoviral Vectors Including Factor IX Sequences with Genomic Elements Vectors were prepared in which the Factor IX sequences incorporated genomic elements, i.e., sequences from the human Factor IX gene. These elements included the 5' untranslated region, a centrally truncated first intron, the full 3' untranslated region and naturally-occurring polyadenylation site. The 5' genomic elements were obtained by PCR amplication using genomic Factor IX clones as templates. The three prime untranslated region was obtained from a plasmid provided by Dr. Hsueh (Shanghai, China). An alternative approach, which can be used to readily obtain these elements, is to PCR amplify them from human genomic DNA.

Figure 31:
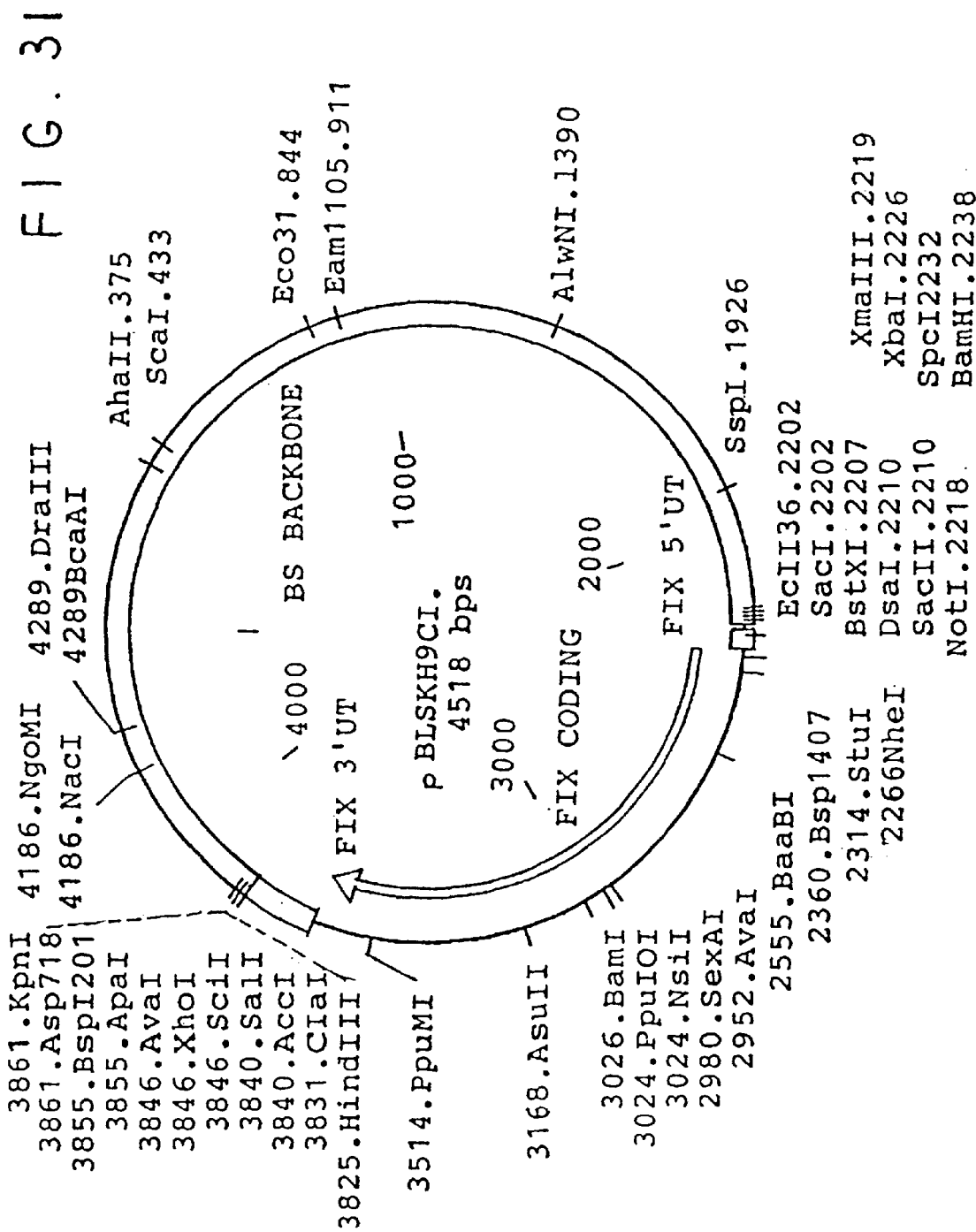
FIG. 31 is a map of plasmid pBLSKH9CI.

A Factor IX sequence, which includes 9 bp of the Factor IX promoter, the 5' untranslated region, the coding region, and a 162 bp segment of the 3' untranslated region, was excised from pKG5IX-2 (obtained from George Brownlee, University of Oxford, Oxford England) as a Bam HI to HindIII fragment. This fragment is described further in Anson et al., Nature, Vol. 315, pgs. 683–685 (1985). This insert was inserted into the polylinker of pBluescript II SK+ (Stratagene) to form BLSKH9CI. (FIG. 31). The Factor IX sequences were sequenced completely and verified to be correct. Factor IX DNA with genomic elements could also have been obtained according to the procedures disclosed in U.S. Pat. No. 4,994,371 and European Patent EP 0 107 278 B1.

Figure 32:
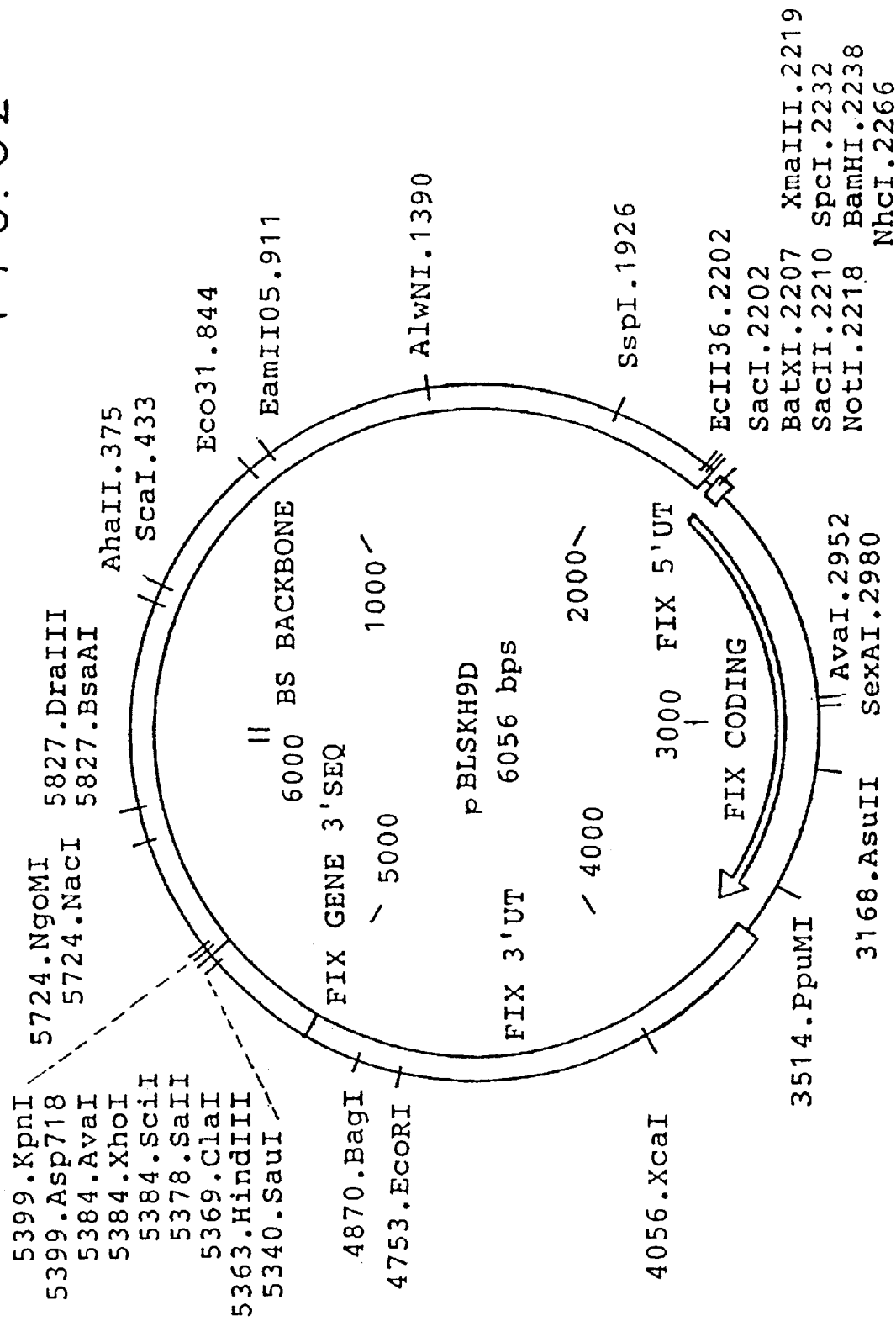
FIG. 32 is a map of plasmid pBLSKH9D.

A fragment containing the downstream part of the coding sequence, the full 3' untranslated region, the native Factor IX polyadenylation signal, and 331 bp past the polyadenylation site was excised from pCMVIXa (provided by Jerry Hsueh, Fudan University, Shanghai, China) with PpuMI and BglII. The BglII single strand overhang was blunted. pBLSKH9CI was cut with PpuMI and HindIII, the HindIII site was blunted, and the backbone fragment was joined to the fragment obtained from pCMVIXa as a PpuMI-blunt ligation. The resulting plasmid, pBLSKH9D (FIG. 32), contains the 9 bp of promoter, 5' untranslated region, the entire Factor IX coding sequence, the full 3' untranslated region, natural polyadenylation signal, and 331 bp downstream from the polyadenylation signal.

Figure 33:
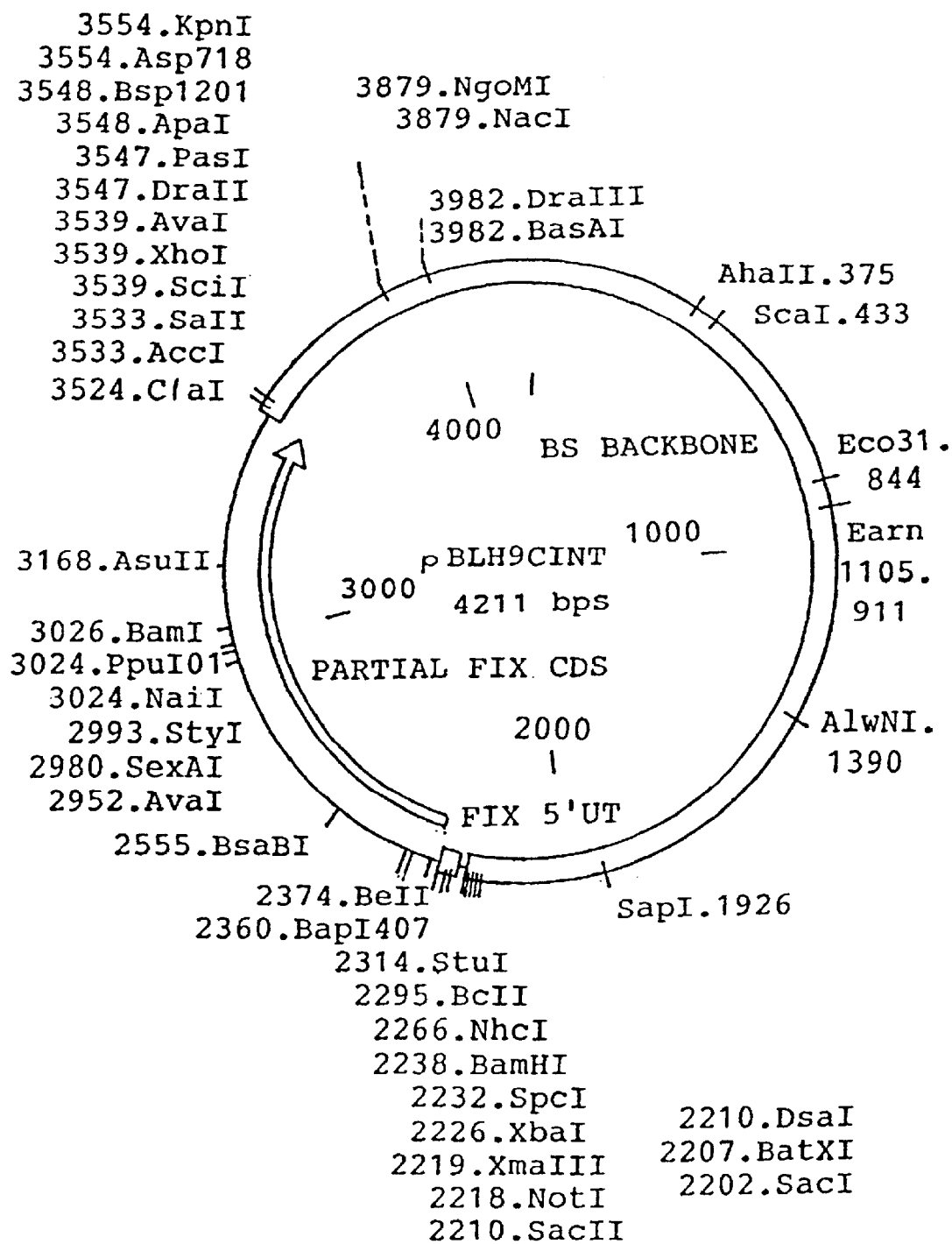
FIG. 33 is a map of Plasmid pBLH9CINT.

To generate constructs that contain a centrally truncated first intron, a cloning intermediate was prepared. This intermediate removed a BclI site downstream from the coding sequence to enable cloning into an upstream BclI site. The 3' end of the cDNA in pBlSKH9CI was removed from Ppu MI to HindIII. The single strand overhangs in the plasmid backbone were blunted and ligated to yield pBLH9CINT. (FIG. 33)

The 5' end of the cDNA in pBLH9CINT was modified to contain the centrally truncated first intron with a 3 way ligation using 2 PCR generated fragments. These fragments were generated using phage preps as templates (Yoshitake, S et al., 1985, *Biochemistry:* 24, 3736–3750). The two PCR generated fragments contained (5' to 3'):

1) SpeI site, SalI site, full 5' untranslated region, first exon of the Factor IX gene, the first 991 bp of the Factor IX first intron, and an AatII site.

2) AatII site, the last 448 bp of the Factor IX first intron, and part of the Factor IX second exon extending past the naturally occurring BclI site in the upstream part of this exon.

Figure 34:
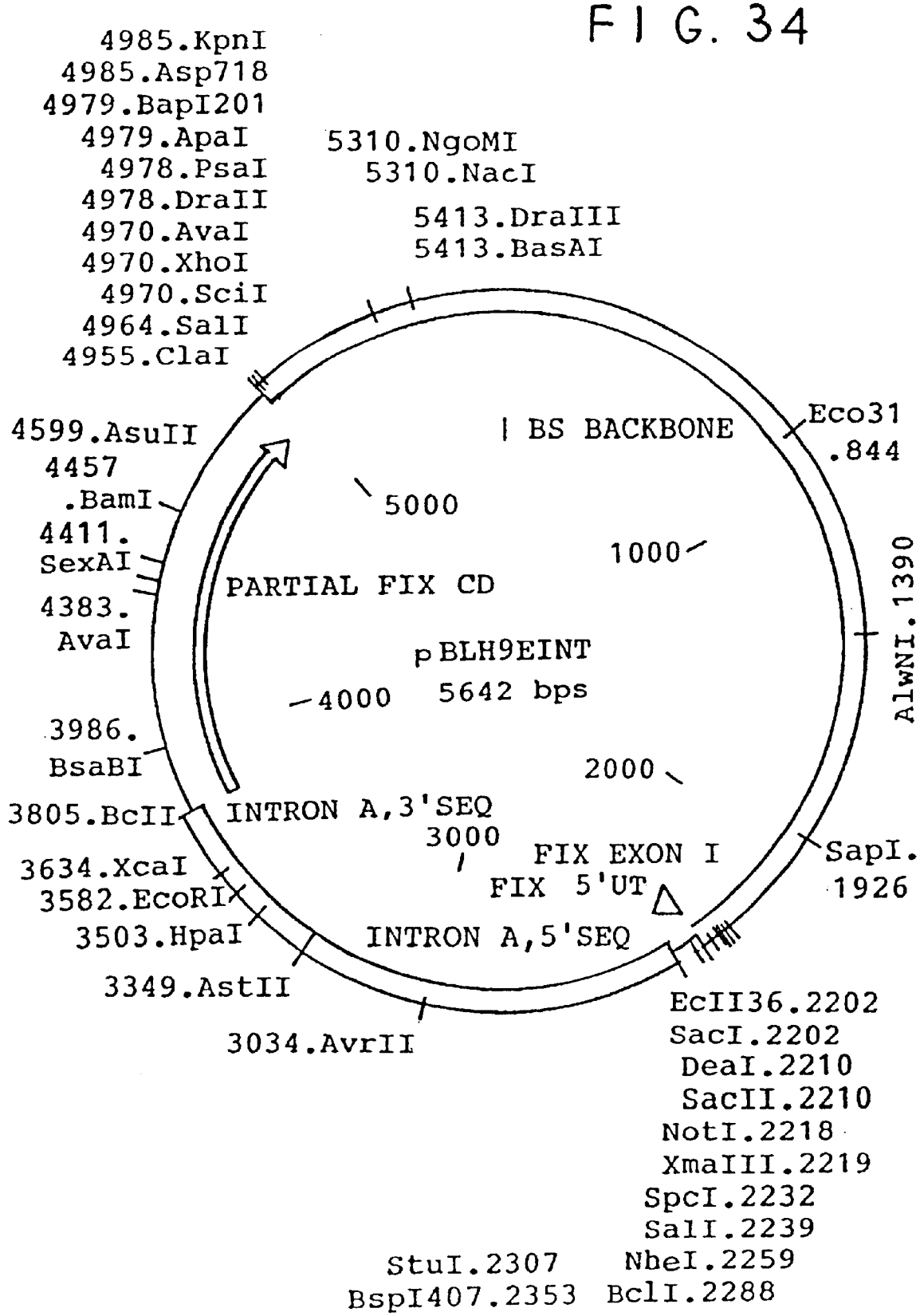
FIG. 34 is a map of plasmid pBLH9EINT.

PCR fragment 1 was digested with SpeI and AatII. PCR fragment 2 was digested with AatII and BclI. BLH9CINT was digested with SpeI and BclI and the backbone fragment was isolated. The three fragments were joined with a 3 way ligation to yield the plasmid pBLH9EINT. (FIG. 34) This plasmid contains the 5' untranslated region of Factor IX, the first exon, the centrally truncated first intron, and the coding sequence up to the PpuMI site.

Figure 35:
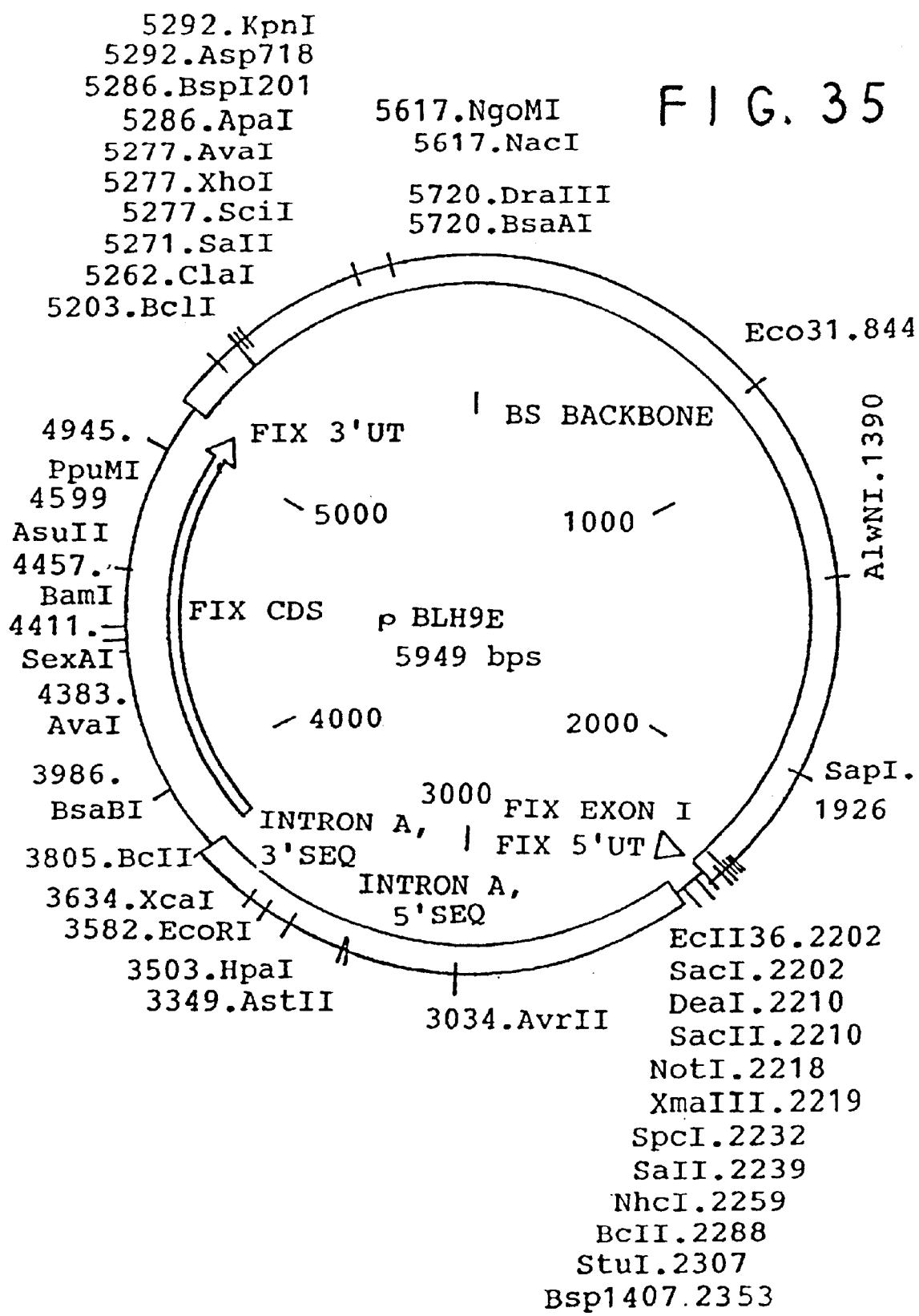
FIG. 35 is a map of plasmid pBLH9E.

To generate pBLH9E (FIG. 35), the 3' end of the coding sequence was re-inserted. The 3' end of the Factor IX sequence was excised from pBLSKH9CI and inserted into the pBLH9EINT backbone as an AvaI-AvaI fragment. The resulting plasmid pBLH9E (FIG. 35) contained the Factor IX 5' untranslated region, first exon, centrally truncated first intron, remainder of the coding sequence, and 162 bp of 3' untranslated region.

Figure 36:
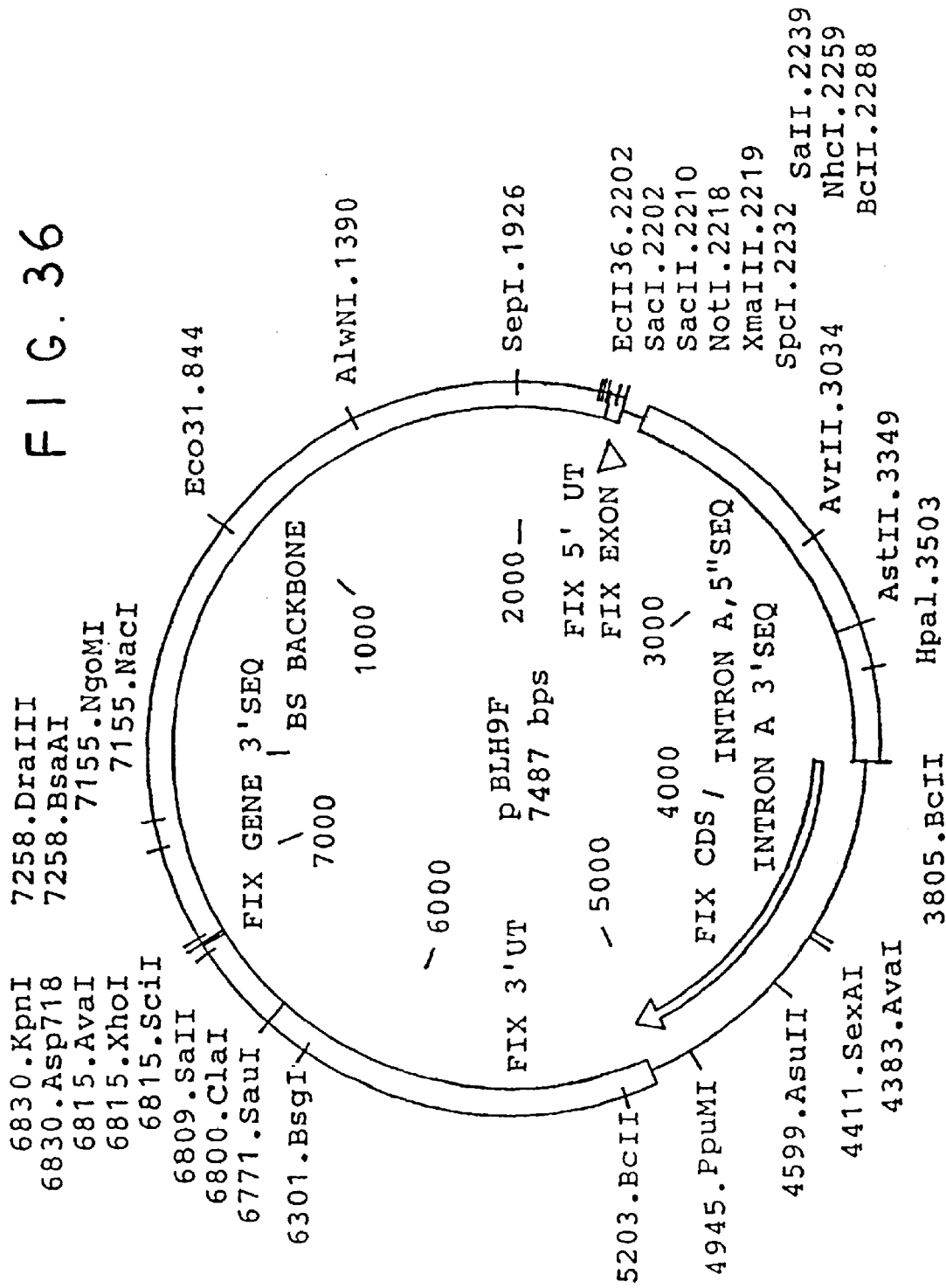
FIG. 36 is a map of plasmid pBLH9F.

To generate pBLH9F (FIG. 36), a fragment containing the 3' end of the coding sequence and the full 3' untranslated region was excised from pBLSKH9D and inserted into the pBLH9EINT backbone as an AvaI-AvaI fragment. Thus pBLH9F has the 5' untranslated region, first exon, truncated first intron, remainder of the coding sequence, full 3' untranslated region, and 300 bp downstream from the polyadenylation site.

Figure 37:
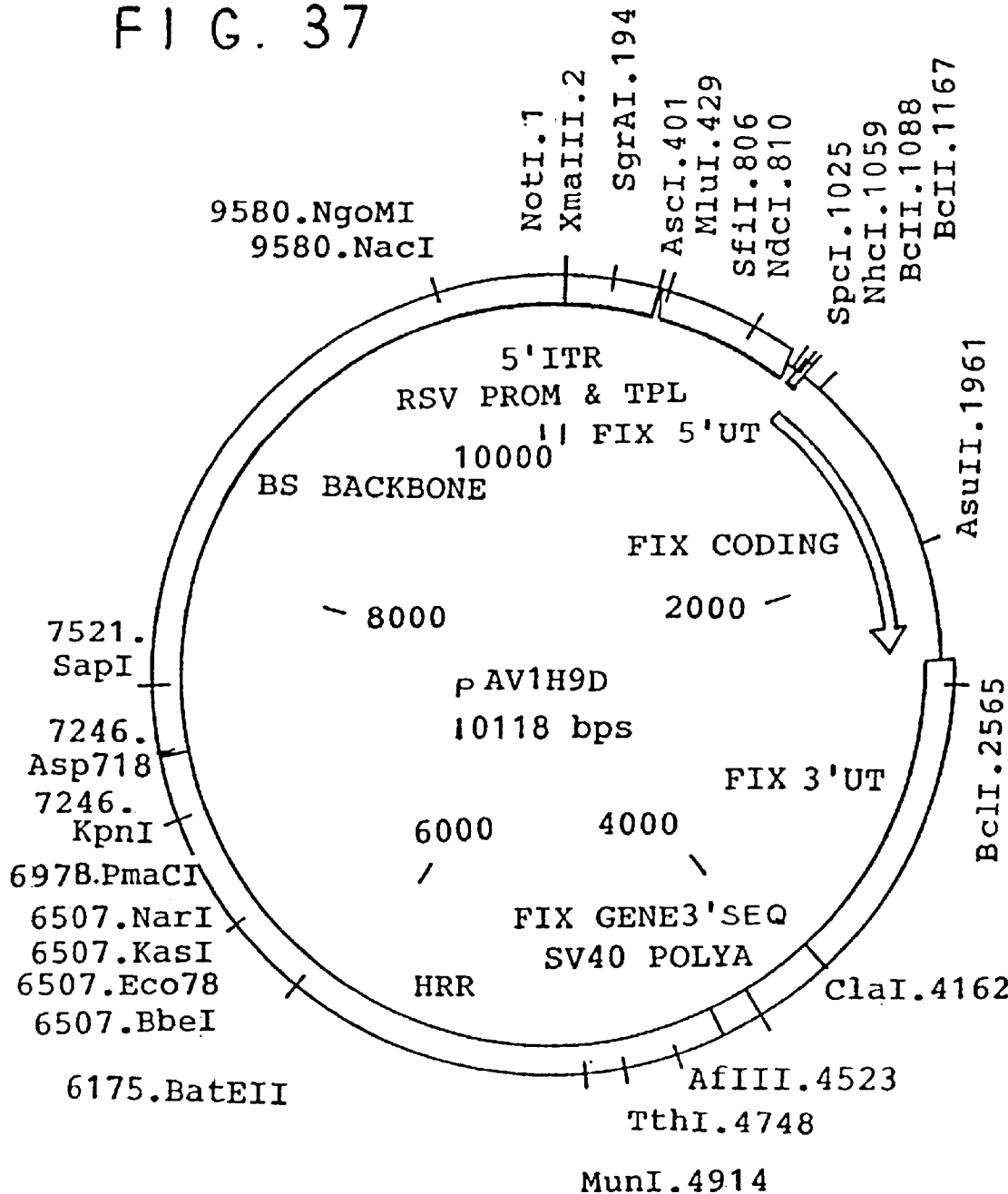
FIG. 37 is a map of plasmid pAV1H9D.
Figure 38:
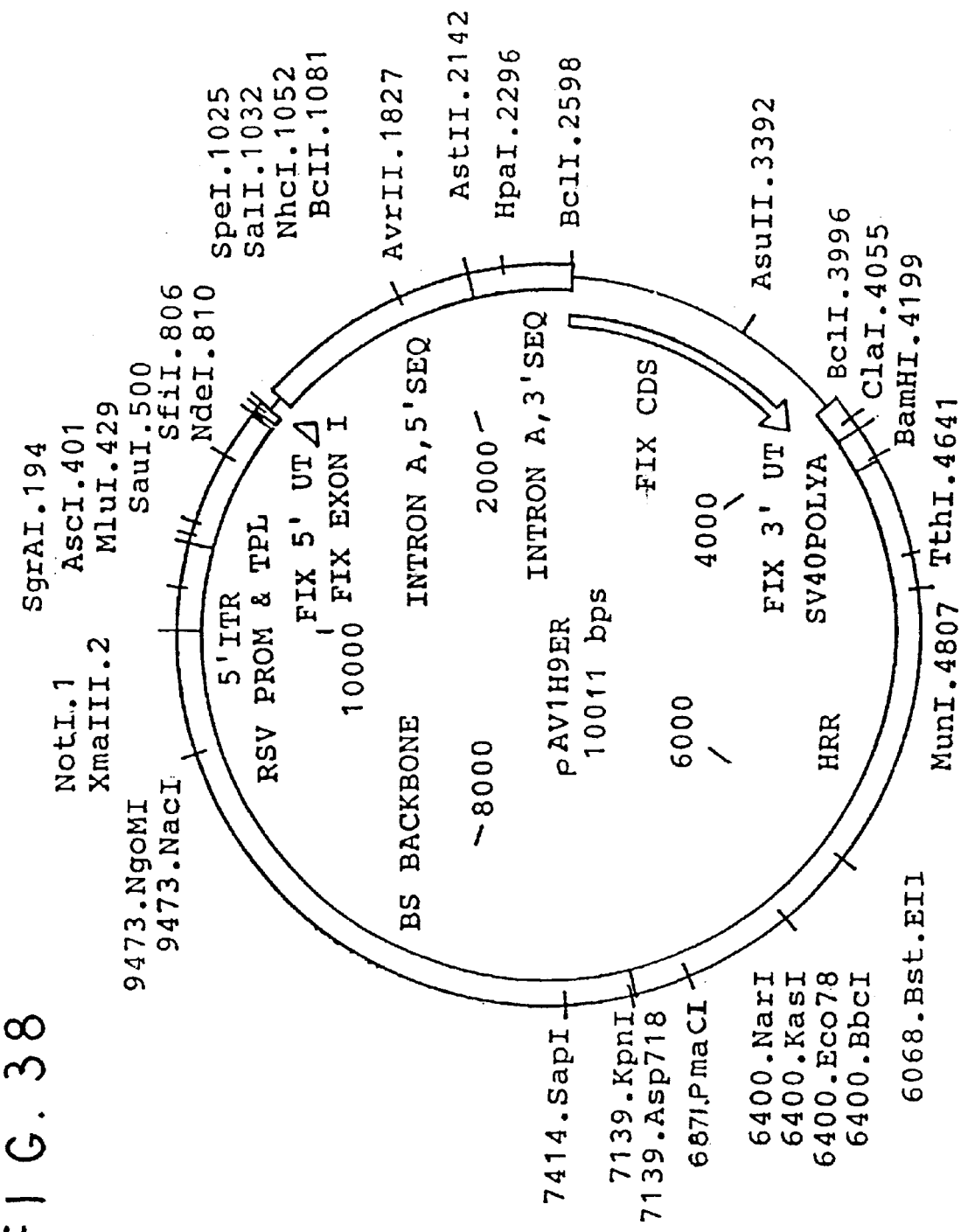
FIG. 38 is a map of plasmid pAV1H9ER.

The Factor IX sequences were then excised from pBLSKH9D, pBLH9E, and pBLH9F and inserted into the pAvS6 backbone as SpeI-ClaI fragments. The resulting plasmids were termed pAV1H9D (FIG. 37), pAV1H9E, and pAV1H9F, respectively. However, when pAv1H9E and pAv1H9F were sequenced, errors were found in the 5' untranslated region of the Factor IX gene. These errors were repaired. The sequence errors were traced back to pBLH9EINT. Miniprep one this plasmid had been used to generate the subsequent plasmids. pBLH9EINT miniprep six was found to have the correct sequence. The SpeI to AatII fragment in pBLH9EINT miniprep six was used to replace the corresponding fragment in pAv1H9E and pAv1H9F to yield pAv1H9ER (FIG. 38) and pAv1H9FR (FIG. 39), respectively. These plasmids contain the adenovirus type 5 ITR, RSV promoter, tripartite leader, Factor IX sequence, SV40 polyadenylation site (which is superfluous in pAV1H9D and pAV1H9FR), and adenovirus homologous recombination region. pAV1H9D, pAV1H9ER, and pAV1H9FR were then used to generate adenoviral vectors by procedures hereinabove described. Briefly, linearized plasmids were co-transfected with the large ClaI-cut fragment of Ad dl327 into 293 cells. Plaques were selected, expanded, and screened. The three vector isolates chosen were termed Av1H9D, Av1H9ER, Av1H9FR. These were grown into large scale preps and plaque titered on 293 cells.

EXAMPLE 10

Figure 40:
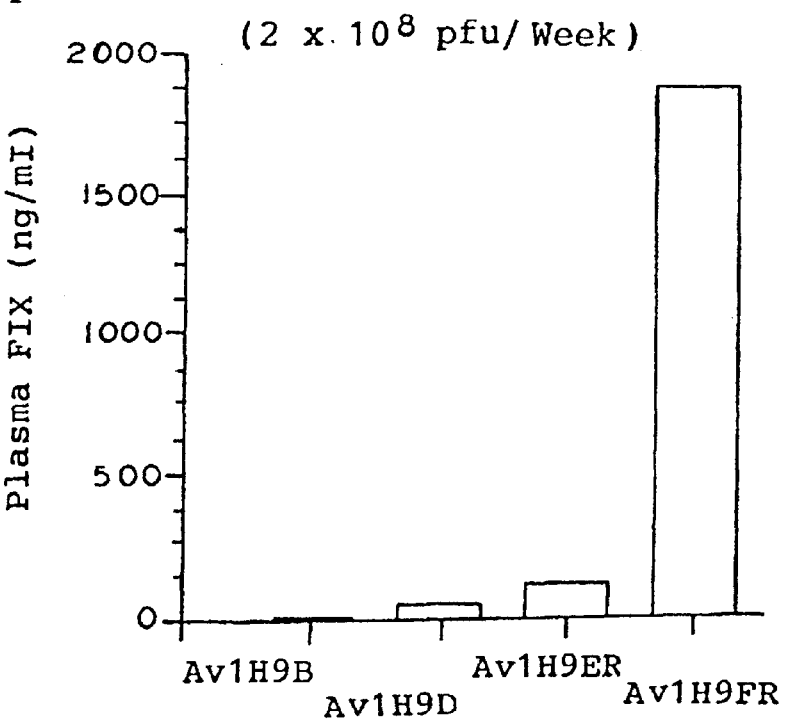
FIG. 40 is a graph of Factor IX expression in mice treated with Av1H9B, Av1H9D, Av1H9ER and Av1H9FR.

$2 \times 10^8$ pfu of Av1H9B, Av1H9D, Av1H9ER, or Av1H9FR were injected via tail vein into C57Bl/6 mice. Two mice received each virus. One week later, plasma was sampled by ELISA and an immunochromogenic bioassay described above for human Factor IX antigen and biological activity, respectively. The ELISA results, shown in FIG. 40, demonstrate that the inclusion of genomic elements dramatically increased Factor IX expression. The Av1H9FR vector effected the most expression which was more than 200 fold greater than the level obtained with Av1H9B. The immunochromogenic assay results for eight experimental mice and one negative control mouse (which was injected with the beta-galactosidase vector, Av1LacZ4) are shown in Table IV below.

TABLE IV

| Vector | Mouse Number | Plasma Factor IX (ng/ml) | |
| --- | --- | --- | --- |
| | | ELISA | Immunochromogenic |
| Av1H9B | 1 | <8 | <8 |
| Av1H9B | 2 | <8 | <8 |
| Av1H9D | 3 | 74 | 65 |
| Av1H9D | 4 | 48 | 49 |
| Av1H9ER | 5 | 116 | 102 |
| Av1H9ER | 6 | 101 | 80 |
| Av1H9FR | 7 | 1,339 | 1,051 |
| Av1H9FR | 8 | 1,467 | 1,391 |
| Av1LacZ4 | 9 | <8 | <8 |

These results demonstrate that the human Factor IX expressed from Av1H9D, Av1H9ER, and Av1H9FR was functional. Livers were collected one week after vector injection and DNA and RNA were prepared. Southern analysis demonstrated an average of 1–2 vector copies per liver cell for all four vectors. (Data not shown.) Northern analysis revealed RNA species of the correct size for each vector with band intensities that parallelled the Factor IX plasma levels. (Data not shown.)

EXAMPLE 11

Figure 41:
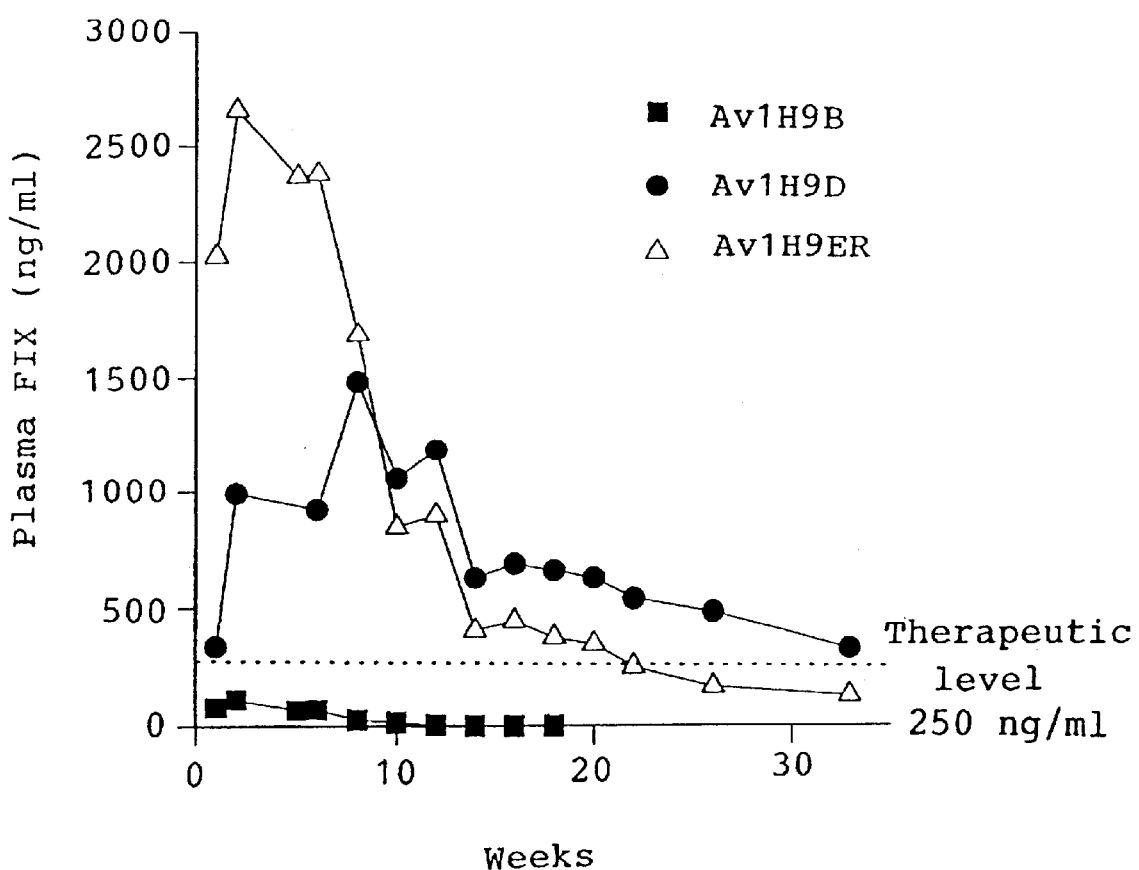
FIG. 41 is a graph of Factor IX expression in mice treated with $1 \times 10^9$ pfu of Av1H9B, Av1H9D, or Av1H9ER.
Figure 42:
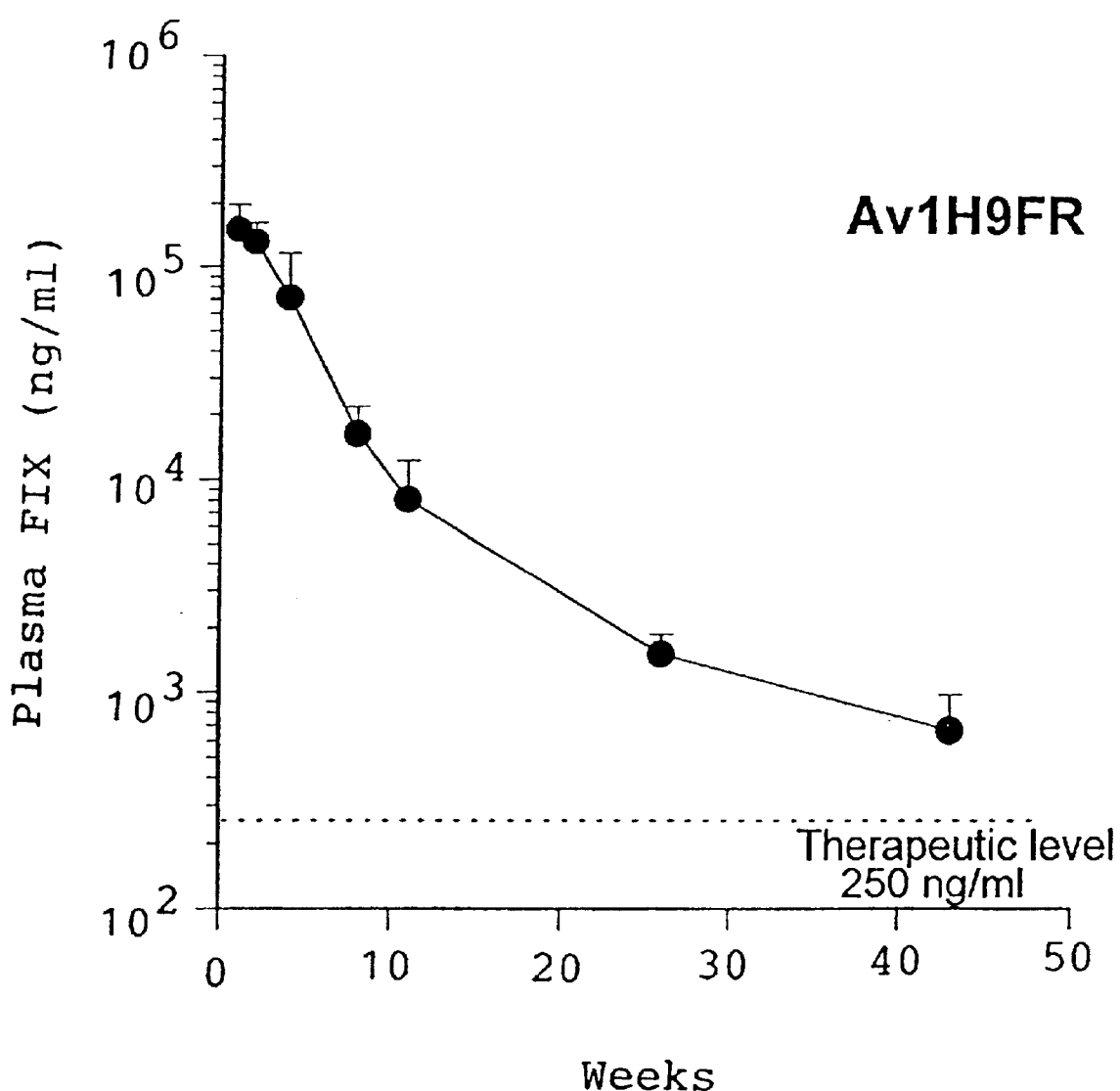
FIG. 42 is a graph of Factor IX expression in mice treated with $1 \times 10^9$ pfu of Av1H9FR.

Persistent High Level Expression of Human Factor IX in Mice With Vectors With Genomic Elements $1 \times 10^9$ pfu of Av1H9B, Av1H9D, or Av1H9ER were injected via tail vein into C57Bl/6 mice. $1 \times 10^9$ pfu of Av1H9FR were also administered to C57Bl/6 mice via tail vein injection. The cohort size for each regimen was 5 mice. At the indicated time points plasma was obtained and assayed for human Factor IX by ELISA. The results, shown in FIGS. 41 and 42, again demonstrate that the inclusion of genomic elements in the Factor IX sequences dramatically increased Factor IX expression. Factor IX levels that approach normal were obtained with the low dose of $1 \times 10^9$ pfu of Av1H9D and Av1H9ER, and Av1H9FR yielded very high suprahysiologic levels. In each case, high-level expression at or above the therapeutic level from Av1H9D, Av1H9ER, and Av1H9FR persisted for the 8 to 10 month duration of the experiment. This exceeded the 7 week duration of expression which had previously been achieved with higher doses of Av1H9B.

EXAMPLE 12

Figure 43:
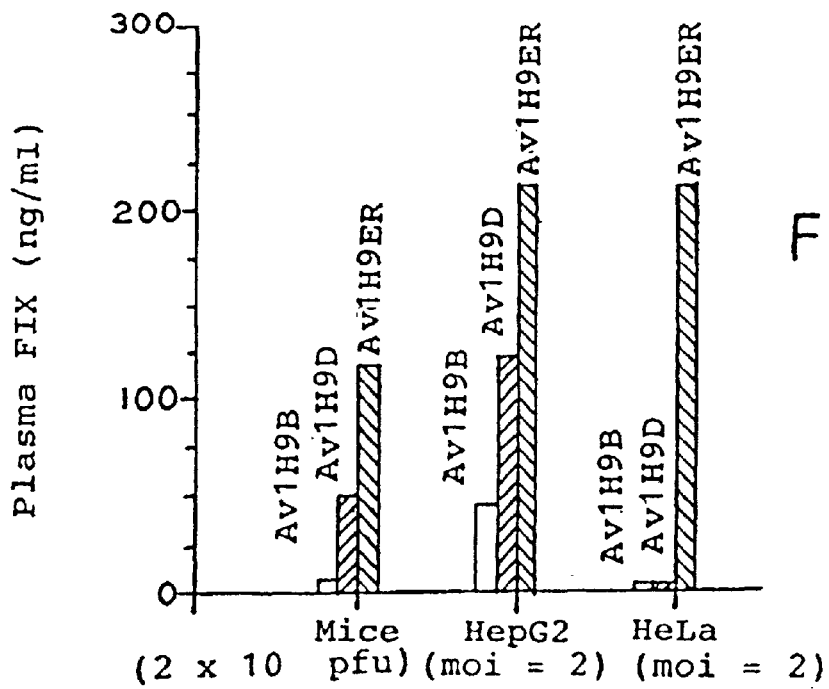
FIG. 43 is a graph of in vitro expression of Factor IX in HepG2 and HeLa cells, and of in vivo expression of Factor IX in mice treated with $2 \times 10^8$ pfu of Av1H9B, Av1H9D, or Av1H9ER. In each group of 3 bars, the leftmost bar represents data for Av1H9B, the middle bar, Av1H9D, and the rightmost bar, Av1H9ER.

Expression from Av1H9B, Av1H9D, and Av1H9ER was tested in tissue culture. HepG2 and HeLa cells were transduced at an moi of 2 (2 pfu per cell). 48 hours later the medium was collected and assayed by ELISA for human Factor IX. The data, shown in FIG. 43, demonstrate that the incremental improvements seen in HepG2 cells with Av1H9D and Av1H9ER correspond to those seen in vivo in mice that received $2\times10^8$ pfu of virus. In HeLa cells, the inclusion of the 3' untranslated region (Av1H9D) had no effect, whereas inclusion of the intron (Av1H9ER) improved expression dramatically.

EXAMPLE 13

High Level Tissue-Specific Expression of Functional Human Factor VIII in Mice

Cell Culture, Viral Transduction, and Metabolic Labeling 293 cells were cultured in IMEM (Improved Minimal Essential Medium) plus 10% FBS. HepG2 cells were cultured in EMEM (Eagle Minimal Essential Medium), 10% FBS, 1 mM nonessential amino acids, and 10 mM Na Pyruvate. For viral transduction, $1\times10^7$ HepG2 cells, plated on 100 mm dishes, were transduced at a multiplicity of infection (MOI) of 30. Medium was removed from the cells, and 0.4 ml of Infection Medium (IMEM plus 1% FBS) plus the indicated vector, or without vector for mock infections, was added. The plates were incubated with rocking for 1.5 hours, after which 10 ml of HepG2 culture media were added. 12 hours later, medium was changed, and 24 hours later, medium was assayed for Factor VIII (FVIII) activity, and cells were collected for RNA analysis. Metabolic labeling of the HepG2 cells was performed 12 hours after transduction, using $^{35}$S-methionine as described (Pittman et al., *Methods in Enzymology,* Vol. 222, pg. 236 (1993)). The conditioned medium was then collected, and the labeled BDD FVIII was purified by immunoprecipitation (Pittman and Kaufman, 1993). Where indicated, the immunoprecipitates were treated with 7.5 U/ml of thrombin (Haematologic Technologies, Essex Jct., Vt.) for one hour at 37° C. (Pittman et al., 1993).

Animal Procedures

All experiments involving mice adhered to protocols approved by the Institutional Animal Care and Use Committee in accordance with the Animal Welfare Act. C57BL/6 female mice, 3–6 weeks old, were purchased from Harlan Sprague Dawley. Tail vein injections were performed with the indicated doses of vector in 0.5 ml of Infection Medium. At the time points indicated, blood was obtained from the retroorbital plexus. Sodium citrate was immediately added to a final concentration of 0.38% (w/v) and the samples were placed on ice for no longer than 30 minutes. The samples were centrifuged for five minutes in an Eppendorf Microfuge after which the plasma was collected, aliquoted, and frozen.

Assays for Human FVIII

Total human FVIII antigen was quantitated by ELISA as described (Connelly et al., *Human Gene Therapy,* Vol. 6, pgs. 185–193 (1995)). Full-length recombinant FVIII protein generously supplied by Genetics Institute (Cambridge, Mass.) was used to generate a standard curve ranging from 1 to 100 ng/ml. BDD FVIII protein (supplied by Genetics Institute, Cambridge, Mass.) and full-length recombinant FVIII were similarly quantified by this ELISA. Normal mouse plasma did not interfere with the assay and the limit of sensitivity with mouse plasma samples containing BDD FVIII was 3 to 6 ng/ml. Mouse plasma samples were normally diluted 1:5 or 1:10 for the ELISA.

Biologically active human FVIII was measured using the Coatest chromogenic bio-assay (Chromogenix, Mölndal, Sweden) as directed. Coatest measures the FVIII-dependent generation of Factor Xa from Factor X, with one unit defined as the amount of FVIII activity in one ml of pooled human plasma, 100 to 200 ng/ml (Vehar et al., *Biotechnology of Plasma Proteins,* Albertini et al., eds. pg. 2155, Basel, Karger, 1991). Pooled human plasma (George King Bio-Medical, Inc., Overland Park, Kans.) was used as the FVIII activity standard.

Southern Blot and RNAse Protection Analyses

DNA was isolated from mouse livers using standard procedures. Briefly, livers were minced and incubated overnight in SDS/Proteinase K buffer. This was followed by three phenol/chloroform extractions, one chloroform extraction, ethanol precipitation and resuspension in water. 10 µg of each DNA sample were digested with Bam HI and subjected to Southern analysis. The probe, prepared by random oligonucleotide priming, contained human FVIII cDNA sequences from +73 to +1345 (Toole et al., 1984; Wood et al., 1984). The copy number control standards were prepared by adding 3.0 ng, 1.5 ng, 600 pg, and 60 pg of viral DNA, equivalent to 50, 25, 10, and 1 vector copies per cell, respectively to 10 µg of uninjected control mouse liver genomic DNA and digesting with Bam HI. The band intensities were quantitated with a Molecular Dynamics PhosphorImager SF.

RNA was isolated from mouse livers using the RNAzole B (Tel-Test, Friendswood, Tex.) extraction method. RNAse protection analyses were performed using the RNAse Protection Kit II (Ambion, Austin, Tex.). For each sample, quantities of 5 to 150 µg of total cellular RNA was hybridized for 12 hrs at 45° C. with $5\times10^4$ cpm of a gel-purified RNA probe (see below), digested with the RNAse A/T1 solution provided with the kit, diluted 1:100, processed as directed, and analyzed on an 8% polyacrylamide-8M urea gel (SequaGel, National Diagnostics, Atlanta, Ga.). The band intensities were quantitated with a Molecular Dynamics PhosphorImager SF. The values obtained were normalized for the number of G-residues in the protected mRNA fragment, as the antisense RNA probes were synthesized with $\alpha$-$^{32}$P-CTP. RNA molecular weight markers were synthesized using the RNA Century Marker Template Set (Ambion, Austin, Tex.). $^{32}$P-labeled fragments from Hpa II digested pBR322 were used as DNA size markers. The FVIII probe template (FIGS. 46 and 48), pGemSRpr, was constructed by inserting the 204 bp Sac I-Eco RI fragment isolated from pMT2LA (provided by Genetics Institute, Cambridge, Mass.) (Toole et al., *Prot. Nat. Acad. Sci.,* Vol. 83, pg. 5939 (1986) into pGem4Z (Promega, Madison, Wis.) cut with Sac I and Eco RI. The ALAPH81 probe template (FIG. 47), pGEMALAPF8pr, was created by digesting pAVALAPH81 (FIG. 20) with Mse I (filled in with T4 DNA polymerase) and Eco RI. This 506 bp fragment containing part of the albumin promoter, the ApoA1 first exon, first intron, second exon, and FVIII coding region sequences was inserted into pGem4Z (Promega, Madison, Wis.) digested with Sma I and Eco RI. The ALH81 probe template (FIG. 47), pGemF8probe, has been described (Connelly et al., 1995). The mouse GAPDH-specific and mouse actin-specific probe templates were generated from the pTRI-GAPDH mouse plasmid (Ambion, Austin, Tex.) and pTRI-ACTIN mouse plasmid (Ambion, Austin, Tex.) digested with Sty I and Hind III, respectively. The FVIII-specific probe templates were linearized with Hind III and all anti-sense RNA probes were synthesized with SP6 polymerase and U-$^{32}$P-CTP (Amersham, Arlington Heights, Ill., 3000 Ci/mmole).

Characterization of Human FVIII Expressed in vitro

The expression of human BDD FVIII in HepG2, human hepatoma cells, transduced with either Av1ALH81 (FIG. 21) or Av1ALAPH81 (FIG. 23) was compared (Table V). The biological activity of the BDD FVIII present in the conditioned medium was analyzed using the Coatest chromogenic bioassay (Chromogenix, Mölndal, Sweden).

TABLE V

| Vector | Biological Activity (mU/10$^6$ cells/24 hrs) |
| --- | --- |
| Av1ALAPH81 | 2375 |
|  | 2167 |
| Av1ALH81 | 1716 |
|  | 1694 |
| Av1ALH9B | 0 |
| Mock | 0 |

As shown in Table V, in duplicate infections with Av1ALH81 and Av1ALAPH81, >1600 or >2100 mU per 10$^6$ cells per 24 hours, respectively, were detected, revealing that transduction with both vectors resulted in the production of high levels of biologically active FVIII. No FVIII was detected in mock infected cells or cells transduced with a control vector, Av1ALH9B (Connelly et al., 1995), a recombinant adenovirus encoding the human factor IX (FIX) cDNA (Table V).

Figure 44:
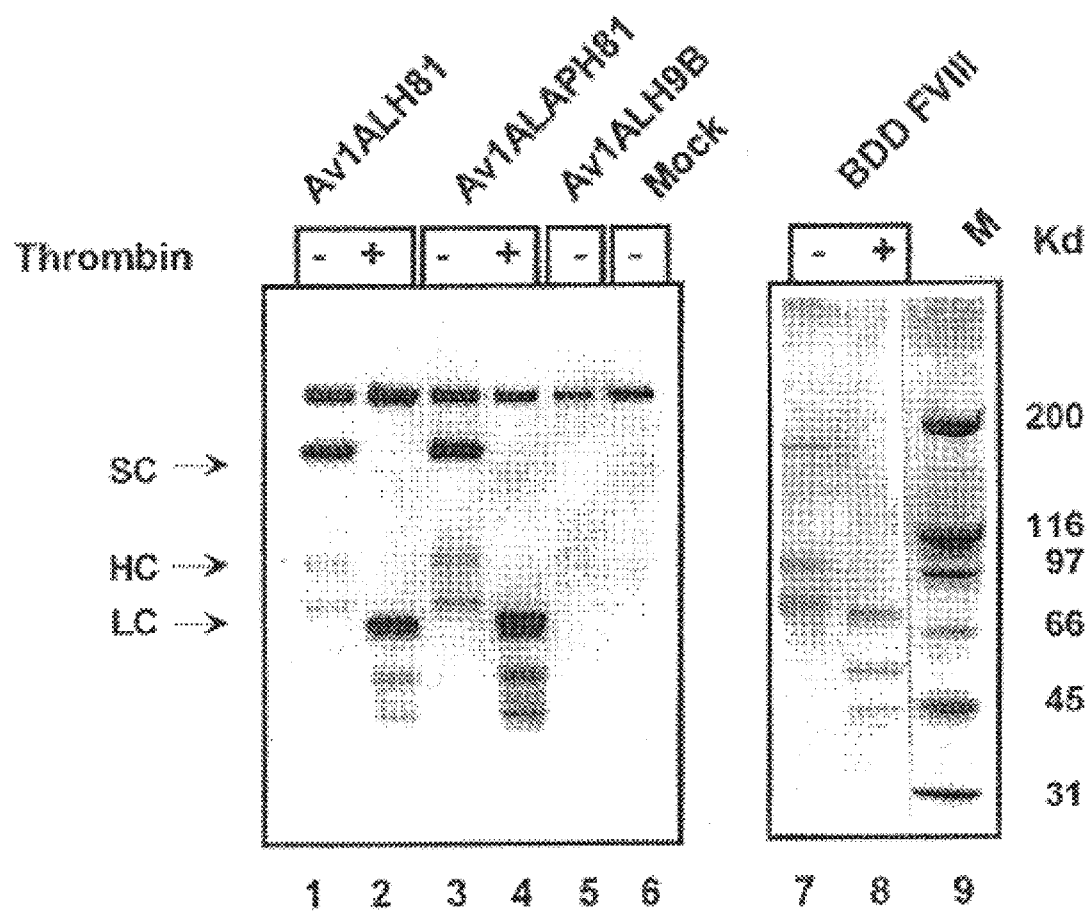
FIG. 44 is an immunoprecipitation purification of B-domain deleted Factor VIII produced in HepG2 cells transduced with Av1ALAPH81, Av1ALH81, or Av1ALH9B, or mock infected cells.

The structure of the FVIII protein produced by HepG2 cells was studied by metabolic labeling of the cells after transduction with each FVIII-encoding vector, and subsequent immunoaffinity purification of the labeled BDD FVIII protein from the conditioned medium (FIG. 44). The cells were exposed to $^{35}$S-methionine and the labeled BDD FVIII was purified by immunoprecipitation (Pittman, et al., 1993). The immunoprecipitates before (−) or after (+) treatment with thrombin (Pittman and Kaufman, 1993) were analyzed by reducing SDS polyacrylamide gel electrophoresis (lanes 1–6). For comparison, purified BDD FVIII protein (5.5 μg/lane; a gift from Genetics Institute, Cambridge, Mass.), before (−) or after (+) treatment with thrombin was analyzed on the same gel as the immunoprecipitates. After electrophoresis, the gel was Coomassie stained and divided. The portion containing the purified protein and protein size markers was dried and photographed (lanes 7 and 8), while the portion containing the metabolically labeled immunoprecipitates was analyzed by autoradiography (lanes 1–6). The arrows labeled SC, HC, and LC indicate the BDD FVIII single-chain, heavy-chain, and light-chain polypeptides (Pittman et al., 1993). Protein molecular weight standard (lane 9; Bio-Rad, Hercules, Calif.) sizes are indicated in kilodaltons (Kd).

The BDD FVIII protein secreted by both Av1ALH81- and Av1ALAPH81-transduced cells was composed of three prominent species, representing the 170 Kd single chain, the 92 Kd heavy chain, and the 80 Kd light chain (FIG. 44, lanes 1 and 3) and was directly comparable to the polypeptide pattern observed with the purified BDD FVIII protein isolated from stably transfected CHO cells (FIG. 44, lane 7; Pittman et al., 1993). Digestion with thrombin resulted in the disappearance of the single chain, and the generation of 73, 50, and 43 Kd polypeptides (FIG. 44, lanes 2 and 4), which was identical to the thrombin cleavage pattern of the purified BDD FVIII protein (FIG. 44, lane 8; Pittman et al., 1993). No FVIII-specific peptides were detected in Av1ALH9B-transduced or mock infected cells (FIG. 44, lanes 5 and 6). The >200 Kd polypeptide (FIG. 44, lanes 1–6) probably represents non-specific copurification of fibronectin (Connelly et al., 1995) and was not detected in the purified protein samples (FIG. 44, lanes 7 and 8). RNAse protection analysis verified that transcription initiation of the BDD FVIII mRNA produced in Av1ALH81-transduced HepG2 cells occurred at the predicted site and that the Av1ALAPH81-derived mRNA was accurately spliced (data not shown). Therefore, in vitro transduction of cells with both FVIII-encoding vectors resulted in the production of high levels of authentic, biologically active human BDD FVIII.

In Vivo Expression of Human FVIII

Figure 45:
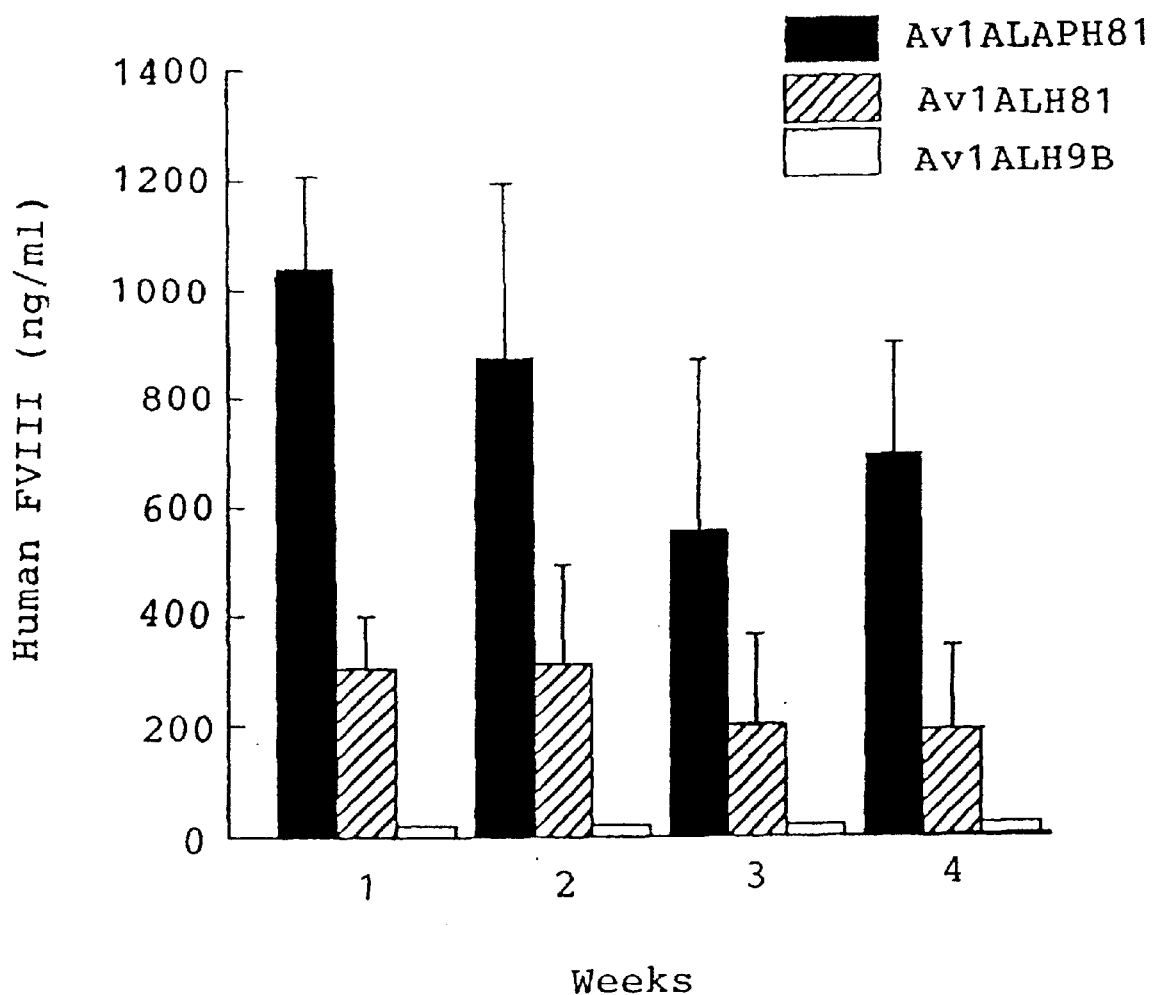
FIG. 45 is a graph of the expression of human Factor VIII in the plasma of mice which received $4 \times 10^9$ pfu of Av1ALAPH81, Av1ALH81, or Av1ALH9B.

To compare the expression of human BDD FVIII in mice injected with the FVIII-encoding adenoviral vectors, a short-term study was designed in which 4×10$^9$ pfu of Av1ALH81 or Av1ALAPH81 was administered intravenously, via tail vein, to groups of eight mice each. Since the Coatest assay does not distinguish human FVIII activity from mouse FVIII, an ELISA specific for full-length and BDD FVIII was developed (Connelly et al., 1995) and used to measure human FVIII in mouse plasma. The results of such assay are shown in FIG. 45. Data are plotted as a mean value and standard deviation at each time point. Four mice for each group were sacrificed one week after vector injection for subsequent DNA/RNA analysis. One week post injection, human FVIII levels in the plasma of mice injected with Av1ALH81 averaged 307±93 ng/ml (FIG. 45). However, plasma FVIII levels in mice that had received Av1ALAPH81 averaged 1046±163 ng/ml (FIG. 45). Normal FVIII levels in humans are 100 to 200 ng/ml (Vehar et al., 1991), and therapeutic levels are as low as 10 ng/ml (Vehar et al., 1991). Therefore, mice that received Av1ALAPH81 were producing human FVIII at levels one hundred fold higher than human therapeutic levels, and three times higher than mice injected with an identical dose of Av1ALH81. No human FVIII was detected in uninjected control mice (data not shown) or three mice injected with 4×10$^9$ pfu of Av1ALH9B (FIG. 45). FVIII levels in the mouse plasma were analyzed weekly for four weeks at which time the experiment was terminated. At three to four weeks post injection, FVIII levels in both sets of mice had decreased 30% from the peak expression level detected at one week (FIG. 45).

Figure 46A:
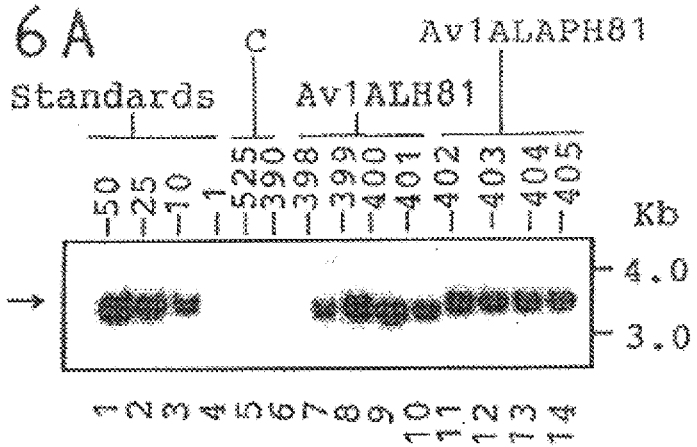
FIG. 46A is a Southern blot analysis of DNA from the livers of mice which received Av1ALH81 or Av1ALAPH81.

To verify that the liver transduction efficiency of the two FVIII vectors was the same, two groups of four mice each injected with either vector were sacrificed one week post injection and liver DNA was assayed for the presence of the vector by Southern analysis (FIG. 46A). Each DNA sample was digested with BamHI prior to Southern analysis. The arrow designates a 3.2 kb fragment containing Av1ALH81-derived Factor VIII sequences. Av1ALAPH81-derived sequences generated a 3.4 kb fragment. Lanes 5 and 6 represent liver DNA from an uninected control mouse, and a mouse that received the control vector, Av1ALH9B, respectively. Lanes 1–4 contain digested Av1ALH81 viral DNA in amounts equivalent to 50, 25, 10, and 1 vector copies per cell. DNA markers (Gibco-BRL, Gaithersburg, Md.) sizes are indicated in kilobases (kb).

Comparison to vector copy number standards (FIG. 46A, lanes 1–4) showed an average of 18 vector copies per cell for both Av1ALH81- (FIG. 46A, lanes 7–10) and Av1ALAPH81- (FIG. 46A, lanes 11–14) transduced liver DNA samples, revealing that both vectors transduced the mouse livers to a similar level. No FVIII-containing vector was detected in an uninjected control mouse liver DNA sample (FIG. 46A, lane 5), or a liver DNA sample isolated from a mouse injected with Av1ALH9B (FIG. 46A, lane 6).

The relative levels of human FVIII mRNA produced in the mice was determined by RNAse protection analysis using RNA isolated from the mouse livers (FIG. 46B), and an anti-sense RNA probe encoding an internal portion of the FVIII coding region shared between both vectors (FIG. 46C). 30 µg of total cellular RNA isolated from the mouse livers were used in each reaction. The arrow labeled FVIII designates the 212 nt human FVIII-specific protected probe fragment. Lanes 1 and 12 contain $^{32}$P-labeled DNA and RNA molecular weight markers. Lane 2 contains undigested full-length probe. Lane 3 contains liver RNA from an Av1ALH9B-injected control mouse. Exposure shown is 5 days with intensifying screens. The lower panel displays a separate RNAse protection assay, using 30 µg of total cellular mouse liver RNA, and an anti-sense RNA probe encoding a portion of the mouse glyceraldehyde 3-phosphodehydrogenase (GAPDH) cDNA. The arrow labeled GAPDH designates the 134 nt mouse GAPDH-specific protected probe fragment. Exposure shown is 6 hours with intensifying screen.

Figure 46B:
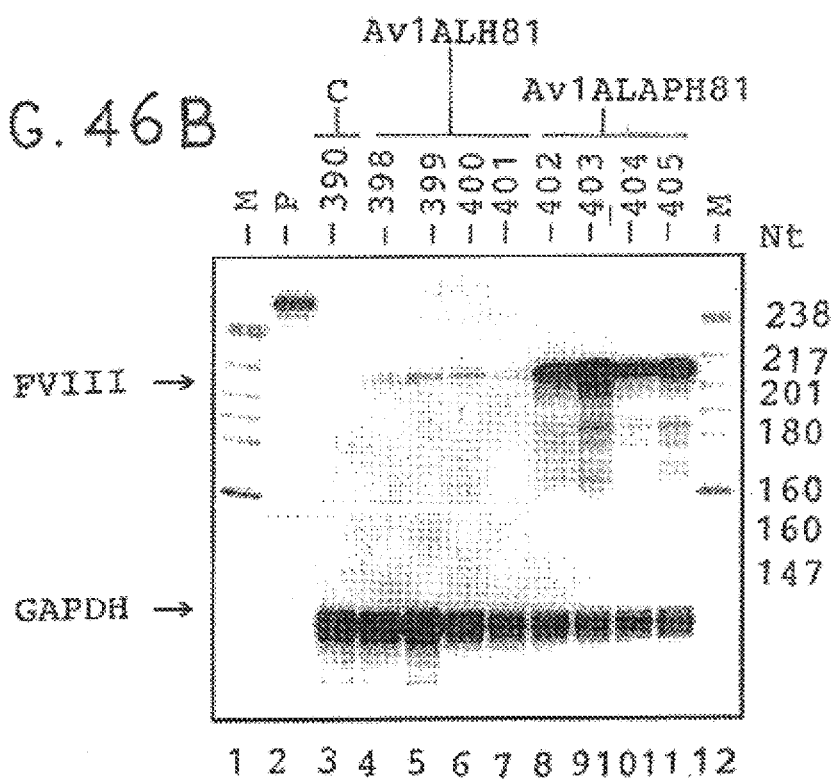
FIG. 46B is an autoradiograph of an RNase protection analysis of RNA from the livers of mice which received Av1ALAPH81 or Av1ALH81.
Figure 46C:
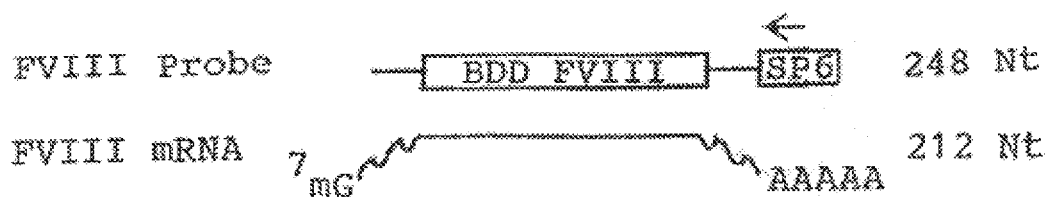
FIG. 46C is a schematic of a Factor VIII probe template and the complementary Factor VIII mRNA fragment.

With this probe, human FVIII-specific mRNA should protect a 212 nt fragment. A fragment of this size was seen in each of the FVIII-encoding vector-transduced mouse liver RNA samples (FIG. 46B, lanes 4–11), and not in the Av1ALH9B-injected control mouse liver sample (FIG. 46B, lane 3). Quantitation of the FVIII-specific mRNA protected probe fragments by phosphoimager scanning showed an average of 15-fold more RNA in the Av1ALAPH81-derived samples (FIG. 46B, lanes 8–11), compared to the Av1ALH81-transduced RNA samples (FIG. 46B, lanes 4–7). As an internal RNA standard, the mouse liver RNA samples were analyzed in a separate RNAse protection assay using an anti-sense RNA probe containing a portion of the mouse glyceraldehyde 3-phosphate dehydrogenase (GAPDH) coding region to verify the integrity of the RNA in each sample (FIG. 46B, lower panel). Therefore, the addition of an ApoA1 intron to the BDD FVIII cDNA resulted in 3-fold higher plasma FVIII levels, and a 15 fold increase in FVIII-specific mRNA in the livers of mice injected with Av1ALAPH81, compared to the FVIII protein and mRNA levels detected in mice that received an identical dose of Av1ALH81.

To verify that transcription from the albumin promoter initiated at the predicted site in vivo (Gorski et al., Cell, Vol. 47, pg. 767, 1986; Connelly et al., 1995), an RNAse protection analysis was performed using an anti-sense RNA probe containing sequences from the albumin promoter and the 5' end of the BDD FVIII cDNA (FIG. 47B; Connelly et al., 1995).

Figure 47A:
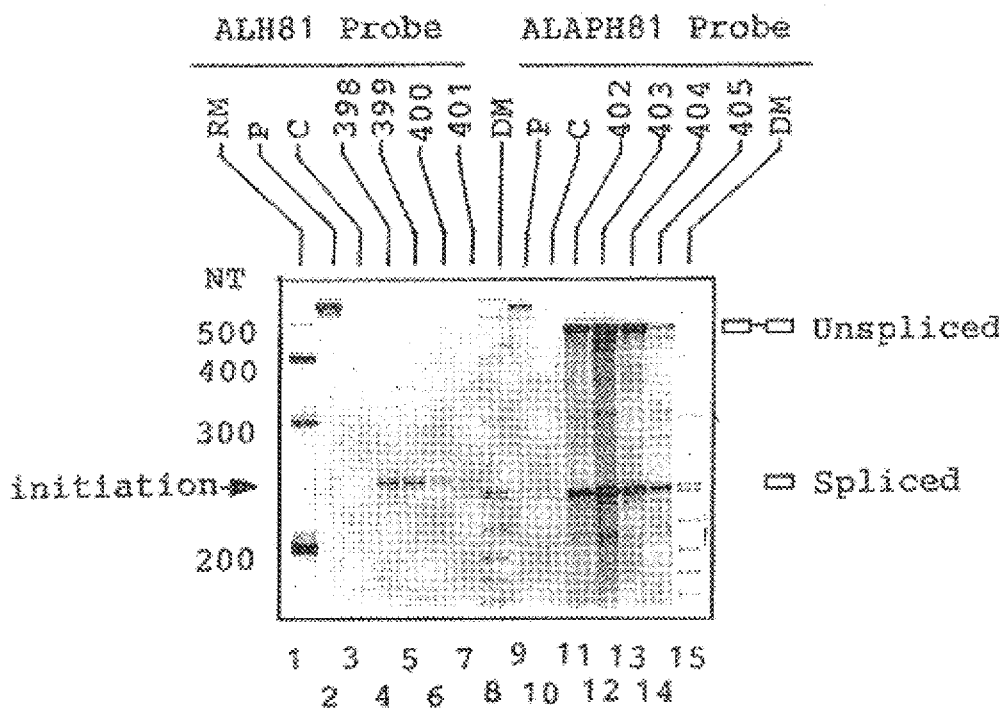
FIG. 47A is an autoradiograph of RNase protection analysis of RNA from the livers of mice which received Av1ALH81 or Av1ALAPH81, to determine transcription initiation and splicing efficiency of vector-derived RNA.
Figure 47B:
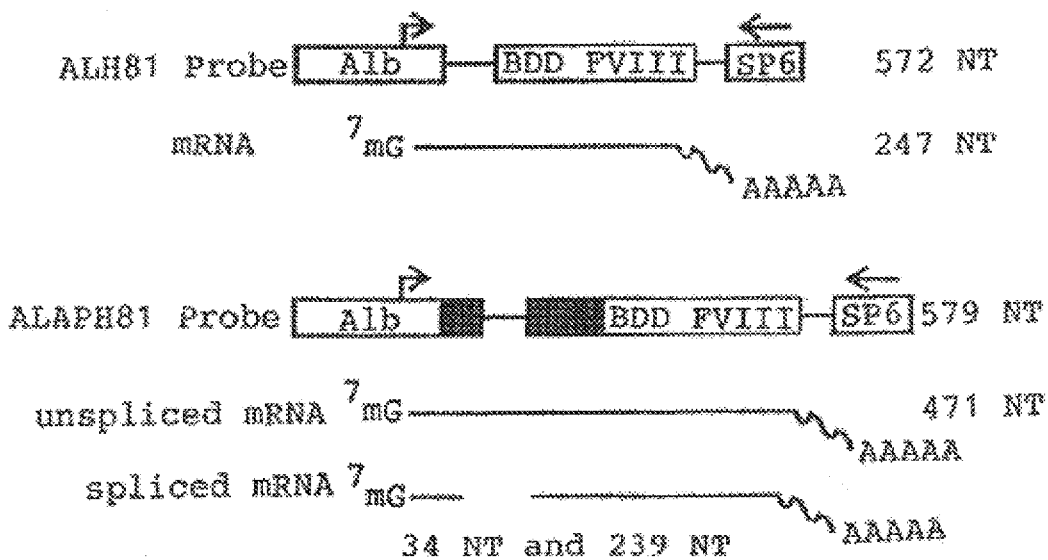
FIG. 47B is a schematic depicting the probes employed in FIG. 47A.

FIG. 47A depicts the RNase protection analysis results. RNA samples isolated from mice that received Av1ALH81 (Lanes 4–7) were analyzed using the ALH81 probe. The arrow labeled initiation designates the 247 nt protected probe fragment indicating transcripts properly initiated at the albumin promoter. RNA isolated from Av1ALAPH81-injected mice (Lanes 11–14) was analyzed using the ALAPH81 probe. The 471 nt and 239 nt protected probe fragments, representing unspliced and spliced transcripts, respectively, are indicated. Liver RNA purified from a mouse injected with the control vector, Av1ALH9B, analyzed with ALH81 (Lane 3) and ALAPH81 (Lane 10) probes served as the negative control. Lane 1 contains $^{32}$P-labeled RNA molecular weight markers. Lanes 8 and 15 contain $^{32}$P-labeled DNA molecular weight markers. Lanes 3 and 9 contain undigested, full-length ALH81 and ALAPH81 probes, respectively. FIG. 47B is a schematic diagram depicting the probe templates and complementary mRNA fragments. The boxes marked Alb and SP6 represent the albumin and SP6 promoter regions, respectively. The rightward pointing arrow indicates the site of transcription initiation from the albumin promoter. The leftward pointing arrow indicates the direction of transcription from the SP6 promoter. The solid black boxes represent the Apo A1 genomic sequences.

Analysis of liver RNA samples isolated from mice injected with Av1ALH81 revealed a fragment of the predicted size for transcripts properly initiated at the albumin promoter (247 nts; FIG. 47B, lanes 4–7; Connelly et al., 1995), and was not found in RNA isolated from Av1ALH9B-transduced mouse liver (FIG. 47A, lane 3). The accuracy and efficiency of splicing of Av1ALAPH81-derived transcripts were evaluated using an anti-sense RNA probe capable of distinguishing unspliced FVIII mRNA from spliced mRNA (FIG. 47B) in an RNAse protection analysis (FIG. 47A). With this probe, unspliced RNA would protect a fragment of 471 nts. Transcripts accurately spliced would produce two protected fragments, one 34 nts, representing the ApoA1 5' exon, and a fragment of 239 nts derived from the 3' exon and FVIII coding region. All Av1ALAPH81-derived RNA samples contained protected fragments representing unspliced and spliced transcripts in approximately equal amounts (FIG. 47A, lanes 11–14). Quantitation by phosphorimager scanning, and adjustment of the values for the number of G residues in each protected fragment showed that an average of 69% of the transcripts were spliced. Therefore, transcription from the albumin promoter initiated at the predicted site in vivo, and accurate splicing of the Apo A1 intron sequences from the FVIII pre-mRNA occurred in the mouse livers.

Liver-specific Expression of the Albumin Promoter

The modified mouse albumin promoter (Hafenrichter et al., Blood, Vol. 10, pg. 3394 (1994); Connelly et al., 1995) had been shown to direct a high level of liver-specific expression in a conditionally transformed hepatocyte cell line, H2.35 (Zaret et al., 1998), under differentiating conditions (DiPersio et al., 1991), and was active when transferred to rat hepatocytes in vivo, in the context of a retroviral vector (Hafenrichter et al., 1994). However, the function of the mouse albumin promoter in vivo, when incorporated into an adenoviral vector backbone had not been determined. To ascertain whether expression from the albumin promoter was tissue-specific, an RNAse protection analysis was performed using RNA isolated from several Av1ALAPH81-transduced mouse organs. It had been shown previously, however, that intravenous injection of adenoviral vectors to mice resulted in preferential accumulation of vector in the liver with other organs having lower transduction efficiencies (Smith et al., Nature Genetics, Vol. 5, pg. 397 (1993)). Therefore, first it was necessary to determine the relative transduction efficiencies of the different organs, and then normalize the RNA concentrations for the RNAse protection assay dependent upon the organ transduction efficiency. DNA was isolated from liver, lung, and spleen derived from the Av1ALAPH81-injected mice one week post injection, and the vector copy number per cell was assessed by Southern analysis (FIG. 48A).

Each DNA sample was digested with Bam HI and subjected to Southern analysis. Li, Lu, and Sp indicate liver, lung, and spleen DNA samples, respectively. The arrow designates a 3.4 kb fragment derived from Av1ALAPH81 sequences. Lanes 4 and 5 represent liver DNA from an uninjected control mouse, and a mouse that received the control vector, Av1ALH9B, respectively. Lanes 1–3 contain digested Av1ALH81 viral DNA in amounts equivalent to 25, 10, and 1 vector copies per cell. DNA markers (Gibco-BRL, Gaithersburg, Md.) sizes are indicated in Kb. The relative transduction efficiencies of the organs was determined by Phosphor Imager quantitation.

Figure 48A:
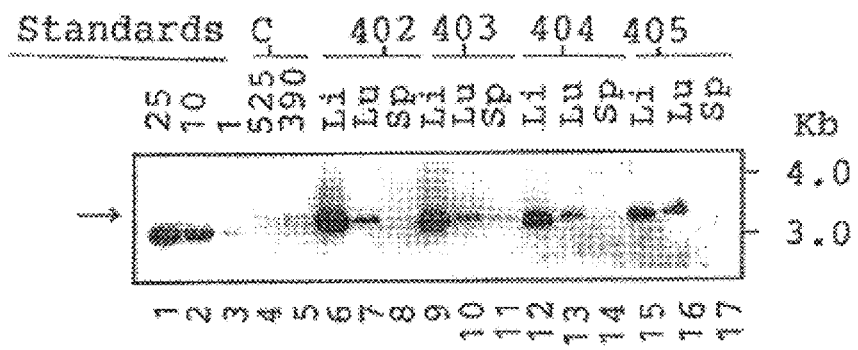
FIG. 48A is a Southern blot analysis of DNA isolated from the livers, lungs, and spleens of mice that received Av1ALAPH81.

As had been observed previously, liver was the most efficiently transduced organ, with lung and spleen having approximately 10% and 1% of the vector copy number of liver, respectively (FIG. 48A; Smith et al., 1993).

Figure 48B:
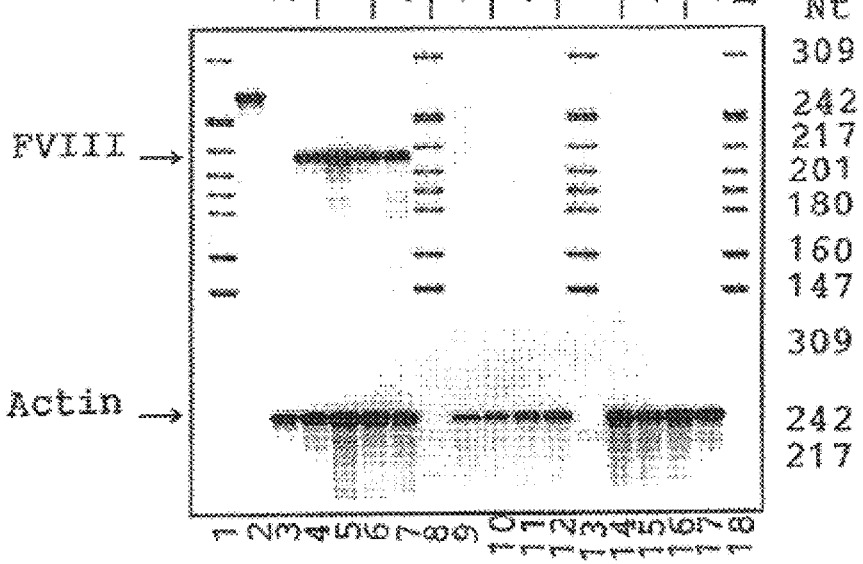
FIG. 48B is an autoradiograph of RNase protection analysis of RNA isolated from the livers, lungs, and spleens of mice that received Av1ALAPH81.

For the RNAse protection analysis, the RNA quantities were adjusted relative to the organ transduction efficiency. (FIG. 48B.)

5 µg of total liver RNA was used in each reaction. Lung and spleen RNA quantities were adjusted relative to the organ transduction efficiency. The lung RNA concentrations used for each reaction were: Lanes 9–12; 50 µg, 35 µg, 35 µg, and 12 µg. The spleen RNA concentrations were: Lanes 14–17; 150 µg, 100 µg, 70 µg, and 100 µg. The arrow labeled FVIII designates the 212 nt human FVIII-specific protected probe fragment. Lanes 1, 8, 13, and 18, contain $^{32}$P-labeled DNA molecular weight markers. Lane 2 contains undigested full-length probe. Lane 3 contains liver RNA from an Av1ALH9B-injected control mouse. Exposure shown is 20 days with intensifying screens. The lower panel displays a separate RNAse protection assay using 10 µg of each RNA, and an anti-sense probe encoding a portion of the mouse β-actin cDNA. The arrow labeled Actin designates the 210 nt mouse actin-specific protected probe fragment. Exposure shown is 6 hr with intensifying screen.

Figure 48C:
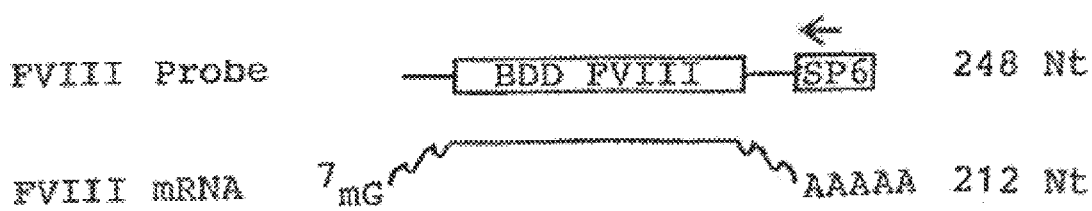
FIG. 48C is a schematic of the probe template and complementary Factor VIII mRNA fragment employed in FIG. 48B.

Using an anti-sense RNA probe complimentary to the FVIII coding region, a FVIII-specific protected fragment of the predicted size (212 nts; FIG. 48C) was detected only in the liver RNA samples (FIG. 48B, lanes 4–7). No FVIII-specific RNA was found in the lung or spleen RNA samples (FIG. 48B, lanes 9–12, and lanes 14–17), or in the Av1ALH9B-transduced control liver RNA (FIG. 48B, lane 3). Analysis of equal quantities of RNA (10 µg) from all samples with an anti-sense RNA probe specific to the mouse actin coding region verified the integrity of the RNA within each of the samples (FIG. 48B, lower panel). Notably, the differences in the actin RNA levels observed in the liver, lung, and spleen samples probably reflects the normal variation in the endogenous expression levels of actin within the three organs. Therefore, the albumin promoter incorporated into an adenoviral vector directed the expression of BDD FVIII in a liver-specific manner.

Biological Activity of FVIII Produced in vivo

Because the FVIII-encoding adenoviral vector, Av1ALAPH81, mediated the expression of human FVIII in mice at 10-fold human physiological levels (FIG. 45), it was important to verify that the FVIII produced in the mice was biologically active. Pooled plasma from groups of ten mice each that received Av1ALAPH81, Av1ALH9B, or no vector injection, was analyzed by ELISA to measure human FVIII antigen and Coatest to determine FVIII biological activity (both mouse and human; Table VI). In this experiment, groups of ten mice each received $4\times10^9$ pfu of Av1ALAPH81 (FVIII), Av1ALH9B (FIX), or no injection (Neg). Plasma was collected and pooled prior to injection (time 0) or at the indicated times post injection, and analyzed by ELISA for human FVIII antigen and by Coatest for FVIII (mouse and human) biological activity. The corrected Coatest activity units were calculated by subtracting the FVIII activity measured in the FIX-transduced group from the activity detected in the pooled FVIII plasma samples. The corrected activity units were converted to ng using the definition of one Coatest unit equal to the amount of FVIII in one ml of human pooled plasma, 100 to 200 ng/ml (Vehar et al., 1991).

TABLE VI

| Pooled Plasma | Time | ELISA Human FVIII (ng/ml) | Coatest FVIII Biological Activity | | |
|---|---|---|---|---|---|
| | | | Actual (mU) | Corrected (mU) | Calculated (ng) |
| FVIII | 0 | 0 | 2155 | — | — |
| FIX | | 0 | 2108 | — | — |
| Neg | | 0 | 2014 | — | — |
| FVIII | 1 | 1470 | 16214 | 10494 | 1049–2098 |
| FIX | week | 0 | 5720 | — | — |
| Neg | | 0 | 2484 | — | — |
| FVIII | 2 | 1149 | 15033 | 7864 | 786–1572 |
| FIX | weeks | 0 | 7169 | — | — |
| Neg | | 0 | 2431 | — | — |

The endogenous mouse FVIII activity, determined for all groups prior to vector administration, was found to be approximately 2000 mU/ml (Table VI). Notably, the mice that received the control vector, Av1ALH9B, showed a two to three-fold increase in endogenous mouse FVIII levels, as no human FVIII was detected in the pooled plasma as determined by ELISA (Table VI). Therefore, to determine the amount of human FVIII in the mice that received Av1ALAPH81 above the endogenous mouse FVIII levels, the FVIII activities measured in the control vector-transduced group were subtracted from the activity detected in the pooled Av1ALAPH81 plasma samples, to give the corrected mU/ml levels. At both one and two weeks post injection, the amount of human FVIII calculated from the corrected activity values matched the human FVIII antigen levels as determined by ELISA. Therefore, these data indicate that the high level of human FVIII produced in the mice was biologically active.

High Level FVIII Expression in vivo with Administration of a Low Vector Dose

Figure 49:
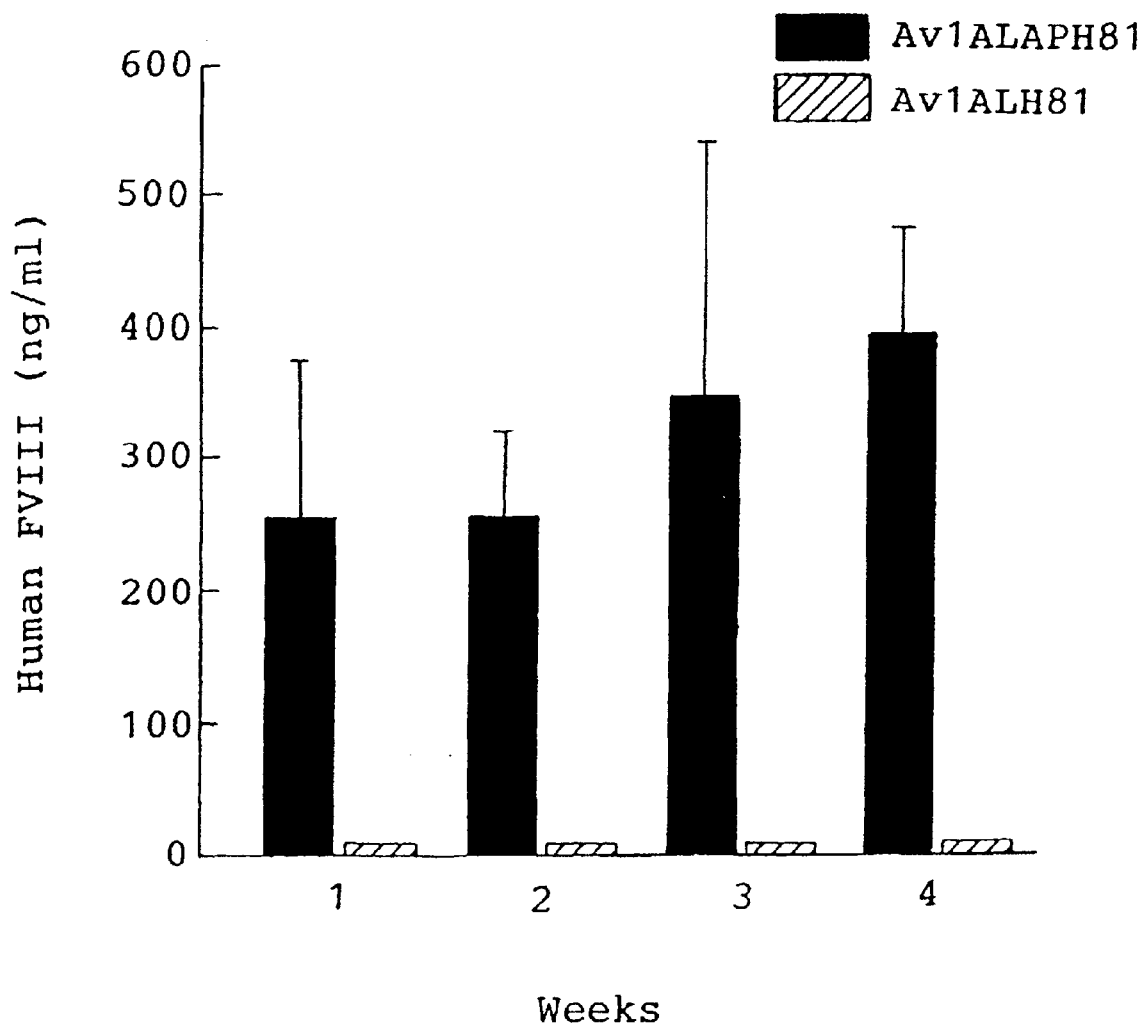
FIG. 49 is a graph of human Factor VIII expression in mice after administration of $5 \times 10^8$ pfu of Av1ALAPH81 OR Av1ALH81.

Because administration of a high dose, $4\times10^9$ pfu, of Av1ALAPH81 to mice resulted in expression of FVIII in the mouse plasma at ten-fold human physiological levels (FIG. 45), it was feasible that injection of significantly lower vector doses to mice may allow expression of therapeutic levels of FVIII. Therefore, groups of five mice each were injected intravenously with $5\times10^8$ pfu of Av1ALAPH81 or Av1ALH81, and plasma FVIII levels were determined by ELISA weekly for four weeks (FIG. 49). One week post injection, human FVIII levels in the plasma of mice that had received Av1ALAPH81 averaged 257±120 ng/ml. At four weeks, these levels had increased to 397±78 ng/ml. However, mice that had received an identical dose of Av1ALH81 did not produce detectable levels of FVIII (FIG. 49). In addition, no FVIII was detected in mice that received the control vector, Av1ALH9B, or in uninjected control mice (data not shown). Therefore, administration of an eight-fold lower dose of Av1ALAPH81 to mice allowed the expression of human FVIII in the mice at two to three-fold human physiological levels.

EXAMPLE 14

Figure 50B:
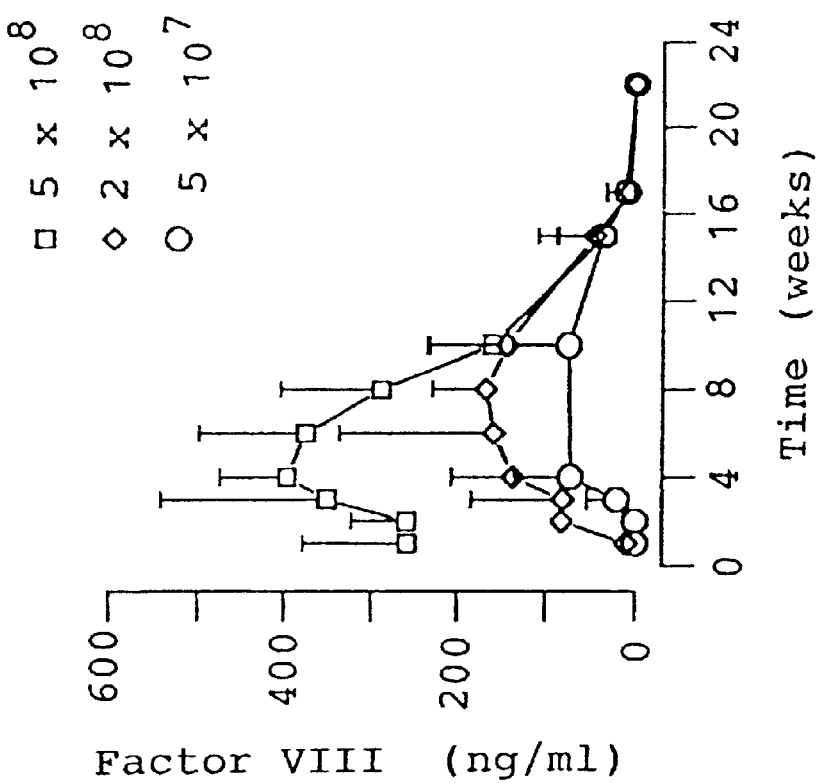
FIGS. 50A and 50B are graphs of dose response curves for the time course of human Factor VIII expression in mice that received $4 \times 10^9$ pfu; $1 \times 10^9$ pfu; $5 \times 10^8$ pfu; $2 \times 10^8$ pfu; or $5 \times 10^7$ pfu of Av1ALAPH81.
Figure 50A:
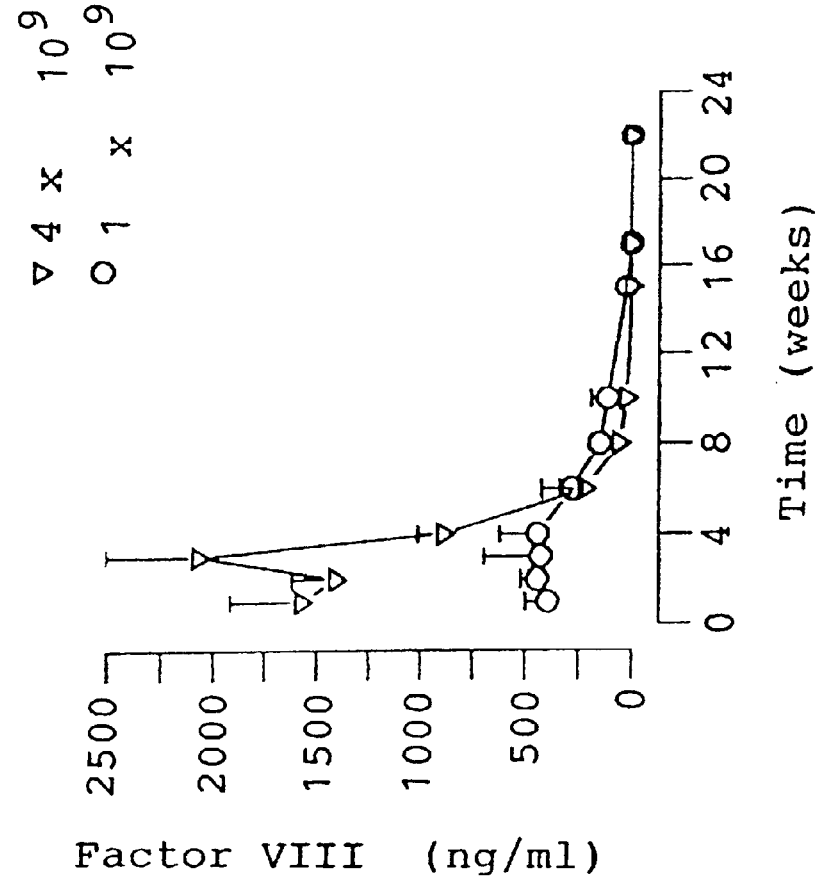

Sustained Expression of Physiological Levels of Functional Human Factor VIII in Mice It was shown that intravenous administration of a high dose, $4\times10^9$ pfu, of Av1ALAPH81 (FIG. 23) to mice mediated the expression of human FVIII in the mouse plasma in amounts 10-fold higher than human physiological levels (>1000 ng/ml one week post injection) (Connelly et al., 1995) To determine if high level human FVIII expression could be achieved with administration of lower vector doses, 5 groups of 5 mice each were injected, via tail vein, with decreasing doses of Av1ALAPH81, in amounts of $4 \times 10^9$; $5 \times 10^8$; $2 \times 10^8$; and $5 \times 10^7$ pfu/mouse. These amounts are equivalent approximately to $1.6 \times 10$" pfu/kg; $2.0 \times 10^{10}$ pfu/kg; $8.0 \times 10^9$ pfu/kg; and $2.0 \times 10^9$ pfu/kg, respectively. Plasma levels of human FVIII were measured by a human FVIII-specific ELISA (Connelly et al., 1995) at the indicated times ranging from one to 22 weeks post vector administration (FIG. 50). At weekly intervals, plasma samples were collected and human Factor VIII antigen was quantitated by ELISA. Data in FIGS. 50A and 50B are plotted as a mean value and standard deviation at each time point. Mice that received the highest dose of vector, $4 \times 10^9$ pfu, showed extremely high levels of FVIII expression, peaking three weeks post injection at 2063+/−446 ng/ml (FIG. 50A). With administration of $1 \times 10^9$ pfu of Av1ALAPH81 to mice, peak plasma human FVIII expression was 440+/−80 ng/ml at two weeks. However, in both groups, a sharp decline in FVIII expression was detected beginning at 4–6 weeks, with plasma FVIII levels dropping below the limit of sensitivity of the assay (60 ng/ml) by 8–10 weeks (FIG. 50A). Alternatively, a different pattern of FVIII expression was observed in mice that received the lower vector doses (FIG. 50B). At a dose of $5 \times 10^8$ pfu, FVIII expression peaked at 397+/31 78 ng/ml four weeks post injection. Peak expression levels at doses of $2 \times 10^8$ pfu and $5 \times 10^7$ pfu were 168+/31 61 ng/ml at 8 weeks, and 75+/31 63 ng/ml at 10 weeks after vector administration, respectively. However, by 17 to 22 weeks human FVIII was undetectable in the mouse plasma (FIG. 50B). No human FVIII was detected in four mice that received $4 \times 10^9$ pfu of Av1ALH9B, a recombinant adenovirus encoding the human factor IX (FIX) cDNA (Connelly et al., 1995a; 1995b), or in uninjected control mice (data not shown). It is noteworthy that at 15 weeks at least one mouse within each of the low dose groups were expressing human FVIII at human physiological levels (>100 ng/ml). Interestingly, mice that received either of the two lowest vector doses showed a delay in the onset of FVIII expression (FIG. 50B). Therefore, at lower vector doses, peak FVIII expression was delayed and FVIII expression showed a gradual decline over 15 to 22 weeks (FIG. 50B), compared to the sharp drop in FVIII expression between 4 to 6 weeks observed with the high vector doses (FIG. 50A). These results reveal that administration of low vector doses allowed the sustained expression of physiological levels of human FVIII in mice for at least 15 weeks.

Figure 51A:
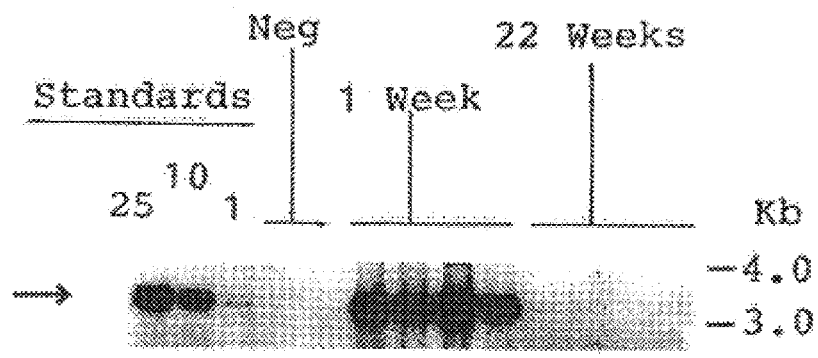
FIG. 51A is a Southern blot analysis of DNA isolated from the livers of mice which received $4 \times 10^9$ pfu of Av1ALAPH81.

The loss in detectable levels of FVIII in the mouse plasma 17 to 22 weeks after vector administration could be caused by several factors. For example, vector DNA may have been eliminated from the liver, the albumin promoter could have become inactivated, or the mice may have developed an antibody response directed against human FVIII. To distinguish between these possibilities, mouse liver DNA and RNA obtained from mice injected with $4 \times 10^9$ pfu or $5 \times 10^8$ pfu of Av1ALAPH81 one and 22 weeks after vector administration was analyzed (FIG. 51). Groups of mice that received a dose of $4 \times 10^9$ pfu or $5 \times 10^8$ pfu of Av1ALAPH81 were sacrificed at one week or at 22 weeks after vector administration. Liver DNA and RNA were isolated from each mouse liver. FIG. 51A shows Southern analysis of mouse liver DNA isolated from mice that received $4 \times 10^9$ pfu of Av1ALAPH81. Each DNA sample was digested with BamHI, and subjected to Southern analysis. The arrow designates a 3.4 kb fragment containing Av1ALAPH81-derived Factor VIII sequences. The standards were generated by digesting purified Av1ALAPH81 viral DNA in amounts equivalent to 25, 10, and 1 vector copies per cell. DNA marker sizes are indicated in kb. For mice that received the high vector dose, Southern analysis of liver DNA with comparison to vector copy number standards of 25, 10, and 1 copies (FIG. 51A, lanes 1–3) showed an average of 45 vector copies per cell, at one week post injection (FIG. 51A, lanes 6–9), compared to an average of 0.2 copies per cell at 22 weeks (FIG. 51A, lanes 10–13) revealing that the majority of vector DNA had been lost from the mouse livers. No FVIII-containing vector was detected in an uninjected control mouse liver DNA sample (FIG. 51A, lane 4), or a liver DNA sample isolated from a mouse injected with $4 \times 10^9$ pfu of Av1ALAPH81 (FIG. 51A, lane 5).

Figure 51B:
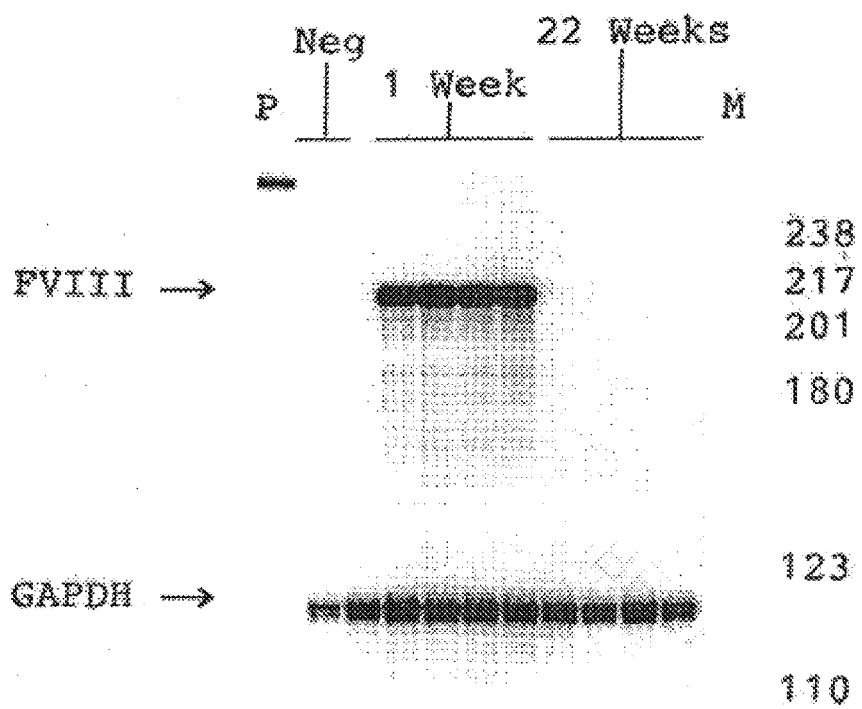
FIG. 51B is an autoradiograph of RNase protection analysis of RNA isolated from the livers of mice which received $4 \times 10^9$ pfu of Av1ALAPH81.

The relative levels of human FVIII RNA produced in the mice that received the high vector dose was determined by RNAse protection analysis using RNA isolated from the mouse livers (FIG. 51B), and an anti-sense RNA probe encoding a portion of the FVIII coding region (Connelly et al., 1995b). 50 μg of total cellular RNA isolated from the mouse liver were used in each reaction. The arrow labeled FVIII designates the 212 nt human Factor VIII-specific probe fragment. The lanes marked Neg contain RNA isolated from an uninjected control mouse, and a mouse that received a similar dose of Av1ALH9B, a Factor IX encoding adenoviral vector. The lane marked P contains undigested full-length probe. The lane marked M contains $^{32}$P-labeled DNA molecular weight markers. The lower panel displays a separate RNase protection assay using 20 μg of total cellular mouse liver RNA, and an antisense RNA probe encoding a portion of the mouse glyceraldehyde 3-phosphodehydrogenase (GAPDH) cDNA. The arrow labeled GAPDH designates the 134 nt mouse GAPDH-specific protected probe fragment. With the Factor VIII-specific probe fragment, human FVIII-specific mRNA should protect a 212 nt fragment. A high level of human FVIII-specific RNA was detected with the RNA samples isolated one week post injection (FIG. 51B, lanes 4–7). However, by 22 weeks, human FVIII-specific RNA was undetectable (FIG. 51B, lanes 8–11). No human FVIII-specific protected probe fragment was detected in the uninjected negative control RNA sample (FIG. 51B, lane 2) or with the Av1ALH9B-injected control mouse liver sample (FIG. 51B, lane 3). As an internal RNA standard, the mouse liver RNA samples were analyzed in a separate RNAse protection assay using an anti-sense RNA probe containing a portion of the mouse glyceraldehyde-3-phosphate dehydrogenase (GAPDH) coding region (FIG. 51B, lower panel). Therefore, the dramatic loss of vector DNA and, concordantly, human FVIII-specific RNA from the livers of mice that received the high vector dose parallels the rapid drop in detectable levels of human FVIII in the mouse plasma.

Figure 51C:
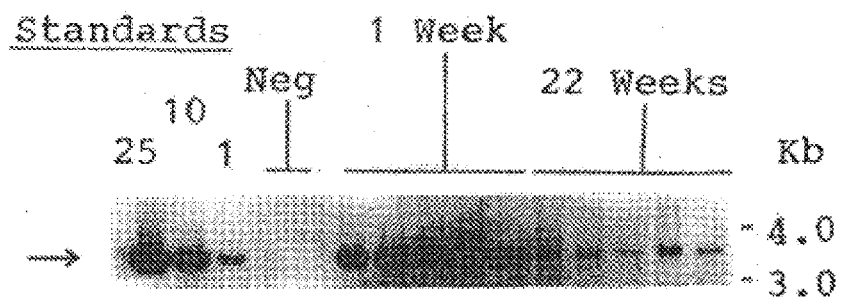
FIG. 51C is a Southern blot analysis of DNA of the livers of mice which received $5 \times 10^8$ pfu of Av1ALAPH81.

FIG. 51C depicts the Southern analysis of mouse liver DNA isolated from mice that received $5 \times 10^8$ pfu of Av1ALAPH81. Each DNA was digested with BamHI, and subjected to Southern analysis. The arrow designates a 3.4 kb fragment containing Av1ALAPH81-derived Factor VIII sequences. The standards were generated by digesting purified Av1ALAPH81 viral DNA in amounts equivalent to 25, 10, and 1 vector copies per cell. DNA size markers are indicated in kb.

In contrast, Southern analysis of DNA isolated from the livers of mice that received the low, $5 \times 10^8$ pfu dose of Av1ALAPH81 (FIG. 51C), revealed that at one week post injection the mice had an average of 7 vector copies per cell (FIG. 51C, lanes 6–10). At 22 weeks, however, the mice had retained an average of 0.5 vector copies per cell (FIG. 51C, lanes 11–15). No vector was detected in an uninjected control mouse DNA sample (FIG. 51C, lane 4), or in a liver DNA sample derived from a mouse injected with Av1ALH9B (FIG. 51C, lane 5). Therefore, mice that received the low vector dose showed only a 14-fold drop in liver vector DNA levels, compared to the dramatic 225-fold decrease in vector copy number observed in the mice that had received the high vector dose.

Figure 51D:
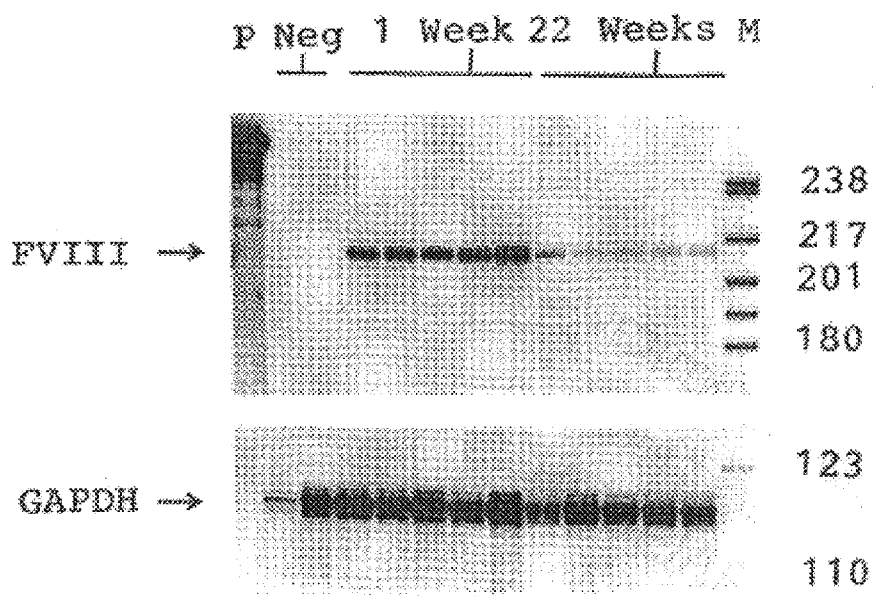
FIG. 51D is an autoradiograph of RNase protection analysis of RNA isolated from the livers of mice which received $5 \times 10^8$ pfu of Av1ALAPH81.

RNAse protection analysis using RNA isolated from the mouse livers (FIG. 51D), and the human FVIII-specific anti-sense RNA probe revealed a high level of FVIII-specific mRNA at both one and 22 weeks after vector administration. 50 µg of total cellular RNA isolated from livers of mice which received $5 \times 10^8$ pfu of Av1ALAPH81 were used in each reaction. The arrow labeled FVIII designates the 212 nt human Factor VIII specific protected probe fragment. The lanes marked Neg contain RNA isolated from an uninjected control mouse, and a mouse that received a similar dose of Av1ALH9B. The lane marked P contains undigested full-length probe. The lane marked M contains $^{32}$P-labeled DNA molecular weight markers. The lower panel displays a separate RNase protection assay using 20 µg of total cellular mouse liver RNA, and an antisense RNA probe encoding a portion of the mouse GAPDH cDNA. The arrow labeled GAPDH designates the 134 nt mouse GAPDH-specific protected fragment. Quantitation by phosphorimager scanning showed only a 3-fold decrease in the FVIII mRNA levels from 1 to 22 weeks. No human FVIII-specific protected probe fragment was detected in the uninjected negative control RNA sample (FIG. 51D, lane 2) or with the Av1ALH9B-injected control mouse liver sample (FIG. 51D, lane 3). As an internal RNA standard, the mouse liver RNA samples were analyzed in a separate RNAse protection assay using the mouse GAPDH anti-sense RNA probe (FIG. 51D, lower panel). Since a significant amount of vector DNA remained in the mouse livers, and a high level of FVIII-specific RNA was detected at 22 weeks after vector administration, it is probable that loss of FVIII expression by 22 weeks was not due to a loss of vector DNA from the mouse livers, or to albumin promoter inactivation.

Hepatotoxicity in Mice that Received High or Low Vector Doses

Figure 52:
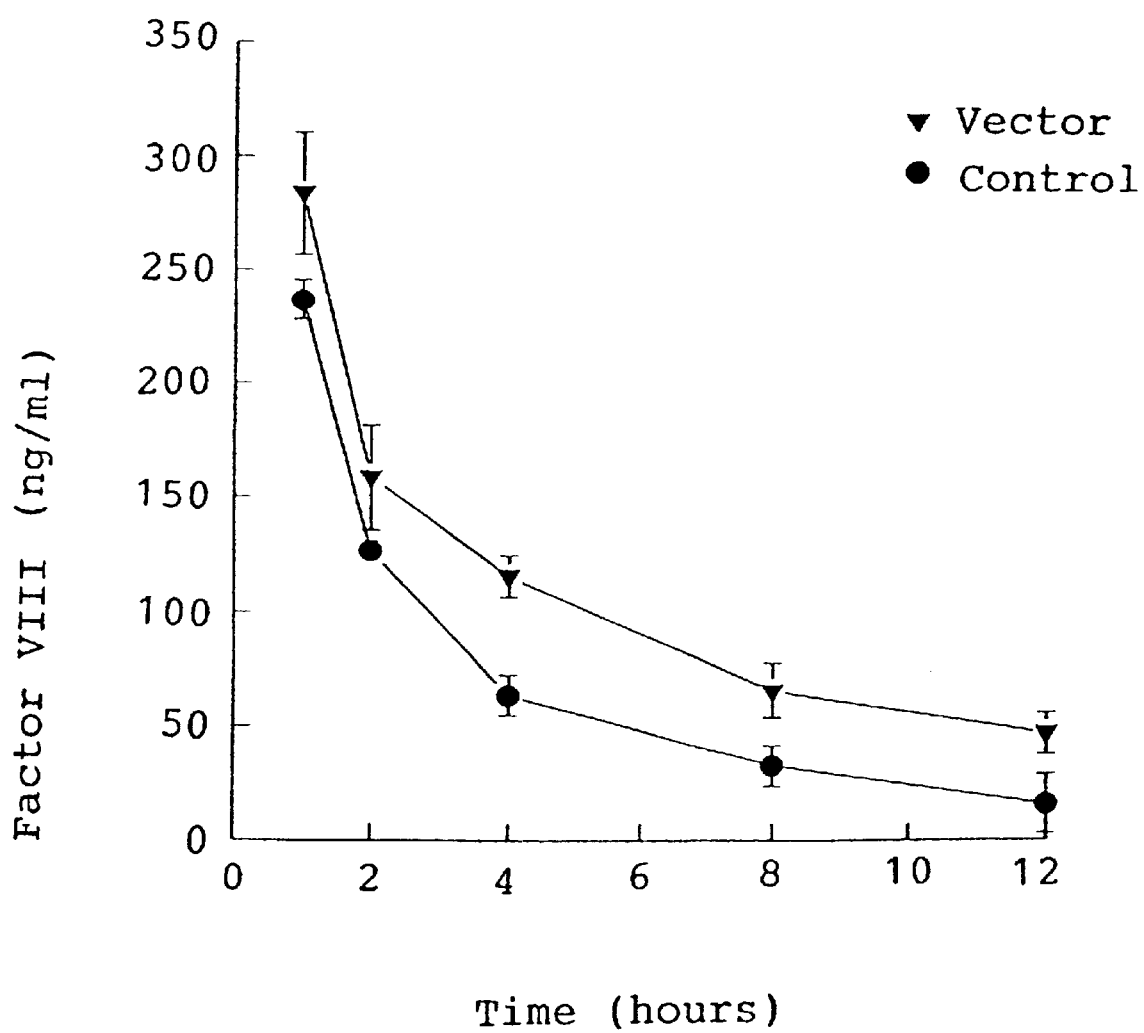
FIG. 52 is a graph showing the half-life of human Factor VIII in plasma samples of mice which received 1,000 ng of purified full-length human Factor VIII four months after the mice received $5 \times 10^8$ pfu of Av1ALAPH81, compared with control mice which received no vector.

In another experiment, purified full-length human Factor VIII protein was administered to 3 mice that had been treated 4 months earlier with $5 \times 10^8$ pfu of Av1ALAPH81, and to 3 untreated mice. Plasma samples were obtained from each mouse at 1 hr., 2 hrs., 4 hrs., 8 hrs., and 12 hrs. after administration, and assayed for human Factor VIII by ELISA. The data are plotted in FIG. 52 as a mean value and standard deviation at each time point.

Since lower vector doses ($5 \times 10^8$ pfu and below) allow sustained expression of human FVIII in mice (FIG. 50), due, at least in part, to the retention of vector DNA in the mouse livers (FIGS. 51 and 52), it is probable that lower vector doses are less hepatotoxic than higher doses, thus decreasing the turn-over of transduced hepatocytes. To show directly that a high dose of Av1ALAPH81 is more toxic than a lower dose, groups of 10 mice each were injected with a high dose ($4 \times 10^9$ pfu) or a low dose ($5 \times 10^8$ pfu) of Av1ALAPH81, injection medium only, or uninjected. Serum samples were collected prior to vector administration, and at the indicated times post injection, and analyzed for the presence of four liver enzymes: aspartate aminotransferase (AST), alanine aminotransferase (ALT), sorbital dehydrogenase (SDH), and alkaline phosphatase (Alk Φ) (FIG. 53). FIG. 53A depicts aspartate aminotransferase (AST) levels. FIG. 53B depicts alanine aminotransferase (ALT) levels. FIG. 53C shows sorbitol dehydrogenase (SDH) levels. FIG. 53D shows alkaline phosphatase levels. A dramatic increase in the levels of all four liver enzymes was detected in the mice that received the highest dose of vector. This increase persisted for at least four weeks post injection. The lower vector dose caused a slight increase in all liver enzymes above the levels of the control groups, or the preinjection samples. Interestingly, by 12 weeks, both vector groups showed enzyme levels similar to the preinjection values and those of the control group. In addition, at the 20 hr, 1 week, and 4 week time points two mice from each group were sacrificed and liver sections analyzed by H&E staining. Liver sections from mice that received a high vector dose showed a liver pathology including loss of the normal sinusodial liver architecture, lymphocytic infiltrate, and the presence of mitotic figures. (personal communication, W. Hall, Pathology Associates Inc., Frederick, Md.; data not shown). However, mice that received the low vector dose looked morphologically normal (personal communication, W. Hall, Pathology Associates, Inc., Frederick, Md.; data not shown). Therefore, these results clearly indicate that a vector dose of $5 \times 10^8$ pfu of Av1ALAPH81 was significantly less hepatotoxic than an 8-fold higher vector dose.

EXAMPLE 15

Treatment of Dog with Av1ALAPH81

A Factor VIII adenoviral vector, Av1ALAPH81 (FIG. 23), was used to treat a Factor FVIII-deficient dog. Two vector lots were prepared (MT2-2 and MT2-3), titered on 293 cells, tested for the presence of RCA (replication competent adenovirus) by PCR analysis directed at E1a sequences, and tested in mice before being used for treatment of the dog. In addition, prior to treatment, samples of the dog's plasma and serum were collected. Plasma samples from the Factor VIII-deficient dog and a normal dog, were tested in the human FVIII specific ELISA (Connelly et al., 1995) to look for cross reactivity of dog FVIII with the human protein. Full-length recombinant FVIII protein generously supplied by Genetics Institute (Cambridge, Mass.) was used to generate a standard curve ranging from 1 to 100 ng/ml. BDD FVIII protein (supplied by Genetics Institute, Cambridge, Mass.) and full-length recombinant FVIII were similarly quantified by this ELISA. Normal dog plasma did not interfere with the assay and the limit of sensitivity with dog plasma samples containing BDD FVIII was 3 to 6 ng/ml. Plasma samples were normally diluted 1:10 for the ELISA. No cross reactivity of the ELISA was found with the normal dog plasma at a 1:10 dilution, and it was verified that the dog's plasma did not cross-react in the ELISA. Plasma from a normal dog and the Factor VIII-deficient dog was analyzed also using the Coatest chromogenic bio-assay (Chromogenix, Mölndal, Sweden). Coatest measures the FVIII-dependent generation of Factor Xa from Factor X, with one unit defined as the amount of FVIII activity in one ml of pooled human plasma, 100 to 200 ng/ml (Vehar et al., 1991). Pooled human plasma (George King Bio-Medical, Inc., Overland Park, Kans.) was used as the FVIII activity standard. It was confirmed that the dog was FVIII-deficient, as no FVIII biological activity in his plasma was detected by Coatest. In addition, the canine FVIII levels were determined in the normal dog plasma to be 5,000 mU/ml, five times the level detected in normal human plasma. To look for the presence of FVIII-inhibitory antibodies, a Coatest assay was performed in which varying amounts of human FVIII protein was added to the dog's plasma samples. If the dog's plasma contained FVIII inhibitory antibodies, it would be expected that FVIII biological activity to be inhibited and therefore, not measurable in the assay. No evidence of FVIII inhibitory antibodies was detected. Finally, the dog's serum was used in an anti-adenovirus antibody assay, to look for the presence of antibodies specific for human Ad5. None were detected.

Administration of Av1ALAPH81

Av1ALAPH81 ($1 \times 10^{12}$ pfu) was administered to the dog, by cephalic vein injection. At days one through seven after vector administration, plasma and serum samples were collected, and analyzed in the following manner: Clinical blood clotting tests: activated clotting time (ACT), and activated partial thromboplastin time (APTT); Coatest assay to measure FVIII biological activity, and FVIII-specific ELISA, to look for the presence of human FVIII. Cuticle bleed time was measured pre-injection, and at days 2 to 7 after treatment. The activated clotting time experiments employed the Vacutainer® sterile evacuated glass tube and the experiments were conducted according to the procedure contained in Vacutainer® Brand Sterile Evacuated Glass Tube, Reorder No. 6522 (Becton, Dickinson and Company, Rutherford, N.J.) (August 1992). The APTT was measured in accordance with Coles, *Veterinary Clinical Pathology,* W. B. Saunders Co., Philadelphia, pg. 106 (1986). Cuticle bleed time was measured in accordance with the procedure described in Giles, et al., *Blood,* Vol. 60, No. 3, pgs. 727–730 (September 1982).

Clinical Clotting Parameter Analyses

The clinical clotting tests, cuticle bleed time, ACT, and APTT were measured prior to vector administration and at several points after treatment. Prior to vector administration, the dog's cuticle bleed time was measured to be greater than 20 minutes, indicative of the hemophiliac phenotype. However, at day 2 after treatment, the dog's cuticle bleed time was reduced to 2.5 minutes. Clotting times under 5 minutes are considered normal. Therefore, administration of Av1ALAPH81 to the dog caused the correction of the animal's bleeding defect. By day 6, however, the cuticle bleed time was measured to be 7 minutes, slightly above the normal levels.

Measurement of the ACT showed the dog's clotting time to be greater than 5 minutes prior to vector treatment. Normal ACT in dogs is less than 2 minutes. At days 2 through 5 ACT values were measured at under 2 minutes, indicating correction of the clotting deficiency. However, by days 6 and 7, the ACT levels had risen back to abnormal levels.

The APTT was measured prior to vector administration and found to be greater than 20 seconds, indicative of a clotting deficiency. Days 2 through 5 after vector treatment, the APTT was measured at or slightly above 10 seconds, indicating normal clotting. However, by days 6 to 8 the APTT values were again measured at abnormal levels.

Measurement of FVIII Expression in Vector-Treated Dog

Figure 54:
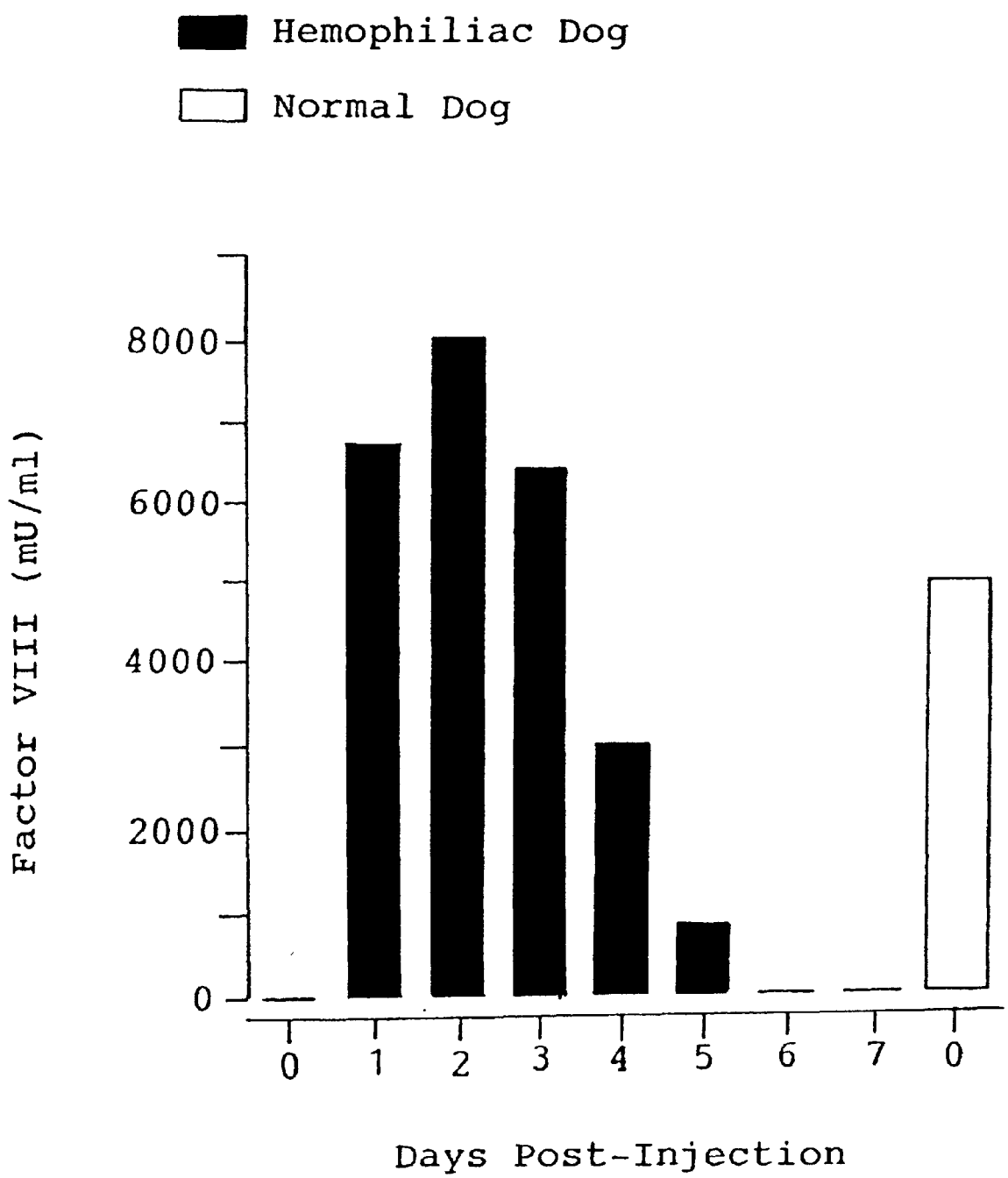
FIG. 54 is a graph of the amount of human Factor VIII present in the plasma of a hemophiliac dog treated with $10^{12}$ pfu of Av1ALAPH81, measured by the Coatest functional assay.

Plasma samples were analyzed using the Coatest assay for FVIII biological activity prior to vector treatment and daily for seven days after vector administration. Biologically active human FVIII was measured using the Coatest bioassay. Analysis of a plasma sample collected prior to Av1ALAPH81 treatment indicated that the dog did not contain detectable levels of functional FVIII. (FIG. 54.) However, at days 1 to 5 after treatment, as shown in FIG. 54, plasma FVIII activity showed a dramatic increase. FVIII expression peaked 2 days after treatment at greater than 8000 mU/ml. These levels are eight-fold higher than the FVIII levels found in normal human plasma. Comparison of the peak FVIII expression level to that of normal dog plasma revealed that the dog was producing FVIII at levels well above that detected in normal dog plasma. These data verify that correction of the clinical clotting parameters, i.e., cuticle bleed time, ACT, and APTT, was due to the production of functional FVIII. In addition, these results show the first example of phenotypic correction of the FVIII deficiency in a clinically relevant animal model. However, by days 6 and 7 FVIII plasma levels were undetectable.

Figure 55:
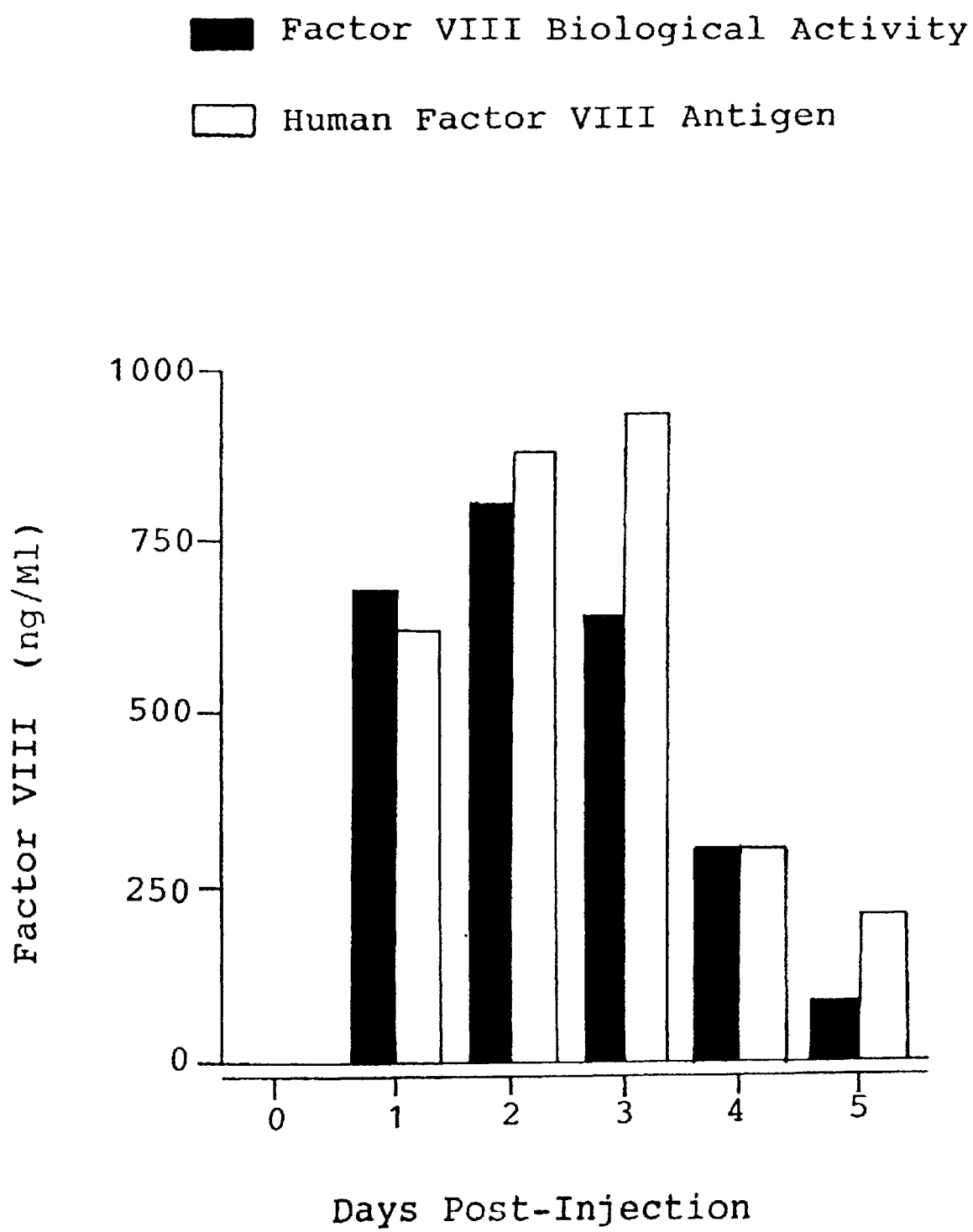
FIG. 55 is a graph of Factor VIII biological activity and of human Factor VIII antigen levels measured by ELISA in the plasma of the hemophiliac dog treated with $10^{12}$ pfu of Av1ALAPH81.

To verify that the FVIII expression measured in the dog's plasma was a direct result of vector administration, i.e., human FVIII, plasma samples were assayed for the presence of human FVIII by ELISA. No human FVIII was measured in the dog's plasma prior to vector administration. At days 2 through 5 high levels of human FVIII were measured, as shown in FIG. 55, verifying that all the FVIII measured in the dog plasma was vector-derived. Conversion of the Coatest activity units to ng/ml using the definition: one unit corresponds to the amount of FVIII in one ml of human pooled plasma, 100 ng/ml, and comparison of human FVIII expression levels detected by ELISA, revealed that similar levels of FVIII were detected by both assays. This observation confirms the accuracy and validity of the human FVIII-specific ELISA.

Analysis of Liver and Spleen Biopsy Samples

Figure 56:
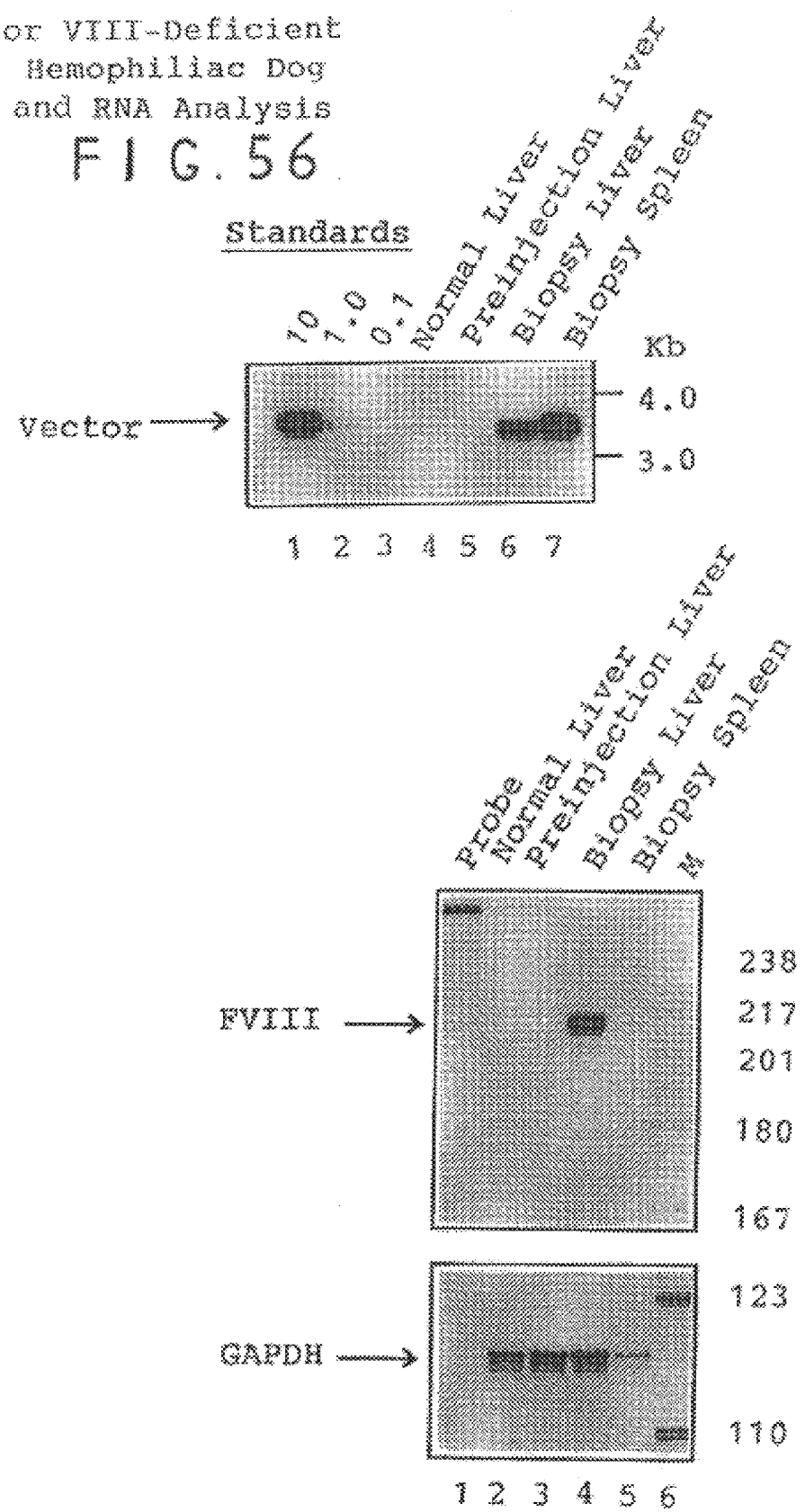
FIG. 56 shows Southern blot and RNase protection analysis of DNA and RNA isolated from the liver and spleen of the hemophiliac dog treated with $10^{12}$ pfu of Av1ALAPH81.

To determine if the decline in FVIII expression levels in the dog's plasma by days 5 to 8 after vector administration was due to loss of vector DNA from the liver or due to transcriptional inactivation of the albumin promoter, an open biopsy was performed 8 days after treatment. DNA and RNA were isolated from liver and spleen samples collected during the biopsy, and used in Southern and RNAse Protection analyses. DNA was isolated from liver and spleen biopsy samples using standard procedures. Briefly, organ sections were minced and incubated overnight in SDS/Proteinase K buffer. This was followed by three phenol/chloroform extractions, one chloroform extraction, ethanol precipitation and resuspension in water. 20 μg of each DNA sample were digested with Bam HI and subjected to Southern analysis, results of which are shown in FIG. 56. The probe, prepared by random oligonucleotide priming, contained human FVIII cDNA sequences from +73 to +1345 (Toole et al., 1984; Wood et al., 1984). The copy number control standards were prepared by adding 1.2 ng, 120 pg or 12 pg of viral DNA, equivalent to 10, 1, and 0.1 vector copies per cell, respectively, to 20 μg of normal dog control liver genomic DNA and digesting with BamHI. The band intensities were quantitated with a Molecular Dynamics PhosphorImager SF. A high level of vector-specific DNA was detected in the liver and spleen biopsy samples, approximately 5 and 10 vector copies per cell, respectively. No vector DNA was observed in a liver biopsy sample collected from a normal dog, or from a pre-injection liver biopsy sample collected from the dog.

To perform the RNA analysis, RNA was isolated from biopsy samples using the RNAzole B (Tel-Test, Friendswood, Tex.) extraction method. RNAse protection analyses were performed using the RNAse Protection Kit II (Ambion, Austin, Tex.). For each sample, quantities of 50 μg of total cellular RNA were hybridized for 12 hrs at 45° C. with $5 \times 10^4$ cpm of a gel-purified RNA probe (See below.), digested with the RNAse A/T1 solution provided with the kit, diluted 1:100, processed as directed, and analyzed on an 8% polyacrylamide-8M urea gel (SequaGel, National Diagnostics, Atlanta, Ga.). The band intensities were quantitated with a Molecular Dynamics PhosphorImager SF. The FVIII probe template, pGemSRpr, was constructed by inserting the 204 bp Sac I-Eco RI fragment isolated from pMT2LA (provided by Genetics Institute, Cambridge, Mass.) (Toole et al., 1986) into pGem4Z (Promega, Madison, Wis.) cut with Sac I and Eco RI. The RNA analysis revealed the presence of a high level of FVIII-specific RNA only in the liver biopsy sample. (FIG. 56.) No FVIII-specific RNA was detected in the spleen biopsy sample, the preinjection liver sample, or in the normal dog liver RNA sample. To verify the integrity of the RNA in each sample, a separate RNAse protection analysis was performed using a mouse-specific glyceraldehyde 3-phosphate dehydrogenase (GAPDH) probe. The GAPDH probe template was generated from the pTRI-GAPDH mouse plasmid (Ambion, Austin, Tex.) digested with Sty I. A similar amount of RNA was detected in each of the liver RNA samples. However, less GAPDH-specific RNA was detected in the spleen-derived RNA sample, probably reflecting the normal variation in GAPDH levels between different organs. These results indicate that the albumin promoter remained transcriptionally active 8 days after vector administration. In addition, consistent with previous observations in mice, these data reveal that the albumin promoter functioned in a liver-specific manner in the dog, as no FVIII-specific RNA was detected in the spleen biopsy sample although the spleen contained more vector copies per cell than the liver. Taken together, these results indicate that the loss of FVIII expression by 8 days after treatment was not due to a complete loss of vector DNA from the treated animal, nor to the transcriptional inactivation of the albumin promoter. Previous studies have shown that FVIII-deficient dogs have a high likelihood of developing human FVIII inhibitory antibodies, (Littlewood and Barrowcliffe, 1987; Thrombosis and Haemostasis, Vol. 57, pages 314–321). Therefore, the drop in FVIII plasma levels between 5 to 8 days after treatment may have been due to the presence of FVIII inhibitory antibodies in the dog's plasma.

EXAMPLE 16

Generation of Human Factor VIII-Encoding Recombinant Adenoviruses Av1AP3'H81, Av1ALAP3'H81, Av1APH8H9, and Av1ALAPH8H9 Construction of Av1AP3'H81 and Av1ALAP3'H81

The adenoviral shuttle plasmid, pAvAP3'H81 was constructed by replacing the FVIII 3' UTR (215 bp) in the plasmid, pAvAPH81 (FIG. 18), with the Apo A1 3' UTR and poly(A) signal (Genbank #XO7496, nts 2024 to 2143), and used to generate the recombinant adenoviral vector, Av1AP3'H81 by procedures hereinabove described. The shuttle plasmid, pAvALAP3'H81, was constructed by replacing the FVIII 3' UTR (215 bp) in the plasmid, pAvALAPH81 (FIG. 20) with the Apo A1 sequences described above and used to generate the recombinant adenoviral vector, Av1ALAP3'H81 (FIG. 57) by procedures hereinabove described.
Construction of Av1APH8H9 and Av1ALAPHBH9

Figure 57:
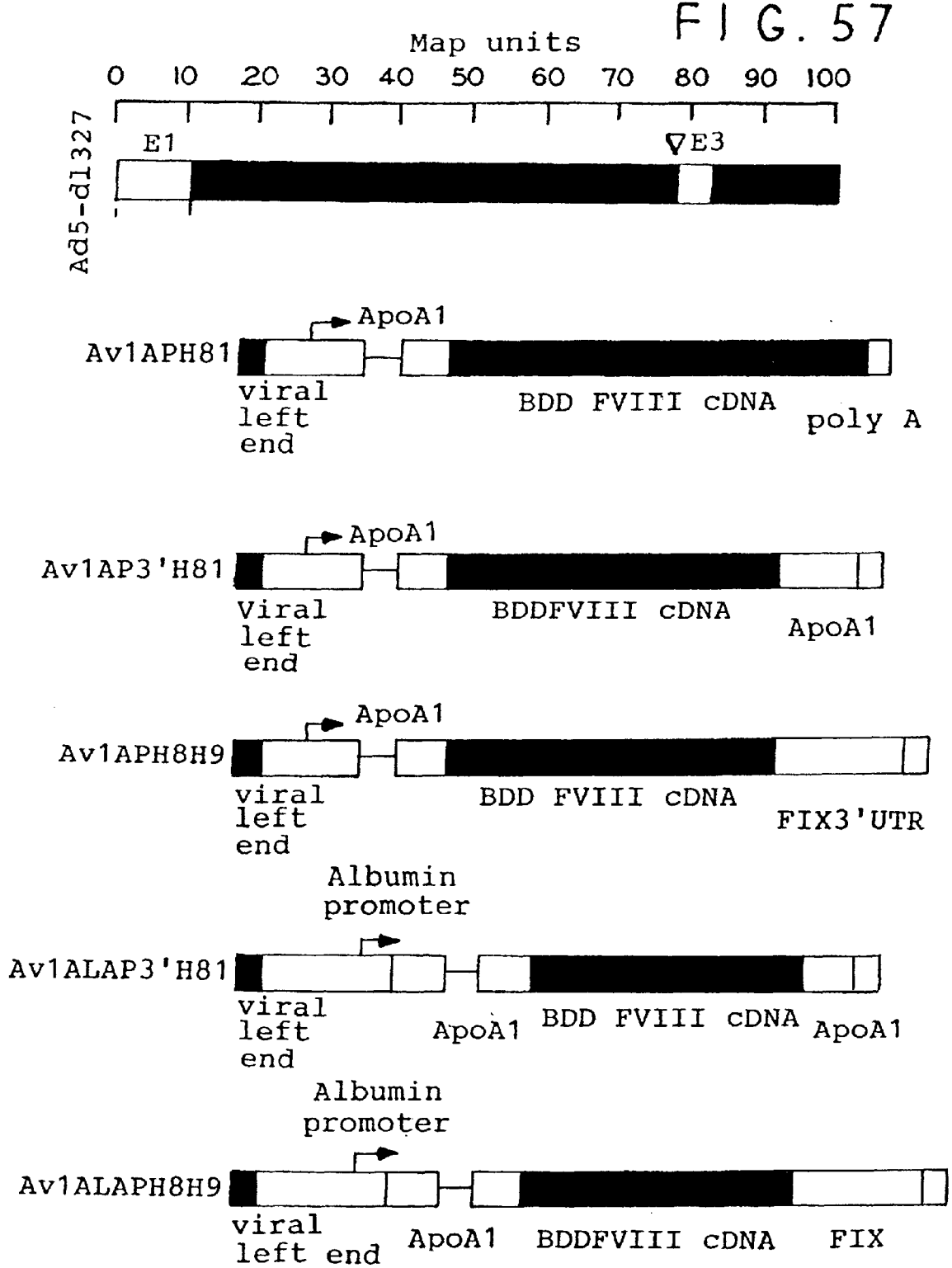
FIG. 57 is a schematic of Ad5-dl327, Av1APH81, Av1AP3'H81, Av1APH8H9, Av1ALAP3'H81, and Av1ALAPH8H9.
Figure 58:
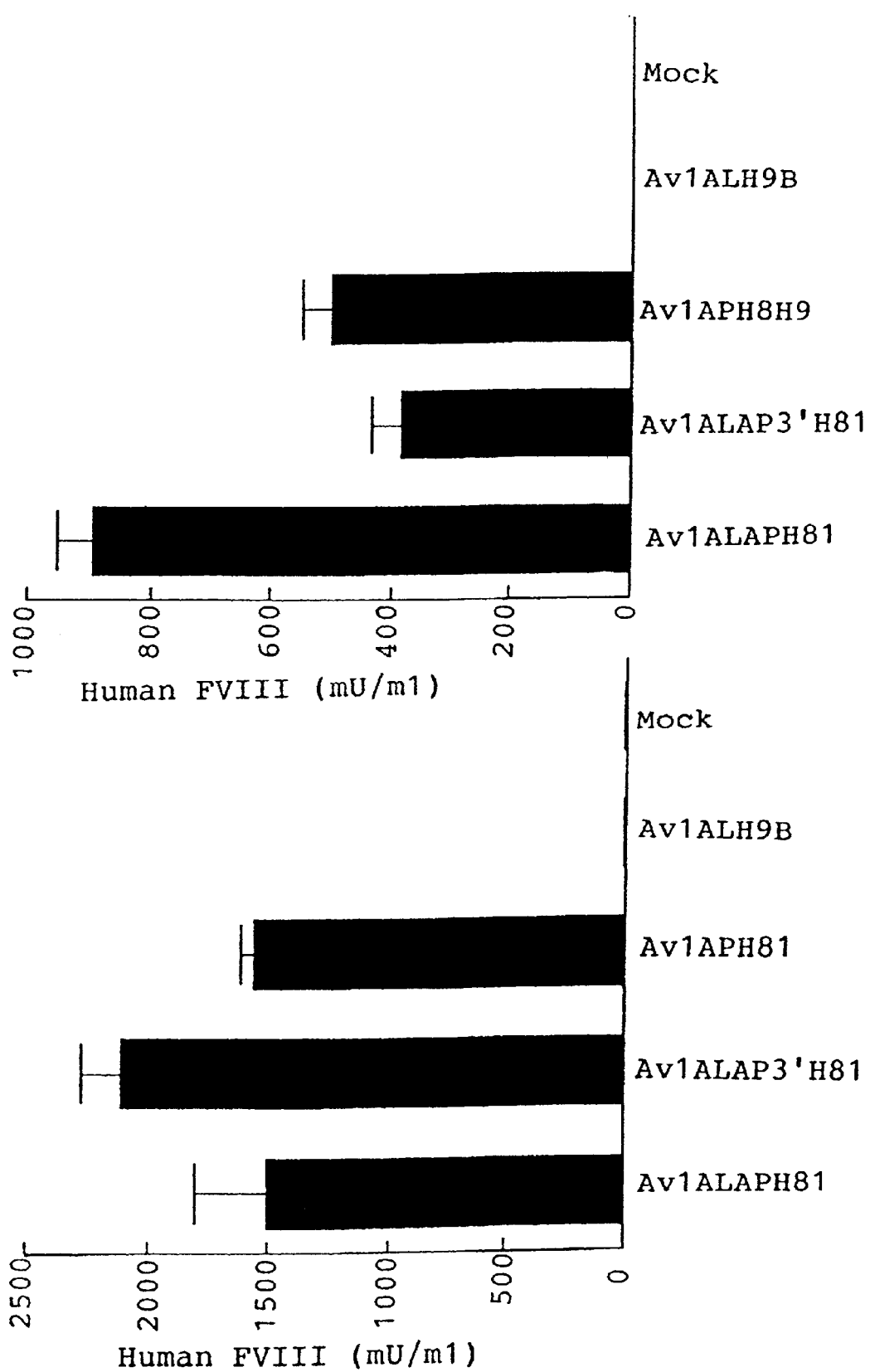
FIG. 58 is a graph of expression of human Factor VIII in HepG2 cells transduced with Av1ALAPH81, Av1ALAP3'H81, Av1APH81, Av1ALH9B, Av1AP3'H81, or Av1APH8H9.
Figure 59:
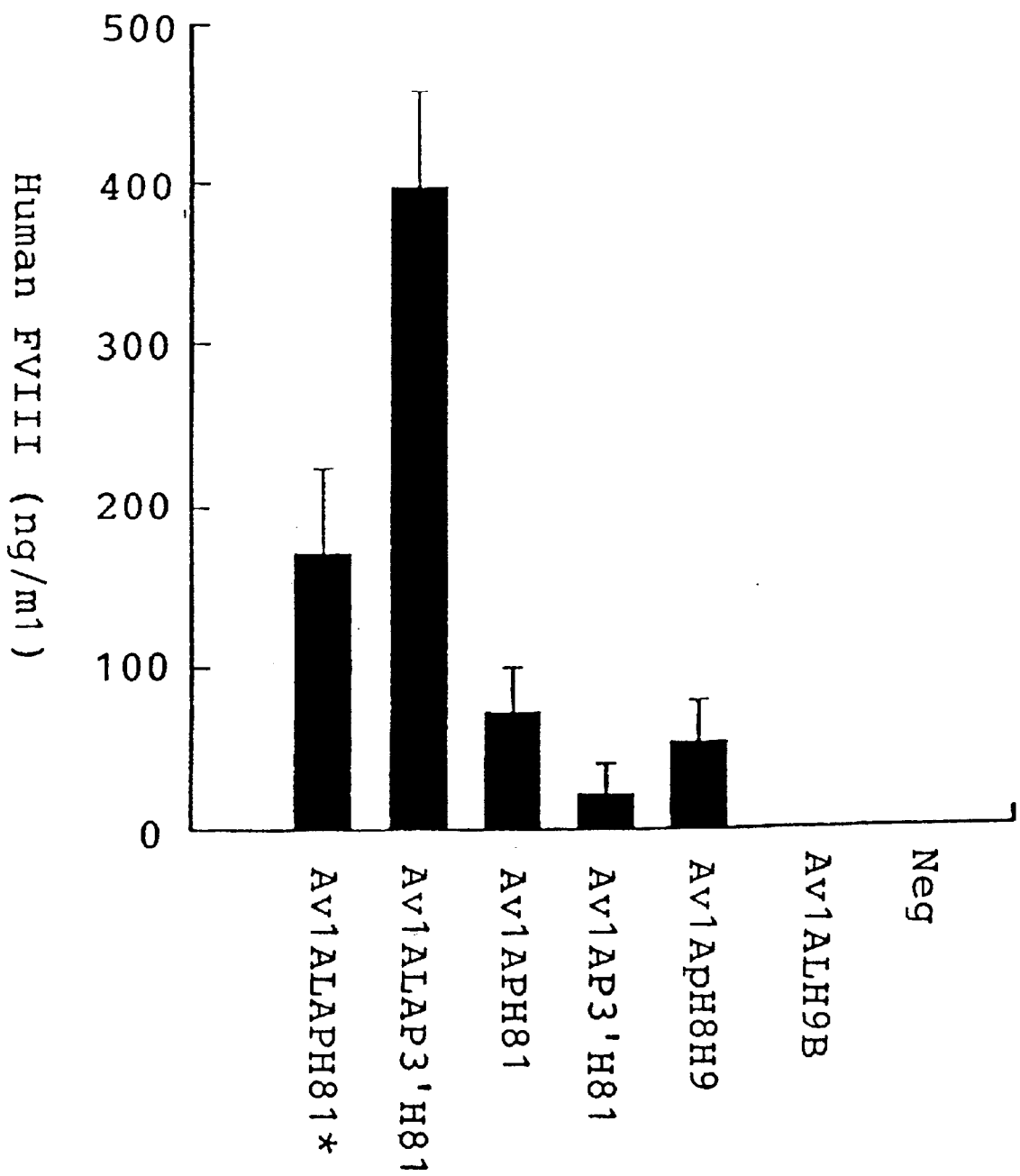
FIG. 59 is a graph of human Factor VIII expression in mice which were given $4 \times 10^9$ pfu of Av1ALAP3'H81, Av1APH81, Av1AP3'H81, Av1APH8H9, or Av1ALH9B, or were given $5 \times 10^8$ pfu of Av1ALAPH81.

The shuttle plasmid, pAvAPH8H9 was constructed by replacing the FVIII 3' UTR (215 bp) in the plasmid, pAvAPH81 (FIG. 18), with the 3' UTR and poly(A) signals of the human FIX gene (1.7 kb). In a similar manner, pAvALAPH8H9 was constructed by replacing the FVIII 3' UTR (215 bp) in pAvALAPH81 (FIG. 20) with the FIX 3' sequences. The plasmid, pAvAPH8H9 was used to generate Av1APH8H9 by procedures hereinabove described. Similarly, the plasmid, pAvALAPH8H9, was used to generate Av1ALAPH8H9. (FIG. 57). However, instead of using the large Cla I fragment isolated from dl327, the large Cla I fragment was isolated from dl7001 (Ranheim et al., 1993; Journal of Virology, Vol. 67, pages 2159–2167), and used in the cotransfection of 293 cells as described. It was necessary to use dl7001 instead of dl327 because dl7001 contains a larger deletion of the E3 region than does dl327. Due to the large size of the shuttle plasmid, pAvALAPH8H9, it was necessary to use dl7001 to generate a stable recombinant adenoviral vector.
In vitro Analysis of FVIII Adenoviral Vectors To determine if the FVIII adenoviral vectors produced functional FVIII in vitro, HepG2, human hepatoma cells, were transduced with each FVIII adenoviral vector, Av1ALAPH81, Av1ALAP3'H81, Av1APH81 (FIG. 23), Av1AP3'H81, Av1APH8H9, or Av1ALH9B (an albumin promoted human FIX adenoviral vector used as a negative control), at an MOI of 30, in triplicate infections. Also, triplicate wells of a six-well plate were also mock infected. 12 hours after transduction, media was changed, and 24 hours later, media was assayed for the presence of functional FVIII by the Coatest assay. The data are plotted as a mean value and standard deviation. The results of two separate experiments (FIG. 58) are displayed, and reveal that all FVIII vectors produce high levels of functional FVIII in vitro.
Analysis of FVIII Adenoviral Viral Vectors in Mice To determine if the FVIII adenoviral vectors produced human FVIII when administered to mice, a dose of $4 \times 10^9$ pfu of Av1ALAP3'H81, Av1APH81, Av1AP3'H81, Av1APH8H9 or Av1ALH9B was administered to groups of five mice each. Expression from the new vectors was compared to that obtained with a group of five mice that had received a dose of $5 \times 10^8$ pfu of Av1ALAPH81. One week after vector administration, human FVIII plasma levels in the mice were measured by ELISA. Data are shown as a mean value and standard deviation. (FIG. 59.) The data reveal that all vectors are functional in vivo. However, expression in mice that received a high dose of Av1APH81, Av1AP3'H81, and Av1APH8H9 was significantly lower than that detected from mice injected with a low dose of Av1ALAPH81. In addition, expression from mice injected with a high dose of Av1ALAP3'H81 was higher than that detected in mice injected with a low dose of Av1ALAPH81. However, injection of $4 \times 10^9$ pfu of Av1ALAPH81 to mice resulted in expression of 1000 to 2000 ng/ml of human FVIII (data not shown), significantly higher than that detected in mice that received a similar dose of Av1ALAP3'H81 (400 ng/ml).

EXAMPLE 17

Generation of Factor IX Adenoviral Vectors Having A Deleted or Mutated Tripartite Leader (TPL) Sequence The adenoviral vector Av1H9FR was reconstructed to remove an open reading frame (orf) in the tripartite leader (TPL) between the RSV promoter and the Factor IX cDNA. FIG. 60 shows a diagram of the left end of Av1H9FR. The vector begins with natural adenovirus serotype 5 (Ad5) sequences, starting with the inverted terminal repeat (ITR) followed by the packaging signal (ψ) and the E1a enhancer (E1a enh). This is followed by the RSV promoter and the Ad5 TPL. Downstream of the TPL is the human Factor IX cDNA (huFIX). In Av1H9B, Av1H9D, Av1H9ER, and Av1H9FR, an ATG in the context of a reasonably good Kozak consensus sequence is situated immediately upstream of the TPL. A 63 amino acid open reading frame (orf) follows the ATG. Translation initiation at this ATG would likely have a strong deleterious effect on translation of the Factor IX cDNA.

Two new vectors were generated. The first one, Av1H9F1, lacks the entire TPL, including the orf. The second vector, Av1H9F2, retains the TPL; however, the ATG at the beginning of the TPL was replaced with a CTG.

Figure 39:
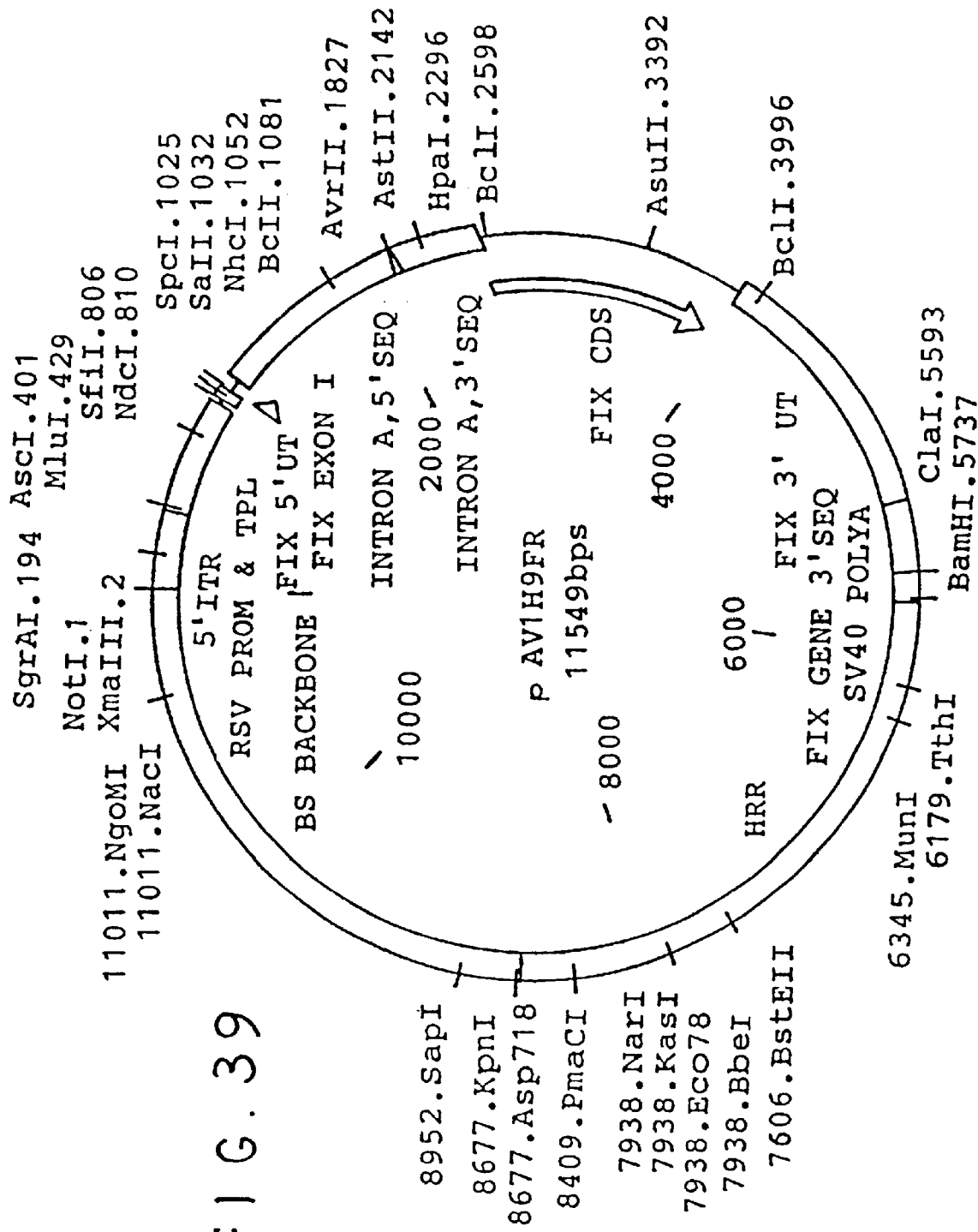
FIG. 39 is a map of plasmid pAV1H9FR.

The first step in the construction of Av1H9F1 was to delete the TPL from the shuttle plasmid pAv1H9FR (FIG. 39). This was accomplished by digesting the plasmid with the restriction enzymes SfiI and SpeI. The resulting DNA fragments were subjected to electrophoresis in an agarose gel and the larger of the two fragments was recovered by electroelution. The ends of the DNA were made blunt by treatment with T4 DNA Polymerase, then the fragment was circularized by ligation. An aliquot of the ligation mixture was used to transform competent DH5 *E. coli,* and ampicillin-resistant colonies were isolated. Several colonies were amplified and miniprep DNA was analyzed by restriction enzyme digestion. A clone with the correct restriction pattern was identified and expanded. The resulting shuttle plasmid, pAvS15H9F, was co-transfected with the large DNA fragment of ClaI digested Ad-dl327 into 293 cells. Two weeks later, infectious recombinant adenoviral vector plaques were picked, expanded, and screened for expression of Factor IX by ELISA. One positive clone was purified by isolating a single plaque, then amplified. The resulting recombinant adenoviral vector was called Av1H9F1. Its integrity was verified by restriction enzyme diagnostics. The structure of the left end of this vector is shown in FIG. 60. The extreme left end of the vector contains the normal sequence of adenovirus serotype 5 (Ad5), including the inverted terminal repeat (ITR). This region is followed by the RSV promoter, which is immediately followed by the human Factor IX cDNA. The ATG shown in the schematic for Av1H9F1 represents the Factor IX start codon.

To construct Av1H9F2, the shuttle plasmid pAv1H9FR was digested with the restriction enzyme SfiI, the DNA ends were made blunt using T4 DNA Polymerase, and the DNA molecule was recircularized by ligation. Competent DH5 cells were transformed and ampicillin-resistant clones were amplified and screened by restriction enzyme digestion of miniprep DNA. A positive clone was identified and the resulting shuttle plasmid was referred to as pAvS17H9F.

Subsequently, 293 cells were cotransfected with pAvS17H9F and the large DNA fragment of ClaI digested Ad-dl327. Recombinant adenoviral vector plaques were picked, expanded, and screened for expression of Factor IX by ELISA. A positive clone was identified and amplified, thus generating the vector Av1H9F2. A schematic of the left end of the vector is shown in FIG. 60. Av1H9F2 is identical to Av1H9FR, except for a 5 base pair deletion at the beginning of the TPL, which effectively changes the ATG into a CTG. The structure of the vector was verified by restriction enzyme diagnostics and by DNA sequence analysis of the region between the RSV promoter and the 3' untranslated region of the Factor IX cDNA.

The parent vector, Av1H9FR, and the two new vectors, Av1H9F1 and Av1H9F2, were compared in mice for their ability to mediate expression of human Factor IX. Five mice received $5 \times 10^7$ pfu and another 5 mice received $1 \times 10^8$ pfu of vector via tail vein injection. One week later, plasma samples were prepared and analyzed by ELISA for human Factor IX. The plasma level of Factor IX for each mouse is shown in Table VII.

TABLE VII

| Mouse | Vector | Dose | ng/ml huFIX |
|---|---|---|---|
| 1 | Av1H9FR | $1 \times 10^8$ | 3155 |
| 2 | Av1H9FR | $1 \times 10^8$ | 1723 |
| 3 | Av1H9FR | $1 \times 10^8$ | 996 |
| 4 | Av1H9FR | $1 \times 10^8$ | 574 |
| 5 | Av1H9FR | $1 \times 10^8$ | 704 |
| 6 | Av1H9FR | $5 \times 10^7$ | 93 |
| 7 | Av1H9FR | $5 \times 10^7$ | 150 |
| 8 | Av1H9FR | $5 \times 10^7$ | 153 |
| 9 | Av1H9FR | $5 \times 10^7$ | 97 |
| 10 | Av1H9F1 | $1 \times 10^8$ | 427 |
| 11 | Av1H9F1 | $1 \times 10^8$ | 1840 |
| 12 | Av1H9F1 | $1 \times 10^8$ | 266 |
| 13 | Av1H9F1 | $1 \times 10^8$ | 1626 |
| 14 | Av1H9F1 | $1 \times 10^8$ | 331 |
| 15 | Av1H9F1 | $5 \times 10^7$ | 254 |
| 16 | Av1H9F1 | $5 \times 10^7$ | 129 |
| 17 | Av1H9F1 | $5 \times 10^7$ | 91 |
| 18 | Av1H9F1 | $5 \times 10^7$ | 113 |
| 19 | Av1H9F1 | $5 \times 10^7$ | 64 |
| 20 | Av1H9F2 | $1 \times 10^8$ | 14308 |
| 21 | Av1H9F2 | $1 \times 10^8$ | 20313 |
| 22 | Av1H9F2 | $1 \times 10^8$ | 10886 |
| 23 | Av1H9F2 | $1 \times 10^8$ | 5683 |
| 24 | Av1H9F2 | $1 \times 10^8$ | 5927 |
| 25 | Av1H9F2 | $5 \times 10^7$ | 1035 |
| 26 | Av1H9F2 | $5 \times 10^7$ | 867 |
| 27 | Av1H9F2 | $5 \times 10^7$ | 1755 |
| 28 | Av1H9F2 | $5 \times 10^7$ | 2164 |
| 29 | Av1H9F2 | $5 \times 10^7$ | 3220 |

To normalize the expression levels to the vector content in the liver, the animals were sacrificed and DNA from their livers was analyzed by Southern (FIG. 61). The results show that Av1H9F2 expressed approximately 10–15 times higher levels of Factor IX than either Av1H9FR or Av1H9F1, even though the vector content in the liver was nearly the same for each vector. The average level of Factor IX expression for each cohort of mice is shown above the Southern blots.

All patents, publications, and database accession numbers, and depository accession numbers referenced in this specification are indicative of the level of skill of persons in the art to which the invention pertains. The disclosures of all such patents, publications (including published patent applications), and database accession numbers, and depository accession numbers are specifically incorporated herein by reference in their entirety to the same extent as if each such individual patent, publication, and database accession number, and depository accession number were specifically and individually indicated to be incorporated by reference.

It is to be understood, however, that the scope of the present invention is not to be limited to the specific embodiments described above. The invention may be practiced other than as particularly described and still be within the scope of the accompanying claims.

SEQUENCE LISTING (1) GENERAL INFORMATION:

(iii) NUMBER OF SEQUENCES: 7

(2) INFORMATION FOR SEQ ID NO: 1:

(i) SEQUENCE CHARACTERISTICS:
        (A) LENGTH: 32 bases
        (B) TYPE: nucleic acid
        (C) STRANDEDNESS: single
        (D) TOPOLOGY: linear (ii) MOLECULE TYPE: oligonucleotide (ix) FEATURE:
         (A) NAME/KEY:  PCR primer; oligo
             MGM8.293

(xi) SEQUENCE DESCRIPTION: SEQ ID NO: 1:

GGCTAGACGC GTGCTATGAC CATGATTACG AA                                32

(2) INFORMATION FOR SEQ ID NO: 2:

(i) SEQUENCE CHARACTERISTICS:
        (A) LENGTH: 43 bases
        (B) TYPE: nucleic acid
        (C) STRANDEDNESS: single
        (D) TOPOLOGY: linear (ii) MOLECULE TYPE: oligonucleotide (ix) FEATURE:
         (A) NAME/KEY:  PCR primer; oligo MGM5.293

(xi) SEQUENCE DESCRIPTION: SEQ ID NO: 2:

GGTACGGATC CATCGATGTC GACGCCGGAA AGGTGATCTG TGT                    43

(2) INFORMATION FOR SEQ ID NO: 3:

(i) SEQUENCE CHARACTERISTICS:
        (A) LENGTH: 38 bases
        (B) TYPE: nucleic acid
        (C) STRANDEDNESS: single
        (D) TOPOLOGY: linear (ii) MOLECULE TYPE: oligonucleotide (ix) FEATURE:
         (A) NAME/KEY:  PCR primer; oligo SSC 1.593

(xi) SEQUENCE DESCRIPTION: SEQ ID NO: 3:

GCTCTAGAAC GCGTCGGTAC CCGGGAGACC TGCAAGCC                          38

(2) INFORMATION FOR SEQ ID NO: 4:

(i) SEQUENCE CHARACTERISTICS:
        (A) LENGTH: 45 bases
        (B) TYPE: nucleic acid
        (C) STRANDEDNESS: single
        (D) TOPOLOGY: linear (ii) MOLECULE TYPE: oligonucleotide (ix) FEATURE:
         (A) NAME/KEY:  PCR primer; oligo SSC 2.593

(xi) SEQUENCE DESCRIPTION: SEQ ID NO: 4:

GGAATTCGAG CTCTATTTGC ATCCTGAAGG GCCGTGGGGA CCTGG                  45

(2) INFORMATION FOR SEQ ID NO: 5:

(i) SEQUENCE CHARACTERISTICS:
        (A) LENGTH: 35 bases
        (B) TYPE: nucleic acid
        (C) STRANDEDNESS: single
        (D) TOPOLOGY: linear (ii) MOLECULE TYPE: oligonucleotide (ix) FEATURE:
        (A) NAME/KEY: PCR primer; oligo SSC 3.593

(xi) SEQUENCE DESCRIPTION: SEQ ID NO: 5:

```
GAATTCGTCG ACAGAGACTG CGAGAAGGAG GTGCG                               35
```

(2) INFORMATION FOR SEQ ID NO: 6:

(i) SEQUENCE CHARACTERISTICS:
        (A) LENGTH: 1548 bases
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: Factor IX cDNA (xi) SEQUENCE DESCRIPTION: SEQ ID NO: 6:

```
AGGTTATGCA GCGCGTGAAC ATGATCATGG CAGAATCACC AGGCCTCATC ACCATCTGCC    60
TTTTAGGATA TCTACTCAGT GCTGAATGTA CAGTTTTTCT TGATCATGAA AACGCCAACA   120
AAATTCTGAA TCGGCCAAAG AGGTATAATT CAGGTAAATT GGAAGAGTTT GTTCAAGGGA   180
ACCTTGAGAG AGAATGTATG GAAGAAAAGT GTAGTTTTGA AGAAGCACGA GAAGTTTTTG   240
AAAACACTGA AGAACAACT GAATTTTGGA AGCAGTATGT TGATGGAGAT CAGTGTGAGT    300
CCAATCCATG TTTAAATGGC GGCAGTTGCA AGGATGACAT TAATTCCTAT GAATGTTGGT   360
GTCCCTTTGG ATTTGAAGGA AGAACTGTG AATTAGATGT AACATGTAAC ATTAAGAATG    420
GCAGATGCGA GCAGTTTTGT AAAAATAGTG CTGATAACAA GGTGGTTTGC TCCTGTACTG   480
AGGGATATCG ACTTGCAGAA AACCAGAAGT CCTGTGAACC AGCAGTGCCA TTTCCATGTG   540
GAAGAGTTTC TGTTTCACAA ACTTCTAAGC TCACCCGTGC TGAGACTGTT TTTCCTGATG   600
TGGACTATGT AAATTCTACT GAAGCTGAAA CCATTTTGGA TAACATCACT CAAAGCACCC   660
AATCATTTAA TGACTTCACT CGGGTTGTTG GTGGAGAAGA TGCCAAACCA GGTCAATTCC   720
CTTGGCAGGT TGTTTTGAAT GGTAAAGTTG ATGCATTCTG TGGAGGCTCT ATCGTTAATG   780
AAAAATGGAT TGTAACTGCT GCCCACTGTG TTGAAACTGG TGTTAAAATT ACAGTTGTCG   840
CAGGTGAACA TAATATTGAG GAGACAGAAC ATACAGAGCA AAAGCGAAAT GTGATTCGAA   900
TTATTCCTCA CCACAACTAC AATGCAGCTA TTAATAAGTA CAACCATGAC ATTGCCCTTC   960
TGGAACTGGA CGAACCCTTA GTGCTAAACA GCTACGTTAC ACCTATTTGC ATTGCTGACA  1020
AGGAATACAC GAACATCTTC CTCAAATTTG GATCTGGCTA TGTAAGTGGC TGGGGAAGAG  1080
TCTTCCACAA AGGGAGATCA GCTTTAGTTC TTCAGTACCT TAGAGTTCCA CTTGTTGACC  1140
GAGCCACATG TCTTCGATCT ACAAAGTTCA CCATCTATAA CAACATGTTC TGTGCTGGCT  1200
TCCATGAAGG AGGTAGAGAT TCATGTCAAG GAGATAGTGG GGACCCCAT GTTACTGAAG   1260
TGGAAGGGAC CAGTTTCTTA ACTGGAATTA TTAGCTGGGG TGAAGAGTGT GCAATGAAAG  1320
```

```
GCAAATATGG AATATATACC AAGGTATCCC GGTATGTCAA CTGGATTAAG GAAAAAACAA    1380

AGCTCACTTA ATGAAAGATG GATTTCCAAG GTTAATTCAT TGGAATTGAA AATTAACAGG    1440

GCCTCTCACT AACTAATCAC TTTCCCATCT TTTGTTAGAT TTGAATATAT ACATTCTATG    1500

ATCATTGCTT TTTCTCTTTA CAGGGAGAA TTTCATATTT TACCTGAG                  1548
```

(2) INFORMATION FOR SEQ ID NO: 7:

(i) SEQUENCE CHARACTERISTICS:
        (A) LENGTH: 4629 bases
        (B) TYPE: nucleic acid
        (C) STRANDEDNESS: single
        (D) TOPOLOGY: linear (ii) MOLECULE TYPE: cDNA primer (ix) FEATURE:
        (A) NAME/KEY: Factor VIII cDNA with
            B domain deleted (xi) SEQUENCE DESCRIPTION: SEQ ID NO: 7:

```
ATGCAAATAG AGCTCTCCAC CTGCTTCTTT CTGTGCCTTT TGCGATTCTG CTTTAGTGCC      60

ACAAGAAGAT ACTACCTGGG TGCAGTGGAA CTGTCATGGG ACTATATGCA AAGTGATCTC     120

GGTGAGCTGC CTGTGGACGC AAGATTTCCT CCTAGAGTGC CAAAATCTTT TCCATTCAAC     180

ACCTCAGTCG TGTACAAAAA GACTCTGTTT GTAGAATTCA CGGTTCACCT TTTCAACATC     240

GCTAAGCCAA GGCCACCCTG GATGGGTCTG CTAGGTCCTA CCATCCAGGC TGAGGTTTAT     300

GATACAGTGG TCATTACACT TAAGAACATG GCTTCCCATC CTGTCAGTCT TCATGCTGTT     360

GGTGTATCCT ACTGGAAAGC TTCTGAGGGA GCTGAATATG ATGATCAGAC CAGTCAAAGG     420

GAGAAAGAAG ATGATAAAGT CTTCCCTGGT GGAAGCCATA CATATGTCTG GCAGGTCCTG     480

AAAGAGAATG GTCCAATGGC CTCTGACCCA CTGTGCCTTA CCTACTCATA TCTTTCTCAT     540

GTGGACCTGG TAAAAGACTT GAATTCAGGC CTCATTGGAG CCCTACTACT ATGTAGAGAA     600

GGGAGTCTGG CCAAGGAAAA GACACAGACC TTGCACAAAT TTATACTACT TTTTGCTGTA     660

TTTGATGAAG GGAAAAGTTG GCACTCAGAA ACAAAGAACT CCTTGATGCA GGATAGGGAT     720

GCTGCATCTG CTCGGGCCTG GCCTAAAATG CACACAGTCA ATGGTTATGT AAACAGGTCT     780

CTGCCAGGTC TGATTGGATG CCACAGGAAA TCAGTCTATT GGCATGTGAT TGGAATGGGC     840

ACCACTCCTG AAGTGCACTC AATATTCCTC GAAGGTCACA CATTTCTTGT GAGGAACCAT     900

CGCCAGGCGT CCTTGGAAAT CTCGCCAATA ACTTTCCTTA CTGCTCAAAC ACTCTTGATG     960

GACCTTGGAC AGTTTCTACT GTTTTGTCAT ATCTCTTCCC ACCAACATGA TGGCATGGAA    1020

GCTTATGTCA AAGTAGACAG CTGTCCAGAG GAACCCCAAC TACGAATGAA AAATAATGAA    1080

GAAGCGGAAG ACTATGATGA TGATCTTACT GATTCTGAAA TGGATGTGGT CAGGTTTGAT    1140

GATGACAACT CTCCTTCCTT TATCCAAATT CGCTCAGTTG CCAAGAAGCA TCCTAAAACT    1200

TGGGTACATT ACATTGCTGC TGAAGAGGAG GACTGGGACT ATGCTCCCTT AGTCCTCGCC    1260

CCCGATGACA GAAGTTATAA AAGTCAATAT TTGAACAATG GCCCTCAGCG GATTGGTAGG    1320

AAGTACAAAA AAGTCCGATT TATGGCATAC ACAGATGAAA CCTTTAAGAC TCGTGAAGCT    1380

ATTCAGCATG AATCAGGAAT CTTGGGACCT TTACTTTATG GGGAAGTTGG AGACACACTT    1440

TTGATTATAT TTAAGAATCA AGCAAGCAGA CCATATAACA TCTACCCTCA CGGAATCACT    1500

GATGTCCGTC CTTTGTATTC AAGGAGATTA CCAAAAGGTG TAAAACATTT GAAGGATTTT    1560

CCAATTCTGC CAGGAGAAAT ATTCAAATAT AAATGGACAG TGACTGTAGA AGATGGGCCA    1620
```

```
ACTAAATCAG ATCCTCGGTG CCTGACCCGC TATTACTCTA GTTTCGTTAA TATGGAGAGA    1680

GATCTAGCTT CAGGACTCAT TGGCCCTCTC CTCATCTGCT ACAAAGAATC TGTAGATCAA    1740

AGAGGAAACC AGATAATGTC AGACAAGAGG AATGTCATCC TGTTTTCTGT ATTTGATGAG    1800

AACCGAAGCT GGTACCTCAC AGAGAATATA CAACGCTTTC TCCCCAATCC AGCTGGAGTG    1860

CAGCTTGAGG ATCCAGAGTT CCAAGCCTCC AACATCATGC ACAGCATCAA TGGCTATGTT    1920

TTTGATAGTT TGCAGTTGTC AGTTTGTTTG CATGAGGTGG CATACTGGTA CATTCTAAGC    1980
ATTGGAGCAC AGACTGACTT CCTTTCTGTC TTCTTCTCTG GATATACCTT CAAACACAAA    2040

ATGGTCTATG AAGACACACT CACCCTATTC CCATTCTCAG GAGAAACTGT CTTCATGTCG    2100

ATGGAAAACC CAGGTCTATG GATTCTGGGG TGCCACAACT CAGACTTTCG GAACAGAGAC    2160

ATGACCGCCT TACTGAAGGT TTCTAGTTGT GACAAGAACA CTGGTGATTA TTACGAGGAC    2220

AGTTATGAAG ATATTTCAGC ATACTTGCTG AGTAAAAACA ATGCCATTGA ACCAAGAAGC    2280

TTCTCCCAGA ATTCAAGACA CCCTAGCACT AGGCAAAAGC AATTTAATGC CACCCCACCA    2340

GTCTTGAAAC GCCATCAACG GGAAATAACT CGTACTACTC TTCAGTCAGA TCAAGAGGAA    2400

ATTGACTATG ATGATACCAT ATCAGTTGAA ATGAAGAAGG AAGATTTTGA CATTTATGAT    2460

GAGGATGAAA ATCAGAGCCC CCGCAGCTTT CAAAAGAAAA CACGACACTA TTTTATTGCT    2520

GCAGTGGAGA GGCTCTGGGA TTATGGGATG AGTAGCTCCC CACATGTTCT AAGAAACAGG    2580

GCTCAGAGTG GCAGTGTCCC TCAGTTCAAG AAAGTTGTTT CCAGGAATT TACTGATGGC     2640

TCCTTTACTC AGCCCTTATA CCGTGGAGAA CTAAATGAAC ATTTGGGACT CCTGGGGCCA    2700

TATATAAGAG CAGAAGTTGA AGATAATATC ATGGTAACTT TCAGAAATCA GGCCTCTCGT    2760

CCCTATTCCT TCTATTCTAG CCTTATTTCT TATGAGGAAG ATCAGAGGCA AGGAGCAGAA    2820

CCTAGAAAAA ACTTTGTCAA GCCTAATGAA ACCAAAACTT ACTTTTGGAA AGTGCAACAT    2880

CATATGGCAC CCACTAAAGA TGAGTTTGAC TGCAAAGCCT GGGCTTATTT CTCTGATGTT    2940

GACCTGGAAA AAGATGTGCA CTCAGGCCTG ATTGGACCCC TTCTGGTCTG CCACACTAAC    3000

ACACTGAACC CTGCTCATGG GAGACAAGTG ACAGTACAGG AATTTGCTCT GTTTTTCACC    3060

ATCTTTGATG AGACCAAAAG CTGGTACTTC ACTGAAAATA TGGAAAGAAA CTGCAGGGCT    3120

CCCTGCAATA TCCAGATGGA AGATCCCACT TTTAAAGAGA ATTATCGCTT CCATGCAATC    3180

AATGGCTACA TAATGGATAC ACTACCTGGC TTAGTAATGG CTCAGGATCA AAGGATTCGA    3240

TGGTATCTGC TCAGCATGGG CAGCAATGAA AACATCCATT CTATTCATTT CAGTGGACAT    3300

GTGTTCACTG TACGAAAAAA AGAGGAGTAT AAAATGGCAC TGTACAATCT CTATCCAGGT    3360

GTTTTTGAGA CAGTGGAAAT GTTACCATCC AAAGCTGGAA TTTGGCGGGT GGAATGCCTT    3420

ATTGGCGAGC ATCTACATGC TGGGATGAGC ACACTTTTTC TGGTGTACAG CAATAAGTGT    3480

CAGACTCCCC TGGGAATGGC TTCTGGACAC ATTAGAGATT TTCAGATTAC AGCTTCAGGA    3540

CAATATGGAC AGTGGGCCCC AAAGCTGGCC AGACTTCATT ATTCCGGATC AATCAATGCC    3600

TGGAGCACCA AGGAGCCCTT TTCTTGGATC AAGGTGGATC TGTTGGCACC AATGATTATT    3660

CACGGCATCA AGACCCAGGG TGCCCGTCAG AAGTTCTCCA GCCTCTACAT CTCTCAGTTT    3720

ATCATCATGT ATAGTCTTGA TGGGAAGAAG TGGCAGACTT ATCGAGGAAA TTCCACTGGA    3780

ACCTTAATGG TCTTCTTTGG CAATGTGGAT TCATCTGGGA TAAAACACAA TATTTTTAAC    3840

CCTCCAATTA TTGCTCGATA CATCCGTTTG CACCCAACTC ATTATAGCAT TCGCAGCACT    3900

CTTCGCATGG AGTTGATGGG CTGTGATTTA AATAGTTGCA GCATGCCATT GGGAATGGAG    3960

AGTAAAGCAA TATCAGATGC ACAGATTACT GCTTCATCCT ACTTTACCAA TATGTTTGCC    4020
```

-continued

| | | | | |
|---|---|---|---|---|
| ACCTGGTCTC | CTTCAAAAGC | TCGACTTCAC | CTCCAAGGGA | GGAGTAATGC CTGGAGACCT 4080 |
| CAGGTGAATA | ATCCAAAAGA | GTGGCTGCAA | GTGGACTTCC | AGAAGACAAT GAAAGTCACA 4140 |
| GGAGTAACTA | CTCAGGGAGT | AAAATCTCTG | CTTACCAGCA | TGTATGTGAA GGAGTTCCTC 4200 |
| ATCTCCAGCA | GTCAAGATGG | CCATCAGTGG | ACTCTCTTTT | TTCAGAATGG CAAAGTAAAG 4260 |
| GTTTTTCAGG | GAAATCAAGA | CTCCTTCACA | CCTGTGGTGA | ACTCTCTAGA CCCACCGTTA 4320 |
| CTGACTCGCT | ACCTTCGAAT | TCACCCCCAG | AGTTGGGTGC | ACCAGATTGC CCTGAGGATG 4380 |
| GAGGTTCTGG | GCTGCGAGGC | ACAGGACCTC | TACTGAGGGT | GGCCACTGCA GCACCTGCCA 4440 |
| CTGCCGTCAC | CTCTCCCTCC | TCAGCTCCAG | GGCAGTGTCC | CTCCCTGGCT TGCCTTCTAC 4500 |
| CTTTGTGCTA | AATCCTAGCA | GACACTGCCT | TGAAGCCTCC | TGAATTAACT ATCATCAGTC 4560 |
| CTGCATTTCT | TTGGTGGGGG | GCCAGGAGGG | TGCATCCAAT | TTAACTTAAC TCTTACCTAT 4620 |
| TTTCTGCAG | | | | 4629 |

What is claimed is:

1. An adenoviral vector comprising at least one heterologous DNA sequence and at least one intron which is not part of the adenoviral genome, wherein said vector is free of adenoviral DNA sequences encoding E1 proteins.

2. The vector of claim 1, further comprising a 3' untranslated region, a 5' untranslated region, or both a 5' untranslated region and a 3' untranslated region operatively linked to said heterologous DNA sequence.

3. The vector of claim 1, wherein said heterologous DNA sequence encodes a heterologous protein.

4. The vector of claim 1, wherein said heterologous DNA sequence is selected from the group consisting of: DNA encoding Factor VIII; DNA encoding Factor IX; DNA encoding a cytokine; DNA encoding a tumor necrosis factor (TNF); DNA encoding an interferon; DNA encoding an interleukin; DNA encoding GM-CSF; DNA encoding adenosine deaminase, or ADA; DNA encoding a cellular growth factor; DNA encoding soluble CD4; DNA encoding an LDL receptor; DNA encoding ApoE; DNA encoding ApoC; DNA encoding ApoA1; DNA encoding alpha-1 antitrypsin (α1AT); DNA encoding ornithine transcarbamylase (OTC); DNA encoding CFTR; DNA encoding insulin; DNA encoding a viral thymidine kinase; and DNA encoding an antisense sequence which inihibits viral replication.

5. The vector of claim 1, wherein said intron is at least a portion of an intron of the Factor IX gene.

6. The vector of vector claim 1, wherein said intron is at least a portion of an intron of the Factor VIII gene.

7. The vector of claim 1, wherein said intron comprises the first intron of the apolipoprotein A-1 gene.

8. The vector of claim 3, wherein said heterologous DNA sequence and said intron are from the same gene.

9. The vector of claim 3, wherein said heterologous DNA sequence and said intron are from different genes.

10. The vector of claim 5, wherein said intron is the full seventh intron of the Factor IX gene.

11. An adenoviral vector comprising at least one heterologous DNA sequence and at least one intron which is not part of the adenoviral genome, wherein said vector is free of at least the majority of adenoviral E1 and E3 DNA sequences.

12. The vector of claim 11, wherein said vector also is free of at least a portion of adenoviral E2 DNA sequences.

13. The vector of claim 11, wherein said vector also is free of at least a portion of adenoviral E4 DNA sequences.

14. The vector of claim 11, wherein said vector also is free of at least a portion of adenoviral E2 and E4 DNA sequences.

15. The vector of claim 11, further comprising a 3' untranslated region, a 5' untranslated region, or both a 5' untranslated region and a 3' untranslated region operatively linked to said heterologous DNA sequence.

16. The vector of claim 11, wherein said heterologous DNA sequence encodes a heterologous protein.

17. The vector of claim 11, wherein said heterologous DNA sequence is selected from the group consisting of: DNA encoding Factor VIII; DNA encoding Factor IX; DNA encoding a cytokine; DNA encoding a tumor necrosis factor (TNF); DNA encoding an interferon; DNA encoding an interleukin; DNA encoding GM-CSF; DNA encoding adenosine deaminase, or ADA; DNA encoding a cellular growth factor; DNA encoding soluble CD4; DNA encoding an LDL receptor; DNA encoding ApoE; DNA encoding ApoC; DNA encoding ApoA1; DNA encoding alpha-1 antitrypsin (α1AT); DNA encoding ornithine transcarbamylase (OTC); DNA encoding CFTR; DNA encoding insulin; DNA encoding a viral thymidine kinase; and DNA encoding an antisense sequence which inihibits viral replication.

18. The vector of claim 11, wherein said intron is at least a portion of an intron of the Factor IX gene.

19. The vector of claim 11, wherein said intron is at least a portion of an intron of the Factor VIII gene.

20. The vector of claim 11, wherein said intron comprises the first intron of the apolipoprotein A-1 gene.

21. The vector of claim 16, wherein said heterologous DNA sequence and said intron are from the same gene.

22. The vector of claim 16, wherein said heterologous DNA sequence and said intron are from different genes.

23. The vector of claim 18, wherein said intron is the full seventh intron of the Factor IX gene.

24. An adenoviral vector comprising at least one heterologous DNA sequence and at least one intron selected from the group consisting of at least a portion of an intron of the Factor IX gene, the full seventh intron of the Factor IX gene, at least a portion of an intron of the Factor VIII gene and the first intron of the apolipoprotein A-1 gene, said at least one intron enhancing expression of said at least one heterologous DNA sequence.

25. The vector of claim 24, wherein said vector is free of adenoviral DNA sequences encoding E1 proteins.

26. The vector of claim 24, wherein said vector is free of at least the majority of adenoviral E1 and E3 DNA sequences.

27. The vector of claim 24, further comprising a 3' untranslated region, a 5' untranslated region, or both a 5' untranslated region and a 3' untranslated region operatively linked to said heterologous DNA sequence.

28. The vector of claim 24, wherein said heterologous DNA sequence encodes a heterologous protein.

29. The vector of claim 24, wherein said heterologous DNA sequence is selected from the group consisting of: DNA encoding Factor VIII; DNA encoding Factor IX; DNA encoding a cytokine; DNA encoding a tumor necrosis factor (TNF); DNA encoding an interferon; DNA encoding an interleukin; DNA encoding GM-CSF; DNA encoding adenosine deaminase, or ADA; DNA encoding a cellular growth factor; DNA encoding soluble CD4; DNA encoding an LDL receptor; DNA encoding ApoE; DNA encoding ApoC; DNA encoding ApoA1; DNA encoding alpha-1 antitrypsin ($\alpha$1AT); DNA encoding ornithine transcarbamylase (OTC); DNA encoding CFTR; DNA encoding insulin; DNA encoding a viral thymidine kinase; and DNA encoding an antisense sequence which inihibits viral replication.

30. The vector of claim 24, wherein said intron is at least a portion of an intron of the Factor IX gene.

31. The vector of claim 24, wherein said intron is at least a portion of an intron of the Factor VIII gene.

32. The vector of claim 24, wherein said intron comprises the first intron of the apolipoprotein A-1 gene.

33. The vector of claim 26, wherein said vector also is free of at least a portion of adenoviral E2 DNA sequences.

34. The vector of claim 26, wherein said vector also is free of at least a portion of adenoviral E4 DNA sequences.

35. The vector of claim 26, wherein said vector also is free of at least a portion of adenoviral E2 and E4 DNA sequences.

36. The vector of claim 28, wherein said heterologous DNA sequence and said intron are from the same gene.

37. The vector of claim 28, wherein said heterologous DNA sequence and said intron are from different genes.

38. The vector of claim 30, wherein said intron is the full seventh intron of the Factor IX gene.

39. A method of expressing a heterologous DNA sequence contained in an adenoviral vector, comprising operatively linking said heterologous DNA sequence with at least one intron selected from the group consisting of at least a portion of an intron of the Factor IX gene, the full seventh intron of the Factor IX gene, at least a portion of an intron of the factor VIII gene and the first intron of the apolipoprotein A-1 gene, said at least one intron enhancing expression of said heterologous DNA sequence.

40. The method of claim 39, wherein said vector is free of adenoviral DNA sequences encoding E1 proteins.

41. The method of claim 39, wherein said vector is free of at least the majority of adenoviral E1 and E3 DNA sequences.

42. The method of claim 39, further comprising operatively linking said heterologous DNA sequence with a 3' untranslated region, a 5' untranslated region, or both a 5' untranslated region and a 3' untranslated region.

43. The method of claim 39, wherein said heterologous DNA sequence encodes a heterologous protein.

44. The method of claim 39, wherein said heterologous DNA sequence is selected from the group consisting of: DNA encoding Factor VIII; DNA encoding Factor IX; DNA encoding a cytokine; DNA encoding a tumor necrosis factor (TNF); DNA encoding an interferon; DNA encoding an interleukin; DNA encoding GM-CSF; DNA encoding adenosine deaminase, or ADA; DNA encoding a cellular growth factor; DNA encoding soluble CD4; DNA encoding an LDL receptor; DNA encoding ApoE; DNA encoding ApoC; DNA encoding ApoA1; DNA encoding alpha-1 antitrypsin ($\alpha$1AT); DNA encoding ornithine transcarbamylase (OTC); DNA encoding CFTR; DNA encoding insulin; DNA encoding a viral thymidine kinase; and DNA encoding an antisense sequence which inihibits viral replication.

45. The method of claim 39, wherein said intron is at least a portion of an intron of the Factor IX gene.

46. The method of claim 39, wherein said intron is at least a portion of an intron of the Factor VIII gene.

47. The method of claim 39, wherein said intron comprises the first intron of the apolipoprotein A-1 gene.

48. The method of claim 41, wherein said vector also is free of at least a portion of adenoviral E2 DNA sequences.

49. The method of claim 41, wherein said vector also is free of at least a portion of adenoviral E4 DNA sequences.

50. The method of claim 41, wherein said vector also is free of at least a portion of adenoviral E2 and E4 DNA sequences.

51. The method of claim 43, wherein said heterologous DNA sequence and said intron are from the same gene.

52. The method of claim 43, wherein said heterologous DNA sequence and said intron are from different genes.

53. The method of claim 45, wherein said intron is the full seventh intron of the Factor IX gene.

54. An adenoviral vector comprising at least one heterologous DNA sequence, wherein said vector is free of adenoviral DNA sequences encoding E1 proteins and said at least one heterologous DNA sequence comprises at least one intron.

55. The vector of claim 54, further comprising a 3' untranslated region, a 5' untranslated region, or both a 5' untranslated region and a 3' untranslated region operatively linked to said heterologous DNA sequence.

56. The vector of claim 54, wherein said heterologous DNA sequence encodes a heterologous protein.

57. The vector of claim 54, wherein said heterologous DNA sequence is selected from the group consisting of: DNA encoding Factor VIII; DNA encoding Factor IX; DNA encoding a cytokine; DNA encoding a tumor necrosis factor (TNF); DNA encoding an interferon; DNA encoding an interleukin; DNA encoding GM-CSF; DNA encoding adenosine deaminase, or ADA; DNA encoding a cellular growth factor; DNA encoding soluble CD4; DNA encoding an LDL receptor; DNA encoding ApoE; DNA encoding ApoC; DNA encoding ApoA1; DNA encoding alpha-1 antitrypsin ($\alpha$1AT); DNA encoding ornithine transcarbamylase (OTC); DNA encoding CFTR; DNA encoding insulin; DNA encoding a viral thymidine kinase; and DNA encoding an antisense sequence which inihibits viral replication.

58. The vector of claim 54, wherein said intron is at least a portion of an intron of the Factor IX gene.

59. The vector of claim 54, wherein said intron is at least a portion of an intron of the Factor VIII gene.

60. The vector of claim 54, wherein said intron comprises the first intron of the apolipoprotein A-1 gene.

61. The vector of claim 56, wherein said heterologous DNA sequence and said intron are from the same gene.

62. The vector of claim 56, wherein said heterologous DNA sequence and said intron are from different genes.

63. The vector of claim 58, wherein said intron is the full seventh intron of the Factor IX gene.

64. An adenoviral vector comprising at least one heterologous DNA sequence wherein said vector is free of at least the majority of adenoviral E1 and E3 DNA sequences and said at least one heterologous DNA sequence comprises at least one intron.

65. The vector of claim 64, wherein said vector also is free of at least a portion of adenoviral E2 DNA sequences.

66. The vector of claim 64, wherein said vector also is free of at least a portion of adenoviral E4 DNA sequences.

67. The vector of claim 64, wherein said vector also is free of at least a portion of adenoviral E2 and E4 DNA sequences.

68. The vector of claim 64, further comprising a 3' untranslated region, a 5' untranslated region, or both a 5' untranslated region and a 3' untranslated region operatively linked to said heterologous DNA sequence.

69. The vector of claim 64, wherein said heterologous DNA sequence encodes a heterologous protein.

70. The vector of claim 64, wherein said heterologous DNA sequence is selected from the group consisting of: DNA encoding Factor VIII; DNA encoding Factor IX; DNA encoding a cytokine; DNA encoding a tumor necrosis factor (TNF); DNA encoding an interferon; DNA encoding an interleukin; DNA encoding GM-CSF; DNA encoding adenosine deaminase, or ADA; DNA encoding a cellular growth factor; DNA encoding soluble CD4; DNA encoding an LDL receptor; DNA encoding ApoE; DNA encoding ApoC; DNA encoding ApoA1; DNA encoding alpha-1 antitrypsin ($\alpha$1AT); DNA encoding ornithine transcarbamylase (OTC); DNA encoding CFTR; DNA encoding insulin; DNA encoding a viral thymidine kinase; and DNA encoding an antisense sequence which inihibits viral replication.

71. The vector of claim 64, wherein said intron is at least a portion of an intron of the Factor IX gene.

72. The vector of claim 64, wherein said intron is at least a portion of an intron of the Factor VIII gene.

73. The vector of claim 64, wherein said intron comprises the first intron of the apolipoprotein A-1 gene.

74. The vector of claim 69, wherein said heterologous DNA sequence and said intron are from the same gene.

75. The vector of claim 69, wherein said heterologous DNA sequence and said intron are from different genes.

76. The vector of claim 71, wherein said intron is the full seventh intron of the Factor IX gene.

77. An adenoviral vector comprising at least one heterologous DNA sequence, said at least one heterologous DNA sequence comprising at least one intron selected from the group consisting of at least a portion of an intron of the Factor IX gene, the full seventh intron of the Factor IX gene, at least a portion of an intron of the Factor VIII gene and the first intron of the apolipoprotein A-1 gene, wherein said at least one intron enhances expression of said at least one heterologous DNA sequence.

78. The vector of claim 77, wherein said vector is free of adenoviral DNA sequences encoding E1 proteins.

79. The vector of claim 77, wherein said vector is free of at least the majority of adenoviral E1 and E3 DNA sequences.

80. The vector of claim 77, further comprising a 3' untranslated region, a 5' untranslated region, or both a 5' untranslated region and a 3' untranslated region operatively linked to said heterologous DNA sequence.

81. The vector of claim 77, wherein said heterologous DNA sequence encodes a heterologous protein.

82. The vector of claim 77, wherein said heterologous DNA sequence is selected from the group consisting of: DNA encoding Factor VIII; DNA encoding Factor IX; DNA encoding a cytokine; DNA encoding a tumor necrosis factor (TNF); DNA encoding an interferon; DNA encoding an interleukin; DNA encoding GM-CSF; DNA encoding adenosine deaminase, or ADA; DNA encoding a cellular growth factor; DNA encoding soluble CD4; DNA encoding an LDL receptor; DNA encoding ApoE; DNA encoding ApoC; DNA encoding ApoA1; DNA encoding alpha-1 antitrypsin ($\alpha$1AT); DNA encoding ornithine transcarbamylase (OTC); DNA encoding CFTR; DNA encoding insulin; DNA encoding a viral thymidine kinase; and DNA encoding an antisense sequence which inihibits viral replication.

83. The vector of claim 77, wherein said intron is at least a portion of an intron of the Factor IX gene.

84. The vector of claim 77, wherein said intron is at least a portion of an intron of the Factor VIII gene.

85. The vector of claim 77, wherein said intron comprises the first intron of the apolipoprotein A-1 gene.

86. The vector of claim 79, wherein said vector also is free of at least a portion of adenoviral E2 DNA sequences.

87. The vector of claim 79, wherein said vector also is free of at least a portion of adenoviral E4 DNA sequences.

88. The vector of claim 79, wherein said vector also is free of at least a portion of adenoviral E2 and E4 DNA sequences.

89. The vector of claim 81, wherein said heterologous DNA sequence and said intron are from the same gene.

90. The vector of claim 81, wherein said heterologous DNA sequence and said intron are from different genes.

91. The vector of claim 83, wherein said intron is the full seventh intron of the Factor IX gene.

92. A method of expressing a heterologous DNA sequence contained in an adenoviral vector, comprising operatively linking said heterologous DNA sequence with at least one intron selected from the group consisting of at least a portion of an intron of the Factor IX gene, the full seventh intron of the Factor IX gene, at least a portion of an intron of the Factor VIII gene and the first intron of the apolipoprotein A-1 gene, wherein said at least one intron enhances expression of said heterologous DNA sequence.

93. The method of claim 92, wherein said vector is free of adenoviral DNA sequences encoding E1 proteins.

94. The method of claim 92, wherein said vector is free of at least the majority of adenoviral E1 and E3 DNA sequences.

95. The method of claim 92, further comprising operatively linking said heterologous DNA sequence with a 3' untranslated region, a 5' untranslated region, or both a 5' untranslated region and a 3' untranslated region.

96. The method of claim 92, wherein said heterologous DNA sequence encodes a heterologous protein.

97. The method of claim 92, wherein said heterologous DNA sequence is selected from the group consisting of: DNA encoding Factor VIII; DNA encoding Factor IX; DNA encoding a cytokine; DNA encoding a tumor necrosis factor (TNF); DNA encoding an interferon; DNA encoding an interleukin; DNA encoding GM-CSF; DNA encoding adenosine deaminase, or ADA; DNA encoding a cellular growth factor; DNA encoding soluble CD4; DNA encoding an LDL receptor; DNA encoding ApoE; DNA encoding ApoC; DNA encoding ApoA1; DNA encoding alpha-1 antitrypsin ($\alpha$1AT); DNA encoding ornithine transcarbamylase (OTC); DNA encoding CFTR; DNA encoding insulin; DNA encoding a viral thymidine kinase; and DNA encoding an antisense sequence which inihibits viral replication.

98. The method of claim 92, wherein said intron is at least a portion of an intron of the Factor IX gene.

99. The method of claim 94, wherein said vector also is free of at least a portion of adenoviral E2 DNA sequences.

100. The method of claim 94, wherein said vector also is free of at least a portion of adenoviral E4 DNA sequences.

101. The method of claim 94, wherein said vector also is free of at least a portion of adenoviral E2 and E4 DNA sequences.

102. The method of claim 96, wherein said heterologous DNA sequence and said intron are from the same gene.

103. The method of claim 96, wherein said heterologous DNA sequence and said intron are from different genes.

104. The method of claim 98, wherein said intron is the full seventh intron of the Factor IX gene.

105. The method of claim 92, wherein said intron is at least a portion of an intron of the Factor VIII gene.

106. The method of claim 92, wherein said intron comprises the first intron of the apolipoprotein A-1 gene.

* * * * *